United States Patent [19]
Haselkorn et al.

[11] Patent Number: 5,792,627
[45] Date of Patent: *Aug. 11, 1998

[54] CYANOBACTERIAL AND PLANT ACETYL-COA CARBOXYLASE

[75] Inventors: Robert Haselkorn; Piotr Gornicki. both of Chicago, Ill.

[73] Assignee: Arch Development Corporation, Chicago, Ill.

[*] Notice: The term of this patent shall not extend beyond the expiration date of Pat. No. 5,539,092

[21] Appl. No.: 485,607

[22] Filed: Jun. 7, 1995

Related U.S. Application Data

[63] Continuation of Ser. No. 956,700, Oct. 2, 1992, Pat. No. 5,539,092.

[51] Int. Cl.$^6$ .................... C12P 21/06; C12N 5/00; C12N 15/00; C07H 21/04
[52] U.S. Cl. .................. 435/69.1; 435/172.3; 435/252.3; 435/252.33; 435/257.2; 435/320.1; 435/419; 536/23.1; 536/23.2; 536/23.7; 935/9; 935/67
[58] Field of Search .................... 800/205, DIG. 55, 800/DIG. 58; 536/23.2, 23.6, 23.7; 435/172.3, 257.2, 320.1, 34, 69.1, 252.3, 252.33, 419; 935/9, 64, 79, 84, 67

[56] References Cited

U.S. PATENT DOCUMENTS

| | | | |
|---|---|---|---|
| 5,162,602 | 11/1992 | Somers et al. | 800/235 |
| 5,498,544 | 3/1996 | Gengenbach et al. | 435/320.1 |
| 5,539,092 | 7/1996 | Haselkorn et al. | 536/23.2 |

FOREIGN PATENT DOCUMENTS

| | | |
|---|---|---|
| 0469810A1 | 5/1992 | European Pat. Off. |
| WO93/11243 | 6/1993 | WIPO |
| WO94/08016 | 4/1994 | WIPO |
| WO94/17188 | 8/1994 | WIPO |
| WO94/23027 | 10/1994 | WIPO |
| WO94/29467 | 12/1994 | WIPO |
| WO95/29246 | 11/1995 | WIPO |
| WO96/31609 | 10/1996 | WIPO |

OTHER PUBLICATIONS

JD Watson et al (1987) Molecular Biology of the Gene p. 313.
H Kondo et al (1991) Proc Natl Sci USA 88: 9730–9733.
V Gamulin et al (1983) Nucleic Acids Research 11: 8537–8546.
T Konishi et al (1994) Proc Natl Acad Sci USA 91: 3598–3601.
Foreign Search Report dated Mar. 27, 1997.
Elborough et al., "Isolation of cDNAs from *Brassica napus* encoding the biotin–binding and transcarboxylase domains of acetyl–CoA carboxylase: assignment of the domain structure in a full–length *Arabidopsis thaliana* genomic clone." *Biochem J.*, 301:599–605, 1994; EMBL Sequence Database, Release 40, 1994, Accession No. X77382.
Egli et al., "Characterization of Maize Acetyl–Coenzyme A Carboxylase," *Plant Physiol.*, 101:499–506, 1993.
Elborough et al., "Studies on wheat acetyl CoA carboxylase and the cloning of a partial cDNA," *Plant Mol. Biol.*, 24:21–34, 1994, XP002026094.
Elborough et al., "Regulation of primary storage products of oil seeds by manipulating the level of genes involved in lipid metabolism on plant acetyl CoA carboxylase," *J. Cell. Biol.*, Supplemental 18A, p. 113, 1994, XP002026102, Abstract X1–418.
Gornicki et al., "Wheat acetyl–CoA carboxylase," *Plant Mol. Biol.*, 22:547–542, 1993.
Gornicki et al. "Genes for Two Subunits of Acetyl Coenzyme A Carboxylase of Anabaena sp. Strain PCC 7120: Biotin Carboxylase and Biotin Carboxyl Carrier Protein," *J. of Bacteriology*, 175(16):5268–5272, 1993; EMBL Sequence Database, Release 35, 1993, Accession No. L14862; EMBL Sequence Database, Release 35, 1993, Accession No. L14863.
Gornicki et al. "Wheat acetyl–coenzyme A carboxylase: cDNA and protein structure," *Proc. Natl. Acad. Sci.*, 91:6860–6864, 1994; EMBL Sequence Database, Release 40, 1994, Accession No. U10187.
Podkowinski et al., "Structure of a gene encoding a cytosolic acetyl–CoA carboxylase of hexaploid wheat," *Proc. Natl. Acad. Sci.*, 93(5):1870–1874, 1996, ISSN:0027–8424, XP002026103; EMBL Sequence Database, Release 47, Accession No. U39321, 1996.
Phung et al., "Genes for Fatty Acid Biosynthesis in the Cyanobacterium Synechococcus sp. strain PCC 7942," *95th General Meeting of the American Society for Microbiology*, May 21–25, 1995, Abstract H–182, ISSN:1060–2011, XP000601370.
Roesler et al., "Structure and Expression of an Arabidopsis Acetyl–Coenzyme A Carboxylase Gene," *Plant Physiol.*, 105:611–617, 1994 (XP 002013209).
Valentin et al., "Glutamate synthase is plastid–encoded in a red alga: Implications for the evolution of glutamate synthases," *Plant Mol. Biol.* 23:77–85, 1993; EMBL Sequence Database Release 39, 1994, Accession No. Z33874, XP002026098.
Slabas et al., "Rapid purification of a high molecular weight subunit polypeptide form of rape seed acetyl CoA carboxylase," *Plant Science*, 39:177–182, 1985.
Winz et al., "Unique structural features and differential phosphorylation of the 280–kDa component (isozyme) of rat liver acetyl–CoA carboxylase," *J. Biol. Chem.* 269(20):14438–14445, 1994, XP002026101.
Sasaki et al., "Chloroplast–encoded protein as a subunit of acetyl–CoA carboxylase in pea plant," *J. Biol. Chem.* 268(33):25118–25123, 1993, XP002013210.

*Primary Examiner*—Bruce R. Campell
*Attorney, Agent, or Firm*—Arnold, White & Durkee

[57] ABSTRACT

The present invention provides isolated and purified polynucleotides that encode plant and cyanobacterial polypeptides that participate in the carboxylation of acetyl-CoA. Isolated cyanobacterial and plant polypeptides that catalyze acetyl-CoA carboxylation are also provided. Processes for altering acetyl-CoA carboxylation, increasing herbicide resistance of plants and identifying herbicide resistant variants of acetyl-CoA carboxylase are also provided.

22 Claims, 19 Drawing Sheets

FIG. 1A

```
ATGCTGGGCGTTTATATAGAAAAATTTATTGAACGTCCGCGCCACATTGAATTTCAAATTTTGGCTGATAATTACGGCAATGTGATTCACT     1980
 A  G  V  Y  I  E  K  F  I  E  R  P  R  H  I  E  F  Q  I  L  A  D  N  Y  G  N  V  I  H  L
TGGGTGAGAGGGATTGCTCAATTCAGCGTCGTAACCAAAAGTTACTAGAAGAAGCCTTGGACTCAGACCTAAGGGAAA                  2070
 G  E  R  G  I  A  Q  F  Q  V  V  T  K  V  T  R  R  R  S  G  T  Q  T  K  G  K
AAATGGGACAAGCGGGTGAAAGCGGCTCAGTTTATCAATTACGCCGGGCAGGTACTATCGAGTTTTGCTAGATAGATCCGGTCAGT          2160
 G  E  R  D  C  S  I  Q  R  R  N  Q  K  L  L  E  E  A  P  S  P  A  L  D  S  D  L  R  E  K
TTTACTTTATGGAGATGAACACCCGGTCAAGTAGAACATCCGTAACTGAGTGGTTACTGAGATGGATTTATTGGTTGAGCAAATCA          2250
 M  G  Q  A  A  V  K  A  A  Q  F  I  N  Y  A  G  T  I  E  F  L  L  D  R  S  G  Q  F
GAATTGCCCAAGGGGAAAGACTTAGACTAACTCAAGACTAGTTTACGCGGTCATGGAGTCGCATCGAATGTCGAAGACC                  2340
 Y  F  M  E  M  N  T  R  I  Q  V  E  H  P  V  T  E  M  V  T  G  V  D  L  L  V  E  Q  I  R
CAGACCAGATTTCCGCCCAGCACCCCAGCATTAGCGGTTATCTCCCCCTGGCGCCTGGCGATTGACTCCCACGTTACA                  2430
 I  A  Q  G  E  R  L  R  L  T  Q  D  D  Q  V  V  L  R  G  H  A  I  E  C  R  I  N  A  E  D  P
CGGATTACCAAAATTCCGCCTACTACGAATTCCTTAATTGGTAAATTGATCGTTGGGCCTGATCGCGTCTATTGCTATTAACCGCATGA      2520
 D  H  D  F  R  P  A  P  G  R  I  S  G  Y  L  P  P  G  G  P  G  V  R  I  D  S  H  V  Y  T
AACGCGGCCCCTCAGGGAATGCGCCATCGTGGATTACCTACAACCATTGGGTTTCATCAAAGAATTATGGAAAATCCCCAATTTTTACAAG     2610
 D  Y  Q  I  P  P  Y  Y  D  S  L  I  G  K  L  I  V  W  G  P  D  R  A  T  A  I  N  R  M  K
GTAATGTGTCTACTAGTTTTGTGCAGGAGATGAATAAAGGGTAATGGTAATAGAGTTCAATCACCAATTACC                         2700
 R  A  L  R  E  C  A  I  T  G  L  P  T  T  I  G  F  H  Q  R  I  M  E  N  P  Q  F  L  Q  G
AATTCCCTAACTCATCGTCCAACATCGTCAGTAATCCTTGCTGCCTAGAAGAACTTCTCGCAACAGGCTAAAAATACCAACACACAC         2790
 N  V  S  T  S  F  V  Q  E  M  N  K  *     *  W  V  M  G  N  R  V  S  I  T  N  Y  Q
 F  P  N  S  S  V  P  T  S  S  V  I  L  A  G  L  E  E  L  L  A  T  G  *

AATGGGGGTGATATCAACACCACTATTGGTGGATGATTTTTCGCAAGGAATGAGAAATGGTTCAGTCGGCCAAGCAATTAAGTTGAA          2880
GGGCAAACGGTTCAGATCGACTTGCGGATACCAGGTCAGAATGACGGAGAAATAAACAGAAATGTCATCACTCCCAATACAGGGCCAAG       2970
AATCCAAACGCTCAGGTTAACACCAGTCATCGATCTAAGCTACTATTTTGTGAATTTACAAAAAACTGCAAGCAAAAGCTGAAAATTTTA     3060
AGCTT                                                                                           3065
```

FIG. 1B

ATGCGTTTCA ACAAGATCCT GATCGCCAAT CGCGGCGAAA TCGCCCTGCG CATTCTCCGC

ACTTGTCAAG AACTCGGGAT CGGCACGATC GCCGTTCACT CCACTGTGGA TCGCAACGCG

CTCCATGTGC AGTTAGCGGA CGAAGCGGTC TGTATTGGGCG AAGCGGCCAG CAGCAAAAGC

TATCTCAATA TCCCCAACAT CATTGCGGCG GCCCTGACCC CTAATGCCAG CGCCATTCAC

CCCGGCTATG GCTTCTTGGC GGAGAATGCC CGCTTTGCAG AAATCTGCGC CGATCACCAT

CTCACCTTTA TTGGCCCCAG CCCCGATTCG ATTCGAGCCA TGGGCGATAA ATCCACCGCT

AAGGAAACAA TGCAGCGGGT CGGCGTTCCG ACGATTCCGG GAGATCGGCT ATCCCGTCAT GATCAAAGCG

GATGTTGATT CGGCTGCCAA AGTTGCTGCC CGGTATGCGG CTGGTGCGTG ACCCTGCAGA TCTGGAAAAA

ACGGCGGGGG GCGGTGGTCG CGGTCCCAAGG AGAAGCCGAG GCAGCTTTTG GGAATCCAGG ACTGTATCTC

CTGTTCCTTG CTGCCCCAAGG AGAAGCCGAG GCAGCTTTTG GGAATCCAGG ACTGTATCTC

CTGTTCCTTG CTGCCCCAAGG ACGCCACGTT GAATTTCAGA TCTTGGCCGA TGCCTACGGC

GAAAAATTTA TCGATCGCCC ACGCCACGTT GAATTTCAGA TCTTGGCCGA TGCCTACGGC

AATGTAGTGC ATCTAGGCGA GCGCGATTGC TCCATTCAAC GTCGTCACCA AAAGCTGCTC

GAAGAAGCCC CCAGTCCGGC GCTATCGGCA GACCTGCGGC AGAAAATGGG CGATGCCGCC

FIG. 2A

```
GTCAAAGTCG CTCAAGCGGAT CGGCTACATC GGTGCCGGCA CCGTGGAGTT TCTGGTCGAT
GCGACCGGCA ACTTCTACTT CATGGGAGATG AATACCCGCA TCCAAGTCGA GCATCCAGTC
ACAGAAATGA TTACGGGACT GGACTTGATT GCGGAGCAGA TTCGGATTGC CCAAGGCGAA
GCGCTGCGCT TCCGGCAAGC CGATATTCAA CTGCGCGGCC ATGCGGATCGA ATGCCGTATC
AATGCGGAAG ATCCGGAATA CAATTTCCGG CCGAATCCTG GCCGCATTAC AGGCTATTTA
CCGCCCGGCG GCCCCGGCGT TCGTGTCGAT TCCCATGTTT ATACCGACTA CGAAATTCCG
CCCTATTACG ATTCGCTGAT TGGCAAATTG ATTGTCTGGG GTGCAACACG GGAAGAGGCG
ATCGCGCGGA TGCAGCGTGC TCTGCGGGAA TGCGCCATCA CCGGCTTGCC GACGACCCTT
AGTTTCCATC AGCTGATGTT GCAGATGCCT GAGTTCCTGC GCGGGGAACT CTATACCAAC
TTTGTTGAGC AGGTGATGCT ACCTCGGATC CTCAAGTCCT AG
```

FIG. 2B amino acid sequence

MRFNKILIAN RGEIALRILR TCEELGIGTI AVHSTVDRNA LHVQLADEAV CIGEAASSKS

YLNIPNIIAA ALTRNASAIH PGYGFLAENA RFAEICADHH LTFIGPSPDS IRAMGDKSTA

KETMQRVGVP TIPGSDGLLT DVDSAADVAA EIGYPVMIKA TAGGGGRGMR LVREPADLEK

LFLAAQGEAE AAFGNPGLYL EKFIDRPRHV EFQILADAYG NVVELGERDC SIQRRHQKLL

EEAPSPALSA DLRQKMGDAA VKVAQAIGYI GAGTVEFLVD ATGNFYFMEM NTRIQVEHPV

TEMITGLDLI AEQIRIAQGE ALRFRQADIQ LRGHAIECRI NAEDPEYNFR PNPGRITGYL

PPGGPGVRVD SHVYTDYEIP PYYDSLIGKL IVWGATREEA IARMQRALRE CAITGLPTTL

SFHQLMLQMP EFLRGELYTN FVEQVMLPRI LKS

FIG. 2C

```
                                                                              70
Wh ACC   ..........................................................
Rt ACC   MDEPSPLAKTLELNQHSRFIIGSVSEDNSEDEIS-NLVKLDLEEKEGSLSPASVSSDTLSDLGISALQDG
Ch ACC   MEESSQPAKPLEMNPHSRFIIGSVSEDNSEDETSSLVKLDLLEEKERSLSPVSVCSDSLSDLGLPSAQDG
Yt ACC                                                          MSEESLFESSP
Sy ACC   ..........................................................
An ACC   ..........................................................
Ec ACC   ..........................................................
Hm PCCA  ..........................................................
Rt PCCA                                                    MPYRERFC
Yt PC    ..........................................................

140
Wh ACC   ..........................................................
Rt ACC   LAFHMRSSMSGLHLVKQGRKRKKIDSQRDFTVASPAEFVTRFGGNKVIEKVLIANNGIAABKCMRSIRRW
Ch ACC   LANHMRPSMSGLHLVKQGRDRKKVDVQRDFTVASPAEFVTRFGGNRVIEKVLIANNGIAAVKCMRSIRRW
Yt ACC   QKMEYEITNYSERHTELPGHFIGLNTVDKLEESPLRDFVKSHGGHTVISKILIANNGIAAVKEIRSVRKW
Sy ACC                                                MRFNKILIANRGEIALRILRTCEEL
An ACC                                                MKRFKILIANRGEIALRILRACEEM
Ec ACC                                                MLDKIVIANRGEIALRILRACKEL
Hm PCCA                  MLSAALRTLKHVLYYSRQCLMVSRNLGSVGYDPNEKTFDKILVANRGEIACRVIRTCKKM
Rt PCCA  AIRWCRNSGRSSQQLLWTLKRAPVYSQQCLVVSRSLSSVEYEPKEKTFDKILIANRGEIACRVIKTCRKM
Yt PC                                      MSQRKFAGLRDNFNLLGEK-NKILVANRGEIPIRIFRTAHEL
                                                     *    **  ***
```

FIG. 3A

```
                                                                                              210
Wh ACC  ........SYEMFRNERAIRFVVMVTPEDLKANAEYIKMADHYVPVPGGANNNNYANVELILDIAKRIPVQAVWAGWG
Rt ACC  ........SYEMFRNERAIRFVVMVTPEDLKANAEYIKMADHYVPVPGGPNNNNYANVELILDIAKRIPVQAVWAGWG
Ch ACC  ........AYETFGDDRTVQFVAMATPEDLEANAEYIRMADQYIEVPGGTNNNNYANVDLIVDIAERADVDAVWAGWG
Yt ACC  ........GIGTIAVHSTVD--RNALHVQLADEAVCIGEAASS------KSYLNIPNIIAAALTRNASAIHPGTG
Sy ACC  ........GIATIAVHSTVD--RNALHVQLADEAVCIGEPASA------KSYLNIPNIIAAALTRNASAIHPGYG
An ACC  ........GIKTVAVHSSAD--RDLKHVLLADETVCIGPAPSV------KSYLNIPAIISAAETTGAVAIHPGYG
Ec ACC  ........GIKTVAIHSDVD--ASSVHVKMADEAVCVGPAPTS------KSYLNMDAIMEAIKKTRAQAVHPGYG
Hm PCCA ........GIRTVAIHSDVD--ASSVHVKMADEAVCVGPAPTS------KSYLNMDAIMEAIKKTGAQAVHPGYG
Rt PCCA ........SMQTVAIYSHED--RLSTHKQKADEAYVIGEVGQYTPV-----GAYLAIDEIISIAQKHQVDFIHPGYG
Yt PC                                                                            *     *

280
Wh ACC  HASENPKLPELL--LKNGIAFMGPPSQAMWALGDKIASSIVAQTAGIPTLPWSGSGLRVDWQENDFSKRI
Rt ACC  HASENPKLPELL--HKNGIAFMGPPSQAMWALGDKIASSIVAQTAGIPTLPWNGSGLRVDWQENDLQKRI
Ch ACC  HASENPLLPEKLSQSKRKVIFIGPPGNAMRSLGDKISSTIVAQSAKVPCIPWSGTGVDTVH--VDEKTGL
Yt ACC  FLAENARFAEIC--ADHHLTFIGPSPDSIRAMGDKSTAKETMQRVGVPTIPGSDG-L
Sy ACC  FLSENAKFAEIC--ADHHIAFIGPTPEAIRLMGDKSTAKETMQKAGVPTCPGSEG-L
An ACC  FLSENANFAEQV--ERSGFIFIGPKAETIRLMGDKVSAIAAMKKAGVPCVPGSDGPL
Ec ACC  FLSENKEFARCL--AAEDVVFIGPDTHAIQAMGDKIESKLLAKKAEVNTIPGFDG-V
Hm PCCA FLSENKEFAKCL--AAEDVTFIGPDTHAIQAMGDKIESKLLAKRAKVNTIPGFDG-V
Rt PCCA FLSENSEFADKV--VKAGITWIGPAEVIDSVGDKVSARNLAAKANVPTVPGTPG-P
Yt PC    ***                  **        ***                *
```

FIG. 3B

```
Wh ACC  .........VMIKASWGGGGKGIRKVHNDDEVRALFKQVGEVPGS----  350
Rt ACC  LNVPQDLYEKGYVKDVDDGLKAAEEVGYPVMIKASEGGGGKGIRKVHNDDEVRALFKQVGEVPGS----
Ch ACC  LNVPQELYEKGYVKDADDGLRAAEEVGYPVMIKASEGGGGKGIRKVNNADDFPNLFRQVQAEVPGS----
Yt ACC  VSVDDDIYQKGCCTSPEDGLQKAKRIGFPVMIKASEGGGGKGIRKVNNADDFPNLFRQFQAEVPGS----
Sy ACC  ----LTDVDSAAKVAAEIGYPVMIKATAGGGGRGMRLVREPADLEKLFLAAQGEAEAAFGNP
An ACC  ----VETEQEGLELAKDIGYPVMIKATAGGGGRGMRLVRSPDEFVKLFLAAQGEAGAAFGNA
Ec ACC  ----GDDMDKNRAIAKRIGYPVIIKASGGGGRGMRVVRGDAELAQSISMTRAEAKAAFSND
Hm PCCA ----VKDAEEAVRIAREIGYPVMIKASAGGGGKGMRIAWDDEETRDGFRLSSQEAASSFGDD
Rt PCCA ----LKDADEAVRIAREIGYPVMIKASAGGGGKGMRIPWDDEETRDGFRFSSQEAASSFGDD
Yt PC   ----IETVEEALDFVNEYGYPVIIKAAFGGGGRGMRVVREGDDVADAFQRATSEARTAFGNG
        **** *** **** ****  *

Wh ACC  PIFIMKVASQSRHLEVQLLCDKHGNVAALHSRDCSVQRRHQKIIEEGPITVAPPETIKELEQAARRLAKC  420
Rt ACC  PIFVMRLAKQSRHLEVQILADQYGNAISLFGRDCSVQRRHQKIIEEAPAIATPAVFEHMEQCAVKLAKM
Ch ACC  PIFVMRLAKQSRHLEVQILADQYGNAISLFGRDCSGQRRHQKIIEEAPASIATSVVFEHMEQCAVKLAKM
Yt ACC  PIFIMKLAGRARHLEVQLLADQYGTNISLFGRDCSVQRRHQKIIEEAPVTIAKAETFHEMEKAAVRLGKL
Sy ACC  GLYLEKFIDRPRHVEFQILADAYGNVVHLGERDCSIQRRHQKLLEEAPSPALSADLRQKMGDAAVKVAQA
An ACC  GVYIEKFIERPRHIEFQILADNYGNVIHLGERDCSIQRRNQKLLEEAPSPALDSDLREKMGQAAVKAAQF
Ec ACC  MVYMEKYLENPRHVEIQVLADGQGNAIYLAERDCSMQRRHQKVVEEAPAGITPELRRYIGERCAKACVD
Hm PCCA RLLIEKFIDNPRHIEIQVLGDKHGNALWLNERECSIQRRNQKVVEEAPSIFLDAETRRAMGEQAVALARA
Rt PCCA RLLIEKFIDNPRHIEIQVLGDKHGNALWLNERECSIQRRNQKVVEEAPSIFLDPETRRAMGEQAVAWPKA
Yt PC   TCFVERFLDKPKHIEVQLLADNHGNVVHLFERDCSVQRRHQKVVEVAPAKTLPREVRDAILTDAVKLAKE
        *  *  ** *** ***  **  *   **
```

FIG. 3C

```
Wh ACC    VQYQGAAIVEYLYSMETGEYYFLELNPRLQVEHPVTEWIAEINLPASQVVVGMGIPLYNIPEIRRFYGIE 490
Rt ACC    VGYVSAGTVEYLYSQD-GSFYFLELNPRLQVEHPCTEMVADVNLPAAQLIAMGIPLFRIKDIRMMYGVS
Ch ACC    VGYVSAGTVEYLYSQD-GSFYFLELNPRLQVEHPCTEMVADVNLPAAQLIAMGIPLHRIKDIRVMYGVS
Yt ACC    VGYVSAGTVEYLYSHDDGKFYFLELNPRLQVEHPTEMVSGVNLPAAQLQIAMGIPMHRISDIRTLYGMN
Sy ACC    IGYIGAGTVEFLVD-ATGNFYFMEMNTRIQVEHPVTEMITGLDLIAEQIRIAQGEALRFQADIQ------
An ACC    INYAGAGTIEFLLD-RSGQFYFMEMNTRIQVEHPVTEMVTGVDLLVEQIRIAQGERLRLTQDQVV-----
Ec ACC    IGYRGAGTFEFLF--ENGEFYFIEMNTRLQVEHPVTEMITGVDLIKEQMRIAAGQPLSIKQEEVH-----
Hm PCCA   VKYSSAGTVEFLVDSK-KNFYFLEMNTRLQVEHPVTECIHWPGPSPGKTVLQEHLSGTNKLIFA------
Rt PCCA   VKYSSAGTVEFLVDSQ-KNFYFLEMNTRLQVEHPVTECITGLDLVQEMILVAKGYPLRHKQEDIP-----
Yt PC     CGYRNAGTAEFLVDNQ-NRHYFIEINPRIQVEHTITEEITGIDIVAAQIQIAAGASLPQLGLFQDKIT---
           *  ***  * *             *  * *  *******    *

Wh ACC    HGGGYHAWKEISAVATKFDLDKAQSVKPKGHCVAVRVTSEDPDDGFK-PTSGRVEELNFKSKPNVWAYF- 560
Rt ACC    PWGDAPIDFENSAHVPC------------------------------PRGHVIAARITSENPDEGFK-PSSGTVQELNFRSNKNVWGYF-
Ch ACC    PWGDGSIDFENSAHVPC------------------------------PRGHVIAARITSENPDEGFK-PSSGTVQELNFRSNKNVWGYF-
Yt ACC    PHSASEIDFEFKTQDAT---KKQRRPIPKGHCTACRITSEDPNDGFK-PSGGTLHELNFRSSSNVWGYG-
Sy ACC    ------------------------------------------------LRGHAIECRINAEDPEYNF-RPNPGRITG--YLPPGG-PGVRV
An ACC    ------------------------------------------------LRGHAIECRINAEDPDHDF-RPAPGRISG--YLPPGG-PGVRI
Ec ACC    ------------------------------------------------VRGHAVECRINAEDPN-TF-LPSPGKITR--FHAPGG-FGVRW
Hm PCCA   ------------------------------------------------FNGWAVECRVYAEDPYKSFGLPSIGRLSQ--YQEPLHLPGCRV
Rt PCCA   ------------------------------------------------ISGWAVECRVYAEDPYKSFGLPSIGRLSQ--YQEPIHLPGVRV
Yt PC     ------------------------------------------------TRGFAIQCRITTEDPAKNFQ-PDTGRIEV--YRSAGG-NGVRL
                                                            *    *                      *
```

```
Wh ACC     --HISLVNLTVTLNIDGSKYTIETVRGGPRSYKLRINESEVEAEIHFLRDGGLLMQLDGNSHVIYAETEA 770
Rt ACC     --HTLLNTVDVELIYEGIKYVLKVTRQSPNSYVVIMNGSCVEVDVHRLSDGGLLLSYDGSSYTTYMKEEV
Ch ACC     --HTLLNTVDVELIYEGRKYVLKVTRQSPNSYVVIMNSSCVEVDVHRLSDGGLLLSYDGSSYTTYMKEEV
Yt ACC     --DLLQTMFPVDFIHEGKRYKFTVAKSGNDRYTLFINGSKCDIILRQLSDGGLLIAIGGKSHTIYWKEEV
An ACC     TLKSDDFELTVRKAVGVNNSVVPVVTAPLSGVVGSGLPSAIPIVAHAAPSPSPEPGTSRAADHAVTSSGS
Ec ACC     MDIRKIKKLIELVEESGISELEISEGEESVRISRAAPAASFPVMQQAYAAPMMQQPAQSNAAAPATVPS
Hm PCCA    HTVVASNNGSVFSVEVDGSKLNVTSTWNLASPLLSVSVDGTQRTVQCLSREAGGNMSIQFLGTVYKVNIL
Rt PCCA    HTVVASNNGPTFNVEVDGSKLNVTSTWNLASPLLSVNVDGTQRTVQCLSPDAGGNMSIQFLGTVYKVHIL
Yt PC      QKMRETYGDLSVLPTRSFLSPLETDEEIEVVIEQGKTLIIKLQAVGDLNKTGEREVYFDLNGEMRKIRV
Kp ODA     FPQPGLKFLENRHNPAAFEPVPQAEAAQPVAKAEKPAASGVYTVEVEGKAFVVKVSDGGDVSQLTAAAPA
Ps TC                          MKLKVTVNGTAYDVDVDVDKSHENPMGTILFGGG

Wh ACC     AGTRLLINGRTCLLQKEHDPSRLLADTPCKLLRFLVADGSHVVADTPYAEVEAMKM.......... 840
Rt ACC     DRYRITIGNKTCVFEKENDPSVMRSPSVMRSPSAGKLIQYIVEDGGHVFAGQCYAEIEVMKMVMTLTAVESGCIHY
Ch ACC     DRYRITIGNKTCVFEKENDPSILRSPSAGKLIQYVVEDGGHVFAGQCFAEIEVMKMVMTLAGESGCIHY
Yt ACC     AATRLSVDSMTTLLEVENDPTQLRTPSPGKLVKFLVENGEHIIKGQPYAEIEVMKMQMPLVSQENGIVQL
An ACC     QPGAKIIDQKLAEVASPMVGTFYRAPAPGE--AVFVEVGDRIRQGQTVCIIEAMKM..........
Ec ACC     MEAPAAAEISGHIVRSPMVGTFYRTPSPDA--KAFIEVGQKVNVGDTLCIVEAMKMMNQIEADKSGTVKA
Hm PCCA    TRLAAELNKFMLEKVTEDTSSVLRSPMPGVVAVSVKPGDAVAEGQEICVIEAMKMQNSMTAGKTGTVKS
Rt PCCA    TKLAAWLNKFMLEKVPKDTSSVLRSPKPGVVAVSVKPGDMVAEGQEICVIEAMKMQNSMTAGKMGKVKL
Yt PC      ADRSQKVETVTKSKADMHDPLHIGAPMAGVIVEVKVHKGSLIKGQPVAVLSAMKMEMIISSPSDGQVKE
Kp ODA     PAPAPASAPAAAAPAGAGTPVTAPLAGTIWKVLASEGQTVAAGEVLLILEAMKMETEIRAAQAGTVRG
Ps TC      TGGAPAPRAAGGAGAGAGAGEGEIPAPLAGTVSKILVKEGDTVKAGQTVLVLEAMKMETEINAPTDGKVEK
                                         *      *       * ***
```

FIG. 3F

```
Wh ACC    ................VKRPGAALDPGCVIAKMALDNPSKVQQAELHTGSLPQIQSTALRGEKLHRIF
Rt ACC                    VKRPGAVLDPGCVIAKLQLDDPSRVQQAELHTGTLPQIQSTALRGEKLHRIF
Ch ACC
Yt ACC                    LKQPGSTIVAGDIMAIMTLDDPSKVKHALPFEGMLPDFGSPVIEGTKPAYKF
An ACC    ................
Ec ACC                    ILVESGQPVEFDEPLVVIE
Hm PCCA                   VHCQAGDTVGEGDLLVELE
Rt PCCA                   VHCKAGDTVGEGDLLVELE
Yt PC                     VFVSDGENVDSSDLLVLLEDQVPVETKA
Kp ODA                    IAVKAGDAVAVGDTLMTLA
PS TC                     VLVKERDAVQGGQGLIKIG
                          ------------------
```

FIG. 3G

```
GTGATGATCAAGGCATCATGGGGTGTGGGGTGGTAAAGGAAATAAGGAAGGTACATAATGATGAGGTCAGAGCATTGTTTAAGCAAGTG    90
 V  M  I  K  A  S  W  G  G  G  G  K  G  I  R  K  V  H  N  D  D  E  V  R  A  L  F  K  Q  V

CAAGGAGAAGTCCCCGGATGCGCCTATATTTATTATGAAGGTGGCATCTCAGAGTCGACATCTAGAGGTTCAATTGCTCTGTGACAAGCAT   180
 Q  G  E  V  P  G  S  P  I  F  I  M  K  V  A  S  Q  S  R  H  L  E  V  Q  L  L  C  D  K  H

GGCAACGTGGCAGCACTGCACAGTCGAGACTGTAGTGTTCAAAGAAGGCATCAAAAGATCATTGAGGAGGACCAATTACAGTTGCTCCT    270
 G  N  V  A  A  L  H  S  R  D  C  S  V  Q  R  R  H  Q  K  I  I  E  E  G  P  I  T  V  A  P

CCAGAAACAATTAAAGAGCTTGAGCAGGCGGCCAAGGCGACTAGCTAAATGTGTGCAATATCAGGTGCTGCTACAGTGGAATATCTGTAC    360
 P  E  T  I  K  E  L  E  Q  A  A  R  R  L  A  K  C  V  Q  Y  Q  G  A  A  T  V  E  Y  L  Y

AGCATGGAAACAGGCGAATACTATTTCCTGGAGCTTAATCCAAGGTTGCAGGTAGAACACCCTGTGACCGAATGCATTGCTGAAATAAAC    450
 S  M  E  T  G  E  Y  Y  F  L  E  L  N  P  R  L  Q  V  E  H  P  V  T  E  W  I  A  E  I  N
                                  C
                                  T

TTACCTGCATCTCAAGTTGTAGTAGGAATGGGCATACCACTCTACAACATTCCAGAGATCAGAGCTTTATGGAATAGAACATGGAGGT    540
 L  P  A  S  Q  V  V  V  G  M  G  I  P  L  Y  N  I  P  E  I  R  R  F  Y  G  I  E  H  G  G
          C                                                    G
          C                                                    G

GGCTATCATGCTTGGAAGGAAATATCAGCTGTTGCAACTAAATTTGATTTGGACAAAGCACAGTCTGTAAAGCCAAAAGGTCATTGTGTA    630
 G  Y  H  A  W  K  E  I  S  A  V  A  T  K  F  D  L  D  K  A  Q  S  V  K  P  K  G  H  C  V
```

FIG. 6A

```
                                     A            G                                               720
                                     A            G
GCAGTTAGAGTTACTAGCGGAGGATCCAGATGATGATGGGTTTAAGCCTACCAGTGGAAGAGTAGAAGAGCTGAACTTTAAAAGTAAACCCAAT
 A  V  R  V  T  S  E  D  P  D  D  D  G  F  K  P  T  S  G  R  V  E  E  L  N  F  K  S  K  P  N
        C            G          C                                                      C
        T            A          T                                                      T
                                                                                                  810
                                                                          S
GTTTGGGCCTATTTCTCCGTTAAGTCCGGAGGTGCAATTCACGAGTTCTCTGATTCCCAGTTGGTCATGTTTTTGCTTTTGGGGAATCT
 V  W  A  Y  F  S  V  K  S  G  G  A  I  H  E  F  S  D  S  Q  F  G  H  V  F  A  F  G  E  S
                     R
 T
 A
                                            A                                   T   C            900
                                            A                                   A   T
AGGTCATTGGCAATAGCCAATATGGTACTTGGGTTAAAAGAGATCCAAATTCGTGGAGAGATACGCACTAATGTTGACTACACTGTGGAT
 R  S  L  A  I  A  N  M  V  L  G  L  K  E  I  Q  I  R  G  E  I  R  T  N  V  D  Y  T  V  D
                              K
                                                                                                  990
CTCTTGAATGCTGCAGAGTACCGAGAAAATATGATTCACACTGGTTGGCTAGACAGCAGAATAGCTATGCGCGTTAGAGCAGAGAGAGGCCC
 L  L  N  A  A  E  Y  R  E  N  M  I  H  T  G  W  L  D  S  R  I  A  M  R  V  R  A  E  R  P
                                                                                                 1080
CCATGGTACCTTTCAGTTGTTGGTGGAGCTCTATATGAAGCATCAAGCAGCAGGAGCTGAGTGTTGTAACCGATTATGTTGGTTATCTCAGT
 P  W  Y  L  S  V  V  G  G  A  L  Y  E  A  S  S  S  R  S  S  S  S  V  V  T  D  Y  Y  V  G  Y  L  S
```

FIG. 6B

```
                                                                    C
                                                                    T
AAAGGTCAAATATACCACCAAAGCACATCTCTCTTGTCAATTTGACTGTAACACTGAATATAGATGGGAGCAAATATACGATTGAGACAGTA 1170
 K  G  Q  I  P  P  K  H  I  S  L  V  N  L  T  V  T  L  N  I  D  G  S  K  Y  T  I  E  T  V
       A             CG                          C
                                                                  CG
                                                                   T
CGAGGTGGACCCCGTAGCTACAAATTAAGAATTAATGAATCAGAGGTTGAGGCAGAGATACATTTCCTGCGAGATGGCGGACTCTTAATG 1260
 R  G  G  P  R  S  Y  K  L  R  I  N  E  S  E  V  E  A  E  I  H  F  L  R  D  G  G  L  L  M
                                                      S                                    P
                                                      G
                                                      T
CAGTTGGATGGAAACAGTCATGTAATTTACGCCGAGACAGAAGCTGCTGGCACGGCGCCTTCTAATCAATGGGAGAACATGCTTATTACAG 1350
 Q  L  D  G  N  S  H  V  I  Y  A  E  T  E  A  A  G  T  R  L  L  L  I  N  G  R  T  C  L  L  Q
       T                                                 A        G
       C                                                 A        G
                       S                                                     S
AAAGAGCACGATCCTTCCAGGTTGTTGGCTGATACACCGTGCAAACTTCTTCGGTTTTGGTCGCGGATGGTTCTCATGGTTGCTGAT 1440
 K  E  H  D  P  S  R  L  L  A  D  T  P  C  K  L  L  R  F  L  V  A  D  G  S  H  V  V  A  D
             T                                                  T
             T                                                  T
ACGCCATATGCCGAGGTGGAGGCCATGAAAATG
 T  P  Y  A  E  V  E  A  M  K  M

FIG. 6C
```

```
TCTAGACTTTAACGAGATTCGTCAACTGCTGACAACTATTGCACAAACAGATATCGGGAAGTAACGCTCAAAGTGATGATTTTGAACT      90
 L  D  F  N  E  I  R  Q  L  L  T  T  I  A  Q  T  D  I  A  E  V  T  L  K  S  D  D  F  E  L

AACGGTGCGTAAAGCTGTTGGTGTGAATAATAGTGTTGTGCCGGTTGTGACAGCACCCTTGAGTGGTGTGGTAGGTTCGGGATTGCCATC     180
 T  V  R  K  A  V  G  V  N  N  S  V  V  P  V  V  T  A  P  L  S  G  V  V  G  S  G  L  P  S

GGCTATACGGATTGTAGCCCCATGCTGCCCCCATCTCCAGAGAGCCGGGAACAAGCCGTGCTGATCATGCTGTCACGAGTTCTGG         270
 A  I  P  I  V  A  H  A  A  P  S  P  E  P  G  T  S  R  A  A  D  H  A  V  T  S  S  G

CTCACAGCCAGGAGCAAAAATCATTGACCAAAAATTAGCAGAAGTGGCTTCCCCAATGGTGGGAACATTTTACCGCGCTCCTGCACCAGG     360
 S  Q  P  G  A  K  I  I  D  Q  K  L  A  E  V  A  S  S  P  M  V  G  T  F  Y  R  A  P  A  P  G

TGAAGCGGTATTTGTGGAAGTCGGCGATCGCATCCGTCAAGGTCAAACCGTCTGCATCATCGAAGCGATGAAAATG
 E  A  V  F  V  E  V  G  D  R  I  R  Q  G  Q  T  V  C  I  I  E  A  M  K  M
```

FIG. 8

SEQUENCE LISTING ( 1 ) GENERAL INFORMATION:

( i i i ) NUMBER OF SEQUENCES: 116

( 2 ) INFORMATION FOR SEQ ID NO:1:

( i ) SEQUENCE CHARACTERISTICS:
        ( A ) LENGTH: 3065 base pairs
        ( B ) TYPE: Nucleic acid
        ( C ) STRANDEDNESS: Single
        ( D ) TOPOLOGY: Linear ( i i ) MOLECULE TYPE: Oligonucleotide ( x i ) SEQUENCE DESCRIPTION: SEQ ID NO:1:

```
AAGCTTTTAT  ATTTTGCCAT  TTCTAGAACT  TAGCTGCATC  GGCCCCAAGT  ATTTTGTCAA    60

ATATGGCGAA  AAGACTTCAT  AAATCAAGGT  TAAAGGTTGA  CCGTGATGCC  AAAACAGGTA   120

ATGGCGACCC  CAGAAAGGCC  CATCCACGCC  AAAACCTAAT  TGCAAGGCCT  CTGAATTTCC   180

GTAATAAATA  CCCCGCACAT  CCCGATACAA  CTCCGTGCGA  AGACGAGCTA  GACTTGCCCA   240

AATTGGTAAT  GAACGGTTTT  GCAAATACTC  GTCTACATGG  CTGGCTTCCC  ACCATGAGGT   300

TGCATAGGCG  AGTCGTTGGC  CAGAGCGTGT  ACGTAGCCAT  ACCTGTCGCC  GCAGTCTTGG   360

CGCTGGAACA  GATTGGATTA  AATCCGGCGC  ACTATCTAAA  TCCAAACCAA  TCAATGACAT   420

ATCAATGACA  TCGACTTCTG  TTGGCTCACC  AGTAAGTAAT  TCTAAATGCC  TTGTGGGTGA   480
```

-continued

| | | | | | |
|---|---|---|---|---|---|
| GCCATCACCT | AAGAGTAGTA | GTTGCCACGC | TGGAGCCAGC | TGAGTGTGAG | GCAAACTATG | 540 |
| TTTAATTACT | TCTTCCCCAC | CTTGCCAAAT | AGGAGTGAGG | CGATGCCATC | CGGCTGGCAG | 600 |
| TGTTGAGTTG | TTGCTTGGAG | TAAAAGTGGC | AGTCAATGTT | CTTTACAAAA | GTTCACCTAT | 660 |
| TTATATCAAA | GCATAAAAAA | TTAATTAGTT | GTCAGTTGTC | ATTGGTTATT | CTTCTTTGCT | 720 |
| CCCCCTGCCC | CCTACTTCCC | TCCTCTGCCC | AATAATTAGA | AAGGTCAGGA | GTCAAAAACT | 780 |
| TATCACTTTT | GACCACTGAC | CTTTCACAAT | TGACTATAGT | CACTAAAAAA | TGCGGATGGC | 840 |
| GAGACTCGAA | CTCGCAAGGC | AAAGCCACAC | GCACCTCAAG | CGTGCGCGTA | TACCAATTCC | 900 |
| GCCACATCCG | CACGGGTTGT | ACAAGAAGAT | ATACTAGCAC | AAAAAAATTG | CATAAACAA | 960 |
| GGTAAAACTA | TATTTGCCAA | ACTTTATGGA | AAATTTATCT | TGCTAAATAT | ACAAATTTCC | 1020 |
| CGAAGAGGAT | ACGAGACTAA | CAGAAATGTA | GTATCGCCAC | AAGTGATATT | AAAGGGGTA | 1080 |
| TGGGGGTTTT | CTTCCCTTAC | ACCCTTAAAC | CCTCACACCC | CACCTCCATG | AAAAATCTTG | 1140 |
| TTGGTAAGTC | CGTTTCCTGC | AATTTATTTA | AAGATGAGCC | TGGGGTATCT | CCTGTCATAA | 1200 |
| TTTGAGATGA | AGCGATGCCT | AAGGCGGCTA | CGCTACGCGC | TAAAAGCAAC | TTGGATGGGA | 1260 |
| GACAATTTCT | ATCTGCTGGT | ACTGATACTG | ATATCGAAAA | CTAGAAAATG | AAGTTTGACA | 1320 |
| AAATATTAAT | TGCCAATCGG | GGAGAAATAG | CGCTGCGCAT | TCTCCGCGCC | TGTGAGGAAA | 1380 |
| TGGGGATTGC | GACGATCGCA | GTTCATTCGA | CTGTTGACCG | GAATGCTCTT | CATGTCCAAC | 1440 |
| TTGCTGACGA | AGCGGTTTGT | ATTGGCGAAC | CTGCTAGCGC | TAAAAGTTAT | TTGAATATTC | 1500 |
| CCAATATTAT | TGCTGCGGCT | TTAACGCGCA | ATGCCAGTGC | TATTCATCCT | GGGTATGGCT | 1560 |
| TTTTATCTGA | AAATGCCAAA | TTTGCGGAAA | TCTGTGCTGA | CCATCACATT | GCATTCATTG | 1620 |
| GCCCCACCCC | AGAAGCTATC | CGCCTCATGG | GGGACAAATC | CACTGCCAAG | GAAACCATGC | 1680 |
| AAAAAGCTGG | TGTACCGACA | GTACCGGGTA | GTGAAGGTTT | GGTAGAGACA | GAGCAAGAAG | 1740 |
| GATTAGAACT | GGCGAAAGAT | ATTGGCTACC | CAGTGATGAT | CAAAGCCACG | GCTGGTGGTG | 1800 |
| GCGGCCGGGG | TATGCGACTG | GTGCGATCGC | CAGATGAATT | TGTCAAACTG | TTCTTAGCCG | 1860 |
| CCCAAGGTGA | AGCTGGTGCA | GCCTTTGGTA | ATGCTGGCGT | TTATATAGAA | AAATTTATTG | 1920 |
| AACGTCCGCG | CCACATTGAA | TTTCAAATTT | TGGCTGATAA | TTACGGCAAT | GTGATTCACT | 1980 |
| TGGGTGAGAG | GGATTGCTCA | ATTCAGCGTC | GTAACCAAAA | GTTACTAGAA | GAAGCCCCA | 2040 |
| GCCCAGCCTT | GGACTCAGAC | CTAAGGGAAA | AAATGGGACA | AGCGGCGGTG | AAAGCGGCTC | 2100 |
| AGTTTATCAA | TTACGCCGGG | GCAGGTACTA | TCGAGTTTTT | GCTAGATAGA | TCCGGTCAGT | 2160 |
| TTTACTTTAT | GGAGATGAAC | ACCCGGATTC | AAGTAGAACA | TCCCGTAACT | GAGATGGTTA | 2220 |
| CTGGAGTGGA | TTTATTGGTT | GAGCAAATCA | GAATTGCCCA | AGGGGAAAGA | CTTAGACTAA | 2280 |
| CTCAAGACCA | AGTAGTTTTA | CGCGGTCATG | CGATCGAATG | TCGCATCAAT | GCCGAAGACC | 2340 |
| CAGACCACGA | TTTCCGCCCA | GCACCCGGAC | GCATTAGCGG | TTATCTTCCC | CCTGGCGGCC | 2400 |
| CTGGCGTGCG | GATTGACTCC | CACGTTTACA | CGGATTACCA | AATTCCGCCC | TACTACGATT | 2460 |
| CCTTAATTGG | TAAATTGATC | GTTTGGGGCC | CTGATCGCGC | TACTGCTATT | AACCGCATGA | 2520 |
| AACGCGCCCT | CAGGGAATGC | GCCATCACTG | GATTACCTAC | AACCATTGGG | TTCATCAAA | 2580 |
| GAATTATGGA | AAATCCCCAA | TTTTTACAAG | GTAATGTGTC | TACTAGTTTT | GTGCAGGAGA | 2640 |
| TGAATAAATA | GGGTAATGGG | TAATGGGTAA | TGGGTAATAG | AGTTTCAATC | ACCAATTACC | 2700 |
| AATTCCCTAA | CTCATCCGTG | CCAACATCGT | CAGTAATCCT | TGCTGGCCTA | GAAGAACTTC | 2760 |
| TCGCAACAGG | CTAAAAATAC | CAACACACAC | AATGGGGGTG | ATATCAACAC | CACCTATTGG | 2820 |
| TGGGATGATT | TTTCGCAAGG | GAATGAGAAA | TGGTTCAGTC | GGCCAAGCAA | TTAAGTTGAA | 2880 |

-continued

```
GGGCAAACGG TTCAGATCGA CTTGCGGATA CCAGGTCAGA ATGATACGGA AAATAAACAG        2940

AAATGTCATC ACTCCCAATA CAGGGCCAAG AATCCAAACG CTCAGGTTAA CACCAGTCAT        3000

CGATCTAAGC TACTATTTTG TGAATTTACA AAAAACTGCA AGCAAAAGCT GAAAATTTTA        3060

AGCTT                                                                    3065
```

( 2 ) INFORMATION FOR SEQ ID NO:2:

( i ) SEQUENCE CHARACTERISTICS:
        ( A ) LENGTH: 32 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:2:

```
Asp Glu Ala Met Pro Lys Ala Ala Thr Leu Arg Ala Lys Ser Asn Leu
                  5                   10                  15

Asp Gly Arg Gln Phe Leu Ser Ala Gly Thr Asp Thr Asp Ile Glu Asn
            20                  25                  30
```

( 2 ) INFORMATION FOR SEQ ID NO:3:

( i ) SEQUENCE CHARACTERISTICS:
        ( A ) LENGTH: 427 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:3:

```
Lys Met Lys Phe Asp Lys Ile Leu Ile Ala Asn Arg Gly Glu Ile Ala
                  5                   10                  15

Leu Arg Ile Leu Arg Ala Cys Glu Glu Met Gly Ile Ala Thr Ile Ala
            20                  25                  30

Val His Ser Thr Val Asp Arg Asn Ala Leu His Val Gln Leu Ala Asp
        35                  40                  45

Glu Ala Val Cys Ile Gly Glu Pro Ala Ser Ala Lys Ser Tyr Leu Asn
    50                  55                  60

Ile Pro Asn Ile Ile Ala Ala Ala Leu Thr Arg Asn Ala Ser Ala Ile
65                  70                  75                  80

His Pro Gly Tyr Gly Phe Leu Ser Glu Asn Ala Lys Phe Ala Glu Ile
                  85                  90                  95

Cys Ala Asp His His Ile Ala Phe Ile Gly Pro Thr Pro Glu Ala Ile
            100                 105                 110

Arg Leu Met Gly Asp Lys Ser Thr Ala Lys Glu Thr Met Gln Lys Ala
        115                 120                 125

Gly Val Pro Thr Val Pro Gly Ser Glu Gly Leu Val Glu Thr Glu Gln
    130                 135                 140

Glu Gly Leu Glu Leu Ala Lys Asp Ile Gly Tyr Pro Val Met Ile Lys
145                 150                 155                 160

Ala Thr Ala Gly Gly Gly Gly Arg Gly Met Arg Leu Val Arg Ser Pro
                  165                 170                 175

Asp Glu Phe Val Lys Leu Phe Leu Ala Ala Gln Gly Glu Ala Gly Ala
            180                 185                 190

Ala Phe Gly Asn Ala Gly Val Tyr Ile Glu Lys Phe Ile Glu Arg Pro
        195                 200                 205

Arg His Ile Glu Phe Gln Ile Leu Ala Asp Asn Tyr Gly Asn Val Ile
```

|     | 210 |     |     |     | 215 |     |     |     | 220 |     |     |     |     |
|-----|-----|-----|-----|-----|-----|-----|-----|-----|-----|-----|-----|-----|-----|

His Leu Glu Arg Asp Cys Ser Ile Gln Arg Arg Asn Gln Lys Leu Leu
225                     230                 235                         240

Glu Glu Ala Pro Ser Pro Ala Leu Asp Ser Asp Leu Arg Glu Lys Met
                245                 250                 255

Gly Gln Ala Ala Val Lys Ala Ala Gln Phe Ile Asn Tyr Ala Gly Ala
            260                 265                 270

Gly Thr Ile Glu Phe Leu Leu Asp Arg Ser Gly Gln Phe Gly Val Asp
        275                 280                 285

Leu Leu Val Glu Gln Ile Arg Ile Ala Gln Gly Glu Arg Leu Arg Leu
    290                 295                 300

Thr Gln Asp Gln Val Val Leu Arg Gly His Ala Ile Glu Cys Arg Ile
305                 310                 315                 320

Asn Ala Glu Asp Pro Asp His Asp Phe Arg Pro Ala Pro Gly Arg Ile
                325                 330                 335

Ser Gly Tyr Leu Pro Pro Gly Gly Pro Gly Val Arg Ile Asp Ser His
            340                 345                 350

Val Tyr Thr Asp Tyr Gln Ile Pro Pro Tyr Tyr Asp Ser Leu Ile Gly
        355                 360                 365

Lys Leu Ile Val Trp Gly Pro Asp Arg Ala Thr Ala Ile Asn Arg Met
    370                 375                 380

Lys Arg Ala Leu Arg Glu Cys Ala Ile Thr Gly Leu Pro Thr Thr Ile
385                 390                 395                 400

Gly Phe His Gln Arg Ile Met Glu Asn Pro Gln Phe Leu Gln Gly Asn
                405                 410                 415

Val Ser Thr Ser Phe Val Gln Glu Met Asn Lys
            420                 425

( 2 ) INFORMATION FOR SEQ ID NO:4:

( i ) SEQUENCE CHARACTERISTICS:
        ( A ) LENGTH: 36 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:4:

Trp Val Met Gly Asn Arg Val Ser Ile Thr Asn Tyr Gln Phe Pro Asn
                5                   10                  15

Ser Ser Val Pro Thr Ser Ser Val Ile Leu Ala Gly Leu Glu Glu Leu
            20                  25                  30

Leu Ala Thr Gly
            35

( 2 ) INFORMATION FOR SEQ ID NO:5:

( i ) SEQUENCE CHARACTERISTICS:
        ( A ) LENGTH: 1362 base pairs
        ( B ) TYPE: Nucleic acid
        ( C ) STRANDEDNESS: Single
        ( D ) TOPOLOGY: Linear ( i i ) MOLECULE TYPE: Oligonucleotide ( x i ) SEQUENCE DESCRIPTION: SEQ ID NO:5:

```
ATGCGTTTCA ACAAGATCCT GATCGCCAAT CGCGGCGAAA TCGCCCTGCG CATTCTCCGC        60

ACTTGTCAAG AACTCGGGAT CGGCACGATC GCCGTTCACT CCACTGTGGA TCGCAACGCG       120
```

-continued

| | | | | | |
|---|---|---|---|---|---|
| CTCCATGTGC | AGTTAGCGGA | CGAAGCGGTC | TGTATTGGCG | AAGCGGCCAG | CAGCAAAAGC | 180 |
| TATCTCAATA | TCCCCAACAT | CATTGCGGCG | GCCCTGACCC | CTAATGCCAG | CGCCATTCAC | 240 |
| CCCGGCTATG | GCTTCTTGGC | GGAGAATGCC | CGCTTTGCAG | AAATCTGCGC | CGATCACCAT | 300 |
| CTCACCTTTA | TTGGCCCCAG | CCCCGATTCG | ATTCGAGCCA | TGGGCGATAA | ATCCACCGCT | 360 |
| AAGGAAACAA | TGCAGCGGGT | CGGCGTTCCG | ACGATTCCGG | GCAGTGACGG | TCTGCTGACG | 420 |
| GATGTTGATT | CGGCTGCCAA | AGTTGCTGCC | GAGATCGGCT | ATCCCGTCAT | GATCAAAGCG | 480 |
| ACGGCGGGGG | GCGGTGGTCG | CGGTATGCGG | CTGGTGCGTG | ACCCTGCAGA | TCTGGAAAAA | 540 |
| CTGTTCCTTG | CTGCCCAAGG | AGAAGCCGAG | GCAGCTTTTG | GGAATCCAGG | ACTGTATCTC | 600 |
| GAAAAATTTA | TCGATCGCCC | ACGCCACGTT | GAATTTCAGA | TCTTGGCCGA | TGCCTACGGC | 660 |
| AATGTAGTGC | ATCTAGGCGA | GCGCGATTGC | TCCATTCAAC | GTCGTCACCA | AAAGCTGCTC | 720 |
| GAAGAAGCCC | CCAGTCCGGC | GCTATCGGCA | GACCTGCGGC | AGAAAATGGG | CGATGCCGCC | 780 |
| GTCAAAGTCG | CTCAAGCGAT | CGGCTACATC | GGTGCCGGCA | CCGTGGAGTT | TCTGGTCGAT | 840 |
| GCGACCGGCA | ACTTCTACTT | CATGGAGATG | AATACCCGCA | TCCAAGTCGA | GCATCCAGTC | 900 |
| ACAGAAATGA | TTACGGGACT | GGACTTGATT | GCGGAGCAGA | TTCGGATTGC | CCAAGGCGAA | 960 |
| GCGCTGCGCT | TCCGGCAAGC | CGATATTCAA | CTGCGCGGCC | ATGCGATCGA | ATGCCGTATC | 1020 |
| AATGCGGAAG | ATCCGGAATA | CAATTTCCGG | CCGAATCCTG | GCCGCATTAC | AGGCTATTTA | 1080 |
| CCGCCCGGCG | GCCCCGGCGT | TCGTGTCGAT | TCCCATGTTT | ATACCGACTA | CGAAATTCCG | 1140 |
| CCCTATTACG | ATTCGCTGAT | TGGCAAATTG | ATTGTCTGGG | GTGCAACACG | GGAAGAGGCG | 1200 |
| ATCGCGCGGA | TGCAGCGTGC | TCTGCGGGAA | TGCGCCATCA | CCGGCTTGCC | GACGACCCTT | 1260 |
| AGTTTCCATC | AGCTGATGTT | GCAGATGCCT | GAGTTCCTGC | GCGGGGAACT | CTATACCAAC | 1320 |
| TTTGTTGAGC | AGGTGATGCT | ACCTCGGATC | CTCAAGTCCT | AG | | 1362 |

( 2 ) INFORMATION FOR SEQ ID NO:6:

( i ) SEQUENCE CHARACTERISTICS:
      ( A ) LENGTH: 453 amino acids
      ( B ) TYPE: Amino acid
      ( C ) STRANDEDNESS: Single
      ( D ) TOPOLOGY: Linear ( i i ) MOLECULE TYPE: Peptide ( x i ) SEQUENCE DESCRIPTION: SEQ ID NO:6:

Met Arg Phe Asn Lys Ile Leu Ile Ala Asn Arg Gly Glu Ile Ala Leu
              5                  10                  15

Arg Ile Leu Arg Thr Cys Glu Glu Leu Gly Ile Gly Thr Ile Ala Val
             20                  25                  30

His Ser Thr Val Asp Arg Asn Ala Leu His Val Gln Leu Ala Asp Glu
         35                  40                  45

Ala Val Cys Ile Gly Glu Ala Ala Ser Ser Lys Ser Tyr Leu Asn Ile
     50                  55                  60

Pro Asn Ile Ile Ala Ala Ala Leu Thr Arg Asn Ala Ser Ala Ile His
 65                  70                  75                  80

Pro Gly Tyr Gly Phe Leu Ala Glu Asn Ala Arg Phe Ala Glu Ile Cys
                 85                  90                  95

Ala Asp His His Leu Thr Phe Ile Gly Pro Ser Pro Asp Ser Ile Arg
            100                 105                 110

Ala Met Gly Asp Lys Ser Thr Ala Lys Glu Thr Met Gln Arg Val Gly
        115                 120                 125

Val Pro Thr Ile Pro Gly Ser Asp Gly Leu Leu Thr Asp Val Asp Ser

-continued

|   |   |   |   |   |   |   |   |   |   |   |   |   |   |   |
|---|---|---|---|---|---|---|---|---|---|---|---|---|---|---|
|   |   |   |   | 130 |   |   |   | 135 |   |   |   | 140 |   |   |
| Ala | Ala | Lys | Val | Ala | Ala | Glu | Ile | Gly | Tyr | Pro | Val | Met | Ile | Lys | Ala |
| 145 |   |   |   |   | 150 |   |   |   | 155 |   |   |   |   |   | 160 |
| Thr | Ala | Gly | Gly | Gly | Gly | Arg | Gly | Met | Arg | Leu | Val | Arg | Glu | Pro | Ala |
|   |   |   |   | 165 |   |   |   | 170 |   |   |   | 175 |   |   |
| Asp | Leu | Glu | Lys | Leu | Phe | Leu | Ala | Ala | Gln | Gly | Glu | Ala | Ala | Ala | Ala |
|   |   |   | 180 |   |   |   |   | 185 |   |   |   |   | 190 |   |   |
| Phe | Gly | Asn | Pro | Gly | Leu | Tyr | Leu | Glu | Lys | Phe | Ile | Asp | Arg | Pro | Arg |
|   |   | 195 |   |   |   |   | 200 |   |   |   |   | 205 |   |   |   |
| His | Val | Glu | Phe | Gln | Ile | Leu | Ala | Asp | Ala | Tyr | Gly | Asn | Val | Val | Glu |
|   |   | 210 |   |   |   | 215 |   |   |   |   | 220 |   |   |   |   |
| Leu | Gly | Glu | Arg | Asp | Cys | Ser | Ile | Gln | Arg | Arg | His | Gln | Lys | Leu | Leu |
| 225 |   |   |   |   | 230 |   |   |   |   | 235 |   |   |   |   | 240 |
| Glu | Glu | Ala | Pro | Ser | Pro | Ala | Leu | Ser | Ala | Asp | Leu | Arg | Gln | Lys | Met |
|   |   |   |   | 245 |   |   |   |   | 250 |   |   |   |   | 255 |   |
| Gly | Asp | Ala | Ala | Val | Lys | Val | Ala | Gln | Ala | Ile | Gly | Tyr | Ile | Gly | Ala |
|   |   |   |   | 260 |   |   |   |   | 265 |   |   |   |   | 270 |   |
| Gly | Thr | Val | Glu | Phe | Leu | Val | Asp | Ala | Thr | Gly | Asn | Phe | Tyr | Phe | Met |
|   |   |   | 275 |   |   |   |   | 280 |   |   |   |   | 285 |   |   |
| Glu | Met | Asn | Thr | Arg | Ile | Gln | Val | Glu | His | Pro | Val | Thr | Glu | Met | Ile |
|   |   |   | 290 |   |   |   | 295 |   |   |   |   | 300 |   |   |   |
| Thr | Gly | Leu | Asp | Leu | Ile | Ala | Glu | Gln | Ile | Arg | Ile | Ala | Gln | Gly | Glu |
| 305 |   |   |   |   | 310 |   |   |   |   | 315 |   |   |   |   | 320 |
| Ala | Leu | Arg | Phe | Arg | Gln | Ala | Asp | Ile | Gln | Leu | Arg | Gly | His | Ala | Ile |
|   |   |   |   | 325 |   |   |   |   | 330 |   |   |   |   | 335 |   |
| Glu | Cys | Arg | Ile | Asn | Ala | Glu | Asp | Pro | Glu | Tyr | Asn | Phe | Arg | Pro | Asn |
|   |   |   |   | 340 |   |   |   |   | 345 |   |   |   |   | 350 |   |
| Pro | Gly | Arg | Ile | Thr | Gly | Tyr | Leu | Pro | Pro | Gly | Gly | Pro | Gly | Val | Arg |
|   |   |   | 355 |   |   |   |   | 360 |   |   |   |   | 265 |   |   |
| Val | Asp | Ser | His | Val | Tyr | Thr | Asp | Tyr | Glu | Ile | Pro | Pro | Tyr | Tyr | Asp |
|   |   |   | 370 |   |   |   |   | 375 |   |   |   |   | 380 |   |   |
| Ser | Leu | Ile | Gly | Lys | Leu | Ile | Val | Trp | Gly | Ala | Thr | Arg | Glu | Glu | Ala |
| 385 |   |   |   |   | 390 |   |   |   |   | 395 |   |   |   |   | 400 |
| Ile | Ala | Arg | Met | Gln | Arg | Ala | Leu | Arg | Glu | Gly | Ala | Ile | Thr | Gly | Leu |
|   |   |   |   | 405 |   |   |   |   | 410 |   |   |   |   | 415 |   |
| Pro | Thr | Thr | Leu | Ser | Phe | His | Gln | Leu | Met | Leu | Gln | Met | Pro | Glu | Phe |
|   |   |   | 420 |   |   |   |   | 425 |   |   |   |   | 430 |   |   |
| Leu | Arg | Gly | Glu | Leu | Tyr | Thr | Asn | Phe | Val | Glu | Gln | Val | Met | Leu | Pro |
|   |   |   | 435 |   |   |   |   | 440 |   |   |   |   | 445 |   |   |
| Arg | Ile | Leu | Lys | Ser |   |   |   |   |   |   |   |   |   |   |   |
|   |   |   | 450 |   |   |   |   |   |   |   |   |   |   |   |   |

( 2 ) INFORMATION FOR SEQ ID NO:7:

( i ) SEQUENCE CHARACTERISTICS:
        ( A ) LENGTH: 34 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:7:

| Met | Asp | Glu | Pro | Ser | Pro | Leu | Ala | Lys | Thr | Leu | Glu | Leu | Asn | Gln | His |
|---|---|---|---|---|---|---|---|---|---|---|---|---|---|---|---|
|   |   |   |   | 5 |   |   |   |   | 10 |   |   |   |   | 15 |   |
| Ser | Arg | Phe | Ile | Ile | Gly | Ser | Val | Ser | Glu | Asp | Asn | Ser | Glu | Asp | Glu |
|   |   |   | 20 |   |   |   |   | 25 |   |   |   |   | 30 |   |   |

Ile Ser (2) INFORMATION FOR SEQ ID NO:8:

(i) SEQUENCE CHARACTERISTICS:
    (A) LENGTH: 187 amino acids
    (B) TYPE: Amino acid
    (C) STRANDEDNESS: Single
    (D) TOPOLOGY: Linear (ii) MOLECULE TYPE: Peptide (xi) SEQUENCE DESCRIPTION: SEQ ID NO:8:

```
Asn Leu Val Lys Leu Asp Leu Glu Glu Lys Glu Gly Ser Leu Ser Pro
              5                  10                  15
Ala Ser Val Ser Ser Asp Thr Leu Ser Asp Leu Gly Ile Ser Ala Leu
             20                  25                  30
Gln Asp Gly Leu Ala Phe His Met Arg Ser Ser Met Ser Gly Leu His
         35                  40                  45
Leu Val Lys Gln Gly Arg Asp Arg Lys Lys Ile Asp Ser Gln Arg Asp
     50                  55                  60
Phe Thr Val Ala Ser Pro Ala Glu Phe Val Thr Arg Phe Gly Gly Asn
 65                  70                  75                  80
Lys Val Ile Glu Lys Val Leu Ile Ala Asn Asn Gly Ile Ala Ala Val
                 85                  90                  95
Lys Cys Met Arg Ser Ile Arg Arg Trp Ser Tyr Glu Met Phe Arg Asn
            100                 105                 110
Glu Arg Ala Ile Arg Phe Val Val Met Val Thr Pro Glu Asp Leu Lys
        115                 120                 125
Ala Asn Ala Glu Tyr Ile Lys Met Ala Asp His Tyr Val Pro Val Pro
    130                 135                 140
Gly Gly Ala Asn Asn Asn Asn Tyr Ala Asn Val Glu Leu Ile Leu Asp
145                 150                 155                 160
Ile Ala Lys Arg Ile Pro Val Gln Ala Val Trp Ala Gly Trp Gly His
                165                 170                 175
Ala Ser Glu Asn Pro Lys Leu Pro Glu Leu Leu
            180                 185
```

(2) INFORMATION FOR SEQ ID NO:9:

(i) SEQUENCE CHARACTERISTICS:
    (A) LENGTH: 122 amino acids
    (B) TYPE: Amino acid
    (C) STRANDEDNESS: Single
    (D) TOPOLOGY: Linear (ii) MOLECULE TYPE: Peptide (xi) SEQUENCE DESCRIPTION: SEQ ID NO:9:

```
Leu Lys Asn Gly Ile Ala Phe Met Gly Pro Pro Ser Gln Ala Met Trp
              5                  10                  15
Ala Leu Gly Asp Lys Ile Ala Ser Ser Ile Val Ala Gln Thr Ala Gly
             20                  25                  30
Ile Pro Thr Leu Pro Trp Ser Gly Ser Gly Leu Arg Val Asp Trp Gln
         35                  40                  45
Glu Asn Asp Phe Ser Lys Arg Ile Leu Asn Val Pro Gln Asp Leu Tyr
     40                  55                  60
Glu Lys Gly Tyr Val Lys Asp Val Asp Asp Gly Leu Lys Ala Ala Glu
 65                  70                  75                  80
```

```
Glu Val Gly Tyr Pro Val Met Ile Lys Ala Ser Glu Gly Gly Gly
                85                  90                  95
Lys Gly Ile Arg Lys Val Asn Asn Ala Asp Asp Phe Pro Asn Leu Phe
                100                 105                 110
Arg Gln Val Gln Ala Glu Val Pro Gly Ser
                115                 120
```

(2) INFORMATION FOR SEQ ID NO:10:

(i) SEQUENCE CHARACTERISTICS:
        (A) LENGTH: 86 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:10:

```
Pro Ile Phe Val Met Arg Leu Ala Lys Gln Ser Arg His Leu Glu Val
                5                   10                  15
Gln Ile Leu Ala Asp Gln Tyr Gly Asn Ala Ile Ser Leu Phe Gly Arg
                20                  25                  30
Asp Cys Ser Val Gln Arg Arg His Gln Lys Ile Ile Glu Glu Ala Pro
                35                  40                  45
Ala Ala Ile Ala Thr Pro Ala Val Phe Glu His Met Glu Gln Cys Ala
50                      55                  60
Val Lys Leu Ala Lys Met Val Gly Tyr Val Ser Ala Gly Thr Val Glu
65                      70                  75                  80
Tyr Leu Tyr Ser Gln Asp
                85
```

(2) INFORMATION FOR SEQ ID NO:11:

(i) SEQUENCE CHARACTERISTICS:
        (A) LENGTH: 70 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:11:

```
Gly Ser Phe Tyr Phe Leu Glu Leu Asn Pro Arg Leu Gln Val Glu His
                5                   10                  15
Pro Cys Thr Glu Met Val Ala Asp Val Asn Leu Pro Ala Ala Gln Leu
                20                  25                  30
Gln Ile Ala Met Gly Ile Pro Leu Phe Arg Ile Lys Asp Ile Arg Met
                35                  40                  45
Met Tyr Gly Val Ser Pro Trp Gly Asp Ala Pro Ile Asp Phe Glu Asn
        50                  55                  60
Ser Ala His Val Pro Cys
65                  70
```

(2) INFORMATION FOR SEQ ID NO:12:

(i) SEQUENCE CHARACTERISTICS:
        (A) LENGTH: 20 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:12:

Pro Arg Gly His Val Ile Ala Ala Arg Ile Thr Ser Glu Asn Pro Asp
            5                   10                  15
Glu Gly Phe Lys
            20

( 2 ) INFORMATION FOR SEQ ID NO:13:

( i ) SEQUENCE CHARACTERISTICS:
                    ( A ) LENGTH: 21 amino acids
                    ( B ) TYPE: Amino acid
                    ( C ) STRANDEDNESS: Single
                    ( D ) TOPOLOGY: Linear ( i i ) MOLECULE TYPE: Peptide ( x i ) SEQUENCE DESCRIPTION: SEQ ID NO:13:

Pro Ser Ser Gly Thr Val Gln Glu Leu Asn Phe Arg Ser Asn Lys Asn
            5                   10                  15
Val Trp Gly Tyr Phe
            20

( 2 ) INFORMATION FOR SEQ ID NO:14:

( i ) SEQUENCE CHARACTERISTICS:
                    ( A ) LENGTH: 122 amino acids
                    ( B ) TYPE: Amino acid
                    ( C ) STRANDEDNESS: Single
                    ( D ) TOPOLOGY: Linear ( i i ) MOLECULE TYPE: Peptide ( x i ) SEQUENCE DESCRIPTION: SEQ ID NO:14:

Ser Val Ala Ala Ala Gly Gly Leu His Glu Phe Ala Asp Ser Gln Phe
                    5                   10                  15
Gly His Cys Phe Ser Trp Gly Glu Asn Arg Glu Glu Ala Ile Ser Asn
                    20                  25                  30
Met Val Val Ala Leu Lys Glu Leu Ser Ile Arg Gly Asp Phe Arg Thr
                    35                  40                  45
Thr Val Glu Tyr Leu Ile Lys Leu Leu Glu Thr Glu Ser Phe Gln Leu
        50                  55                  60
Asn Arg Ile Asp Thr Gly Trp Leu Asp Arg Leu Ile Ala Glu Lys Val
65                  70                  75                  80
Gln Ala Glu Arg Pro Asp Thr Met Leu Gly Val Val Cys Gly Ala Leu
                    85                  90                  95
His Val Ala Asp Val Asn Leu Arg Asn Ser Ile Ser Asn Phe Leu His
                    100                 105                 110
Ser Leu Glu Arg Gly Gln Val Leu Pro Ala
            115                 120

( 2 ) INFORMATION FOR SEQ ID NO:15:

( i ) SEQUENCE CHARACTERISTICS:
                    ( A ) LENGTH: 190 amino acids
                    ( B ) TYPE: Amino acid
                    ( C ) STRANDEDNESS: Single
                    ( D ) TOPOLOGY: Linear ( i i ) MOLECULE TYPE: Peptide ( x i ) SEQUENCE DESCRIPTION: SEQ ID NO:15:

His Thr Leu Leu Asn Thr Val Asp Val Glu Leu Ile Tyr Glu Gly Ile
                    5                   10                  15
Lys Tyr Val Leu Lys Val Thr Arg Gln Ser Pro Asn Ser Tyr Val Val

```
                  20                          25                          30
Ile  Met  Asn  Gly  Ser  Cys  Val  Glu  Val  Asp  Val  His  Arg  Leu  Ser  Asp
               35                       40                       45
Gly  Gly  Leu  Leu  Leu  Ser  Tyr  Asp  Gly  Ser  Ser  Tyr  Thr  Thr  Tyr  Met
     50                            55                       60
Lys  Glu  Glu  Val  Asp  Arg  Tyr  Arg  Ile  Thr  Ile  Gly  Asn  Lys  Thr  Cys
65                       70                       75                            80
Val  Phe  Glu  Lys  Glu  Asn  Asp  Pro  Ser  Val  Met  Arg  Ser  Pro  Ser  Ala
                    85                       90                       95
Gly  Lys  Leu  Ile  Gln  Tyr  Ile  Val  Glu  Asp  Gly  Gly  His  Val  Phe  Ala
                    100                      105                     110
Gly  Gln  Cys  Tyr  Ala  Glu  Ile  Glu  Val  Met  Lys  Met  Val  Met  Thr  Leu
               115                      120                     125
Thr  Ala  Val  Glu  Ser  Gly  Cys  Ile  His  Tyr  Val  Lys  Arg  Pro  Gly  Ala
     130                           135                     140
Ala  Leu  Asp  Pro  Gly  Cys  Val  Ile  Ala  Lys  Met  Gln  Leu  Asp  Asn  Pro
145                           150                     155                     160
Ser  Lys  Val  Gln  Gln  Ala  Glu  Leu  His  Thr  Gly  Ser  Leu  Pro  Gln  Ile
                    165                     170                          175
Gln  Ser  Thr  Ala  Leu  Arg  Gly  Glu  Lys  Leu  His  Arg  Ile  Phe
     180                           185                          190
```

( 2 ) INFORMATION FOR SEQ ID NO:16:

( i ) SEQUENCE CHARACTERISTICS:
        ( A ) LENGTH: 37 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:16:

```
Val  Met  Ile  Lys  Ala  Ser  Trp  Gly  Gly  Gly  Gly  Lys  Gly  Ile  Arg  Lys
                    5                        10                          15
Val  His  Asn  Asp  Asp  Glu  Val  Arg  Ala  Leu  Phe  Lys  Gln  Val  Gln  Gly
               20                       25                      30
Glu  Val  Pro  Gly  Ser
               35
```

( 2 ) INFORMATION FOR SEQ ID NO:17:

( i ) SEQUENCE CHARACTERISTICS:
        ( A ) LENGTH: 187 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:17:

```
Pro  Ile  Phe  Ile  Met  Lys  Val  Ala  Ser  Gln  Ser  Arg  His  Leu  Glu  Val
                    5                        10                          15
Gln  Leu  Leu  Cys  Asp  Lys  His  Gly  Asn  Val  Ala  Ala  Leu  His  Ser  Arg
               20                       25                      30
Asp  Cys  Ser  Val  Gln  Arg  Arg  His  Gln  Lys  Ile  Ile  Glu  Glu  Gly  Pro
          35                            40                      45
Ile  Thr  Val  Ala  Pro  Pro  Glu  Thr  Ile  Lys  Glu  Leu  Glu  Gln  Ala  Ala
     50                            55                      60
Arg  Arg  Leu  Ala  Lys  Cys  Val  Gln  Tyr  Gln  Gly  Ala  Ala  Thr  Val  Glu
```

|  | 65 | | | | 70 | | | | 75 | | | | 80 | |
|---|---|---|---|---|---|---|---|---|---|---|---|---|---|---|

Tyr Leu Tyr Ser Met Glu Thr Gly Glu Tyr Tyr Phe Leu Glu Leu Asn
                85                      90                      95

Pro Arg Leu Gln Val Glu His Pro Val Thr Glu Trp Ile Ala Glu Ile
                100                     105                 110

Asn Leu Pro Ala Ser Gln Val Val Gly Met Gly Ile Pro Leu Tyr
                115             120                     125

Asn Ile Pro Glu Ile Arg Arg Phe Tyr Gly Ile Glu His Gly Gly Gly
        130                 135                 140

Tyr His Ala Trp Lys Glu Ile Ser Ala Val Ala Thr Lys Phe Asp Leu
145             150                     155                     160

Asp Lys Ala Gln Ser Val Lys Pro Lys Gly His Cys Val Ala Val Arg
                165                 170                     175

Val Thr Ser Glu Asp Pro Asp Asp Gly Phe Lys
                180                 185

( 2 ) INFORMATION FOR SEQ ID NO:18:

( i ) SEQUENCE CHARACTERISTICS:
        ( A ) LENGTH: 21 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:18:

Pro Thr Ser Gly Arg Val Glu Glu Leu Asn Phe Lys Ser Lys Pro Asn
                5                   10                  15

Val Trp Ala Tyr Phe
                20

( 2 ) INFORMATION FOR SEQ ID NO:19:

( i ) SEQUENCE CHARACTERISTICS:
        ( A ) LENGTH: 122 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:19:

Ser Val Lys Ser Gly Gly Ala Ile His Glu Phe Ser Asp Ser Gln Phe
                5                   10                  15

Gly His Val Phe Ala Phe Gly Glu Ser Arg Ser Leu Ala Ile Ala Asn
                20                  25                  30

Met Val Leu Gly Leu Lys Glu Ile Gln Ile Arg Gly Glu Ile Arg Thr
                35                  40                  45

Asn Val Asp Tyr Thr Val Asp Leu Leu Asn Ala Ala Glu Tyr Arg Glu
        50                  55                  60

Asn Met Ile His Thr Gly Trp Leu Asp Ser Arg Ile Ala Met Arg Val
65              70                  75                      80

Arg Ala Glu Arg Pro Pro Trp Tyr Leu Ser Val Val Gly Gly Ala Leu
                85                  90                  95

Tyr Glu Ala Ser Ser Arg Ser Ser Ser Val Val Thr Asp Tyr Val Gly
                100                 105                 110

Tyr Leu Ser Lys Gly Gln Ile Pro Pro Lys
                110                 120

-continued ( 2 ) INFORMATION FOR SEQ ID NO:20:

( i ) SEQUENCE CHARACTERISTICS:
        ( A ) LENGTH: 124 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:20:

```
His Ile Ser Leu Val Asn Leu Thr Val Thr Leu Asn Ile Asp Gly Ser
                 5                  10                  15
Lys Tyr Thr Ile Glu Thr Val Arg Gly Pro Arg Ser Tyr Lys Leu
             20                  25                  30
Arg Ile Asn Glu Ser Glu Val Glu Ala Glu Ile His Phe Leu Arg Asp
             35                  40                  45
Gly Gly Leu Leu Met Gln Leu Asp Gly Asn Ser His Val Ile Tyr Ala
     50                  55                  60
Glu Thr Glu Ala Ala Gly Thr Arg Leu Leu Ile Asn Gly Arg Thr Cys
 65                  70                  75                  80
Leu Leu Gln Lys Glu His Asp Pro Ser Arg Leu Leu Ala Asp Thr Pro
                 85                  90                  95
Cys Lys Leu Leu Arg Phe Leu Val Ala Asp Gly Ser His Val Val Ala
                 100                 105                 110
Asp Thr Pro Tyr Ala Glu Val Glu Ala Met Lys Met
             115                 120
```

( 2 ) INFORMATION FOR SEQ ID NO:21:

( i ) SEQUENCE CHARACTERISTICS:
        ( A ) LENGTH: 222 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:21:

```
Met Glu Glu Ser Ser Gln Pro Ala Lys Pro Leu Glu Met Asn Pro His
                 5                  10                  15
Ser Arg Phe Ile Ile Gly Ser Val Ser Glu Asp Asn Ser Glu Asp Glu
             20                  25                  30
Thr Ser Ser Leu Val Lys Leu Asp Leu Leu Glu Glu Lys Glu Arg Ser
             35                  40                  45
Leu Ser Pro Val Ser Val Cys Ser Asp Ser Leu Ser Asp Leu Gly Leu
     50                  55                  60
Pro Ser Ala Gln Asp Gly Leu Ala Asn His Met Arg Pro Ser Met Ser
 65                  70                  75                  80
Gly Leu His Leu Val Lys Gln Gly Arg Asp Arg Lys Lys Val Asp Val
                 85                  90                  95
Gln Arg Asp Phe Thr Val Ala Ser Pro Ala Glu Phe Val Thr Arg Phe
             100                 105                 110
Gly Gly Asn Arg Val Ile Glu Lys Val Leu Ile Ala Asn Asn Gly Ile
             115                 120                 125
Ala Ala Val Lys Cys Met Arg Ser Ile Arg Arg Trp Ser Tyr Glu Met
     130                 135                 140
Phe Arg Asn Glu Arg Ala Ile Arg Phe Val Val Met Val Thr Pro Glu
 145                 150                 155                 160
Asp Leu Lys Ala Asn Ala Glu Tyr Ile Lys Met Ala Asp His Tyr Val
```

|     |     |     |     | 165 |     |     |     |     | 170 |     |     |     |     | 175 |     |
| --- | --- | --- | --- | --- | --- | --- | --- | --- | --- | --- | --- | --- | --- | --- | --- |
| Pro | Val | Pro | Gly | Gly | Pro | Asn | Asn | Asn | Asn | Tyr | Ala | Asn | Val | Glu | Leu |
|     |     |     | 180 |     |     |     | 185 |     |     |     |     |     | 190 |     |     |
| Ile | Leu | Asp | Ile | Ala | Lys | Arg | Ile | Pro | Val | Gln | Ala | Val | Trp | Ala | Gly |
|     |     |     | 195 |     |     |     | 200 |     |     |     |     | 205 |     |     |     |
| Trp | Gly | His | Ala | Ser | Glu | Asn | Pro | Lys | Leu | Pro | Glu | Leu | Leu |     |     |
|     |     |     | 210 |     |     |     | 215 |     |     |     |     | 220 |     |     |     |

( 2 ) INFORMATION FOR SEQ ID NO:22:

( i ) SEQUENCE CHARACTERISTICS:
        ( A ) LENGTH: 122 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:22:

| His | Lys | Asn | Gly | Ile | Ala | Phe | Met | Gly | Pro | Pro | Ser | Gln | Ala | Met | Trp |
| --- | --- | --- | --- | --- | --- | --- | --- | --- | --- | --- | --- | --- | --- | --- | --- |
|     |     |     |     | 5   |     |     |     |     | 10  |     |     |     |     | 15  |     |
| Ala | Leu | Gly | Asp | Lys | Ile | Ala | Ser | Ser | Ile | Val | Ala | Gln | Thr | Ala | Gly |
|     |     |     | 20  |     |     |     | 25  |     |     |     |     | 30  |     |     |     |
| Ile | Pro | Thr | Leu | Pro | Trp | Asn | Gly | Ser | Gly | Leu | Arg | Val | Asp | Trp | Gln |
|     |     |     | 35  |     |     |     | 40  |     |     |     |     | 45  |     |     |     |
| Glu | Asn | Asp | Leu | Gln | Lys | Arg | Ile | Leu | Asn | Val | Pro | Gln | Glu | Leu | Tyr |
|     | 50  |     |     |     |     | 55  |     |     |     |     | 60  |     |     |     |     |
| Glu | Lys | Gly | Tyr | Val | Lys | Asp | Ala | Asp | Asp | Gly | Leu | Arg | Ala | Ala | Glu |
| 65  |     |     |     | 70  |     |     |     |     | 75  |     |     |     |     | 80  |     |
| Glu | Val | Gly | Tyr | Pro | Val | Met | Ile | Lys | Ala | Ser | Glu | Gly | Gly | Gly | Gly |
|     |     |     |     | 85  |     |     |     |     | 90  |     |     |     |     | 95  |     |
| Lys | Gly | Ile | Arg | Lys | Val | Asn | Asn | Ala | Asp | Asp | Phe | Pro | Asn | Leu | Phe |
|     |     |     | 100 |     |     |     | 105 |     |     |     |     | 110 |     |     |     |
| Arg | Gln | Val | Gln | Ala | Glu | Val | Pro | Gly | Ser |     |     |     |     |     |     |
|     |     |     | 115 |     |     |     | 120 |     |     |     |     |     |     |     |     |

( 2 ) INFORMATION FOR SEQ ID NO:23:

( i ) SEQUENCE CHARACTERISTICS:
        ( A ) LENGTH: 95 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:23:

| Pro | Ile | Phe | Val | Met | Arg | Leu | Ala | Lys | Gln | Ser | Arg | His | Leu | Glu | Val |
| --- | --- | --- | --- | --- | --- | --- | --- | --- | --- | --- | --- | --- | --- | --- | --- |
|     |     |     |     | 5   |     |     |     |     | 10  |     |     |     |     | 15  |     |
| Gln | Ile | Leu | Ala | Asp | Gln | Tyr | Gly | Asn | Ala | Ile | Ser | Leu | Phe | Gly | Arg |
|     |     |     | 20  |     |     |     | 25  |     |     |     |     | 30  |     |     |     |
| Asp | Cys | Ser | Val | Gln | Arg | Arg | His | Gln | Lys | Ile | Ile | Glu | Glu | Ala | Gly |
|     |     | 35  |     |     |     |     | 40  |     |     |     |     | 45  |     |     |     |
| Leu | Arg | Ala | Ala | Glu | Glu | Val | Gly | Tyr | Pro | Val | Met | Ile | Lys | Ala | Ser |
|     | 50  |     |     |     |     | 55  |     |     |     |     | 60  |     |     |     |     |
| Glu | Gly | Gly | Gly | Gly | Lys | Gly | Ile | Arg | Lys | Val | Asn | Asn | Ala | Asp | Asp |
| 65  |     |     |     | 70  |     |     |     |     | 75  |     |     |     |     | 80  |     |
| Phe | Pro | Asn | Leu | Phe | Arg | Gln | Val | Gln | Ala | Glu | Val | Pro | Gly | Ser |     |
|     |     |     |     | 80  |     |     |     |     | 90  |     |     |     |     | 95  |     |

( 2 ) INFORMATION FOR SEQ ID NO:24:

( i ) SEQUENCE CHARACTERISTICS:
        ( A ) LENGTH: 86 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:24:

```
Pro Ile Phe Val Met Arg Leu Ala Lys Gln Ser Arg His Leu Glu Val
                  5                  10                  15
Gln Ile Leu Ala Asp Gln Tyr Gly Asn Ala Ile Ser Leu Phe Gly Arg
              20                  25                  30
Asp Cys Ser Val Gln Arg Arg His Gln Lys Ile Ile Glu Glu Ala Pro
          35                  40                  45
Ala Ser Ile Ala Thr Ser Val Val Phe Glu His Met Glu Gln Cys Ala
      50                  55                  60
Val Lys Leu Ala Lys Met Val Gly Tyr Val Ser Ala Gly Thr Val Glu
 65                  70                  75                  80
Tyr Leu Tyr Ser Gln Asp
                  85
```

( 2 ) INFORMATION FOR SEQ ID NO:25:

( i ) SEQUENCE CHARACTERISTICS:
        ( A ) LENGTH: 70 amino acids
        ( B ) TYPE: Amino acids
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:25:

```
Gly Ser Phe Tyr Phe Leu Glu Leu Asn Pro Arg Leu Gln Val Glu His
                  5                  10                  15
Pro Cys Thr Glu Met Val Ala Asp Val Asn Leu Pro Ala Ala Gln Leu
              20                  25                  30
Gln Ile Ala Met Gly Ile Pro Leu His Arg Ile Lys Asp Ile Arg Val
          35                  40                  45
Met Tyr Gly Val Ser Pro Trp Gly Asp Gly Ser Ile Asp Phe Glu Asn
      50                  55                  60
Ser Ala His Val Pro Cys
 65              70
```

( 2 ) INFORMATION FOR SEQ ID NO:26:

( i ) SEQUENCE CHARACTERISTICS:
        ( A ) LENGTH: 20 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:26:

```
Pro Arg Gly His Val Ile Ala Ala Arg Ile Thr Ser Glu Asn Pro Asp
                  5                  10                  15
Glu Gly Phe Lys
          20
```

( 2 ) INFORMATION FOR SEQ ID NO:27:

( i ) SEQUENCE CHARACTERISTICS:

( A ) LENGTH: 21 amino acids
                    ( B ) TYPE: Amino acid
                    ( C ) STRANDEDNESS: Single
                    ( D ) TOPOLOGY: Linear ( i i ) MOLECULE TYPE: Peptide ( x i ) SEQUENCE DESCRIPTION: SEQ ID NO:27:

Pro  Ser  Ser  Gly  Thr  Val  Gln  Glu  Leu  Asn  Phe  Arg  Ser  Asn  Lys  Asn
                    5                        10                            15

Val  Trp  Gly  Tyr  Phe
                20

( 2 ) INFORMATION FOR SEQ ID NO:28:

( i ) SEQUENCE CHARACTERISTICS:
                    ( A ) LENGTH: 122 amino acids
                    ( B ) TYPE: Amino acid
                    ( C ) STRANDEDNESS: Single
                    ( D ) TOPOLOGY: Linear ( i i ) MOLECULE TYPE: Peptide ( x i ) SEQUENCE DESCRIPTION: SEQ ID NO:28:

Ser  Val  Ala  Ala  Ala  Gly  Gly  Leu  His  Glu  Phe  Ala  Asp  Ser  Gln  Phe
                    5                        10                            15

Gly  His  Cys  Phe  Ser  Trp  Gly  Glu  Asn  Arg  Glu  Glu  Ala  Ile  Ser  Asn
                20                       25                        30

Met  Val  Val  Ala  Leu  Lys  Glu  Leu  Ser  Ile  Arg  Gly  Asp  Phe  Arg  Thr
               35                        40                       45

Thr  Val  Glu  Tyr  Leu  Ile  Lys  Leu  Leu  Glu  Thr  Glu  Ser  Phe  Gln  Gln
          50                        55                       60

Asn  Arg  Ile  Asp  Thr  Gly  Trp  Leu  Asp  Arg  Leu  Ile  Ala  Glu  Lys  Val
65                        70                       75                        80

Gln  Ala  Glu  Arg  Pro  Asp  Thr  Met  Leu  Gly  Val  Val  Cys  Gly  Ala  Leu
                    85                       90                       95

His  Val  Ala  Asp  Val  Ser  Phe  Arg  Asn  Ser  Val  Ser  Asn  Phe  Leu  His
                100                       105                      110

Ser  Leu  Glu  Arg  Gly  Gln  Val  Leu  Pro  Ala
          115                      120

( 2 ) INFORMATION FOR SEQ ID NO:29:

( i ) SEQUENCE CHARACTERISTICS:
                    ( A ) LENGTH: 90 amino acids
                    ( B ) TYPE: Amino acid
                    ( C ) STRANDEDNESS: Single
                    ( D ) TOPOLOGY: Linear ( i i ) MOLECULE TYPE: Peptide ( x i ) SEQUENCE DESCRIPTION: SEQ ID NO:29:

Met  Val  Val  Ala  Leu  Lys  Glu  Leu  Ser  Ile  Arg  Gly  Asp  Phe  Arg  Thr
                    5                        10                            15

Thr  Val  Glu  Tyr  Leu  Ile  Lys  Leu  Leu  Glu  Thr  Glu  Ser  Phe  Gln  Gln
                20                       25                        30

Asn  Arg  Ile  Asp  Thr  Gly  Trp  Leu  Asp  Arg  Leu  Ile  Ala  Glu  Lys  Val
               35                        40                       45

Gln  Ala  Glu  Arg  Pro  Asp  Thr  Met  Leu  Gly  Val  Val  Cys  Gly  Ala  Leu
          50                        55                       60

His  Val  Ala  Asp  Val  Ser  Phe  Arg  Asn  Ser  Val  Ser  Asn  Phe  Leu  His
65                        70                       75                        80

Ser Leu Glu Arg Gly Gln Val Leu Pro Ala
          85                          90

(2) INFORMATION FOR SEQ ID NO:30:

(i) SEQUENCE CHARACTERISTICS:
        (A) LENGTH: 190 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:30:

His Thr Leu Leu Asn Thr Val Asp Val Glu Leu Ile Tyr Glu Gly Arg
                  5                  10                  15

Lys Tyr Val Leu Lys Val Thr Arg Gln Ser Pro Asn Ser Tyr Val Val
              20                  25                  30

Ile Met Asn Ser Ser Cys Val Glu Val Asp Val His Arg Leu Ser Asp
          35                  40                  45

Gly Gly Leu Leu Leu Ser Tyr Asp Gly Ser Ser Thr Thr Tyr Met
      50                  55                  60

Lys Glu Glu Val Asp Arg Tyr Arg Ile Thr Ile Gly Asn Lys Thr Cys
65                  70                  75                  80

Val Phe Glu Lys Glu Asn Asp Pro Ser Ile Leu Arg Ser Pro Ser Ala
                  85                  90                  95

Gly Lys Leu Ile Gln Tyr Val Val Glu Asp Gly Gly His Val Phe Ala
                  100                 105                 110

Gly Gln Cys Phe Ala Glu Ile Glu Val Met Lys Met Val Met Thr Leu
              115                 120                 125

Thr Ala Gly Glu Ser Gly Cys Ile His Tyr Val Lys Arg Pro Gly Ala
      130                 135                 140

Val Leu Asp Pro Gly Cys Val Ile Ala Lys Leu Gln Leu Asp Asp Pro
145                 150                 155                 160

Ser Arg Val Gln Gln Ala Glu Leu His Thr Gly Thr Leu Pro Gln Ile
                  165                 170                 175

Gln Ser Thr Ala Leu Arg Gly Glu Lys Leu His Arg Ile Phe
              180                 185                 190

(2) INFORMATION FOR SEQ ID NO:31:

(i) SEQUENCE CHARACTERISTICS:
        (A) LENGTH: 41 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:31:

Met Ser Glu Glu Ser Leu Phe Glu Ser Ser Pro Gln Lys Met Glu Tyr
                  5                  10                  15

Glu Ile Thr Asn Tyr Ser Glu Arg His Thr Glu Leu Pro Gly His Phe
              20                  25                  30

Ile Gly Leu Asn Thr Val Asp Lys Leu
          35                  40

(2) INFORMATION FOR SEQ ID NO:32:

(i) SEQUENCE CHARACTERISTICS:
        (A) LENGTH: 74 amino acids
        (B) TYPE: Amino acid (C) STRANDEDNESS: Single
(D) TOPOLOGY: Linear (ii) MOLECULE TYPE: Peptide (xi) SEQUENCE DESCRIPTION: SEQ ID NO:32:

```
Ala Asp Val Asp Ala Val Trp Ala Gly Trp Gly His Ala Ser Glu Asn
                  5                  10                  15
Pro Leu Leu Pro Glu Lys Leu Ser Gln Ser Lys Arg Lys Val Ile Phe
             20                  25                  30
Ile Gly Pro Pro Gly Asn Ala Met Arg Ser Leu Gly Asp Lys Ile Ser
         35                  40                  45
Ser Thr Thr Ile Val Ala Gln Ser Ala Lys Val Pro Cys Ile Pro Trp
     50                  55                  60
Ser Gly Thr Thr Gly Val Asp Thr Val His
 65                  70
```

(2) INFORMATION FOR SEQ ID NO:33:

(i) SEQUENCE CHARACTERISTICS:
(A) LENGTH: 73 amino acids
(B) TYPE: Amino acid
(C) STRANDEDNESS: Single
(D) TOPOLOGY: Linear (ii) MOLECULE TYPE: Peptide (xi) SEQUENCE DESCRIPTION: SEQ ID NO:33:

```
Val Asp Glu Lys Thr Gly Leu Val Ser Val Asp Asp Ile Tyr Gln
                  5                  10                  15
Lys Gly Cys Cys Thr Ser Pro Glu Asp Gly Leu Gln Lys Ala Lys Arg
             20                  25                  30
Ile Gly Phe Pro Val Met Ile Lys Ala Ser Glu Gly Gly Gly Gly Lys
         35                  40                  45
Gly Ile Arg Gln Val Glu Arg Glu Glu Asp Phe Ile Ala Leu Tyr His
     50                  55                  60
Gln Ala Ala Asn Glu Ile Pro Gly Ser
 65                  70
```

(2) INFORMATION FOR SEQ ID NO:34:

(i) SEQUENCE CHARACTERISTICS:
(A) LENGTH: 157 amino acids
(B) TYPE: Amino acid
(C) STRANDEDNESS: Single
(D) TOPOLOGY: Linear (ii) MOLECULE TYPE: Peptide (xi) SEQUENCE DESCRIPTION: SEQ ID NO:34:

```
Pro Ile Phe Ile Met Lys Leu Ala Gly Arg Ala Arg His Leu Glu Val
                  5                  10                  15
Gln Leu Leu Ala Asp Gln Tyr Gly Thr Asn Ile Ser Leu Phe Gly Arg
             20                  25                  30
Asp Cys Ser Val Gln Arg Arg His Gln Lys Ile Ile Glu Glu Ala Pro
         35                  40                  45
Val Thr Ile Ala Lys Ala Glu Thr Phe His Glu Met Glu Lys Ala Ala
     50                  55                  60
Val Arg Leu Gly Lys Leu Val Gly Tyr Val Ser Ala Gly Thr Val Glu
 65                  70                  75                  80
Tyr Leu Tyr Ser His Asp Asp Gly Lys Phe Tyr Phe Leu Glu Leu Asn
                 85                  90                  95
```

```
Pro Arg Leu Gln Val Glu His Pro Thr Thr Glu Met Val Ser Gly Val
            100                     105                 110
Asn Leu Pro Ala Ala Gln Leu Gln Ile Ala Met Gly Ile Pro Met His
        115                 120                 125
Arg Ile Ser Asp Ile Arg Thr Leu Tyr Gly Met Asn Pro His Ser Ala
    130                 135                 140
Ser Glu Ile Asp Phe Glu Phe Lys Thr Gln Asp Ala Thr
145                 150                 155
```

( 2 ) INFORMATION FOR SEQ ID NO:35:

( i ) SEQUENCE CHARACTERISTICS:
        ( A ) LENGTH: 27 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:35:

```
Lys Lys Gln Arg Arg Pro Ile Pro Lys Gly His Cys Thr Ala Cys Arg
            5                   10                  15
Ile Thr Ser Glu Asp Pro Asn Asp Gly Phe Lys
            20                  25
```

( 2 ) INFORMATION FOR SEQ ID NO:36:

( i ) SEQUENCE CHARACTERISTICS:
        ( A ) LENGTH: 21 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:36:

```
Pro Ser Gly Gly Thr Leu His Glu Leu Asn Phe Arg Ser Ser Ser Asn
            5                   10                  15
Val Trp Gly Tyr Phe
            20
```

( 2 ) INFORMATION FOR SEQ ID NO:37:

( i ) SEQUENCE CHARACTERISTICS:
        ( A ) LENGTH: 122 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:37:

```
Ser Val Gly Asn Asn Gly Asn Ile His Ser Phe Ser Asp Ser Gln Phe
            5                   10                  15
Gly His Ile Phe Ala Phe Gly Glu Asn Arg Gln Ala Ser Arg Lys His
            20                  25                  30
Met Val Val Ala Leu Lys Glu Leu Ser Ile Arg Gly Asp Phe Arg Thr
        35                  40                  45
Thr Val Glu Tyr Leu Ile Lys Leu Leu Glu Thr Glu Asp Phe Glu Asp
    50                  55                  60
Asn Thr Ile Thr Thr Gly Trp Leu Asp Asp Leu Ile Thr His Lys Met
65                  70                  75                  80
Thr Ala Glu Lys Pro Asp Pro Thr Leu Ala Val Ile Cys Gly Ala Ala
```

|   |   |   | 85 |   |   |   |   | 90 |   |   |   |   | 95 |   |
|---|---|---|---|---|---|---|---|---|---|---|---|---|---|---|
| Thr | Lys | Ala | Phe | Leu | Ala | Ser | Glu | Glu | Ala | Arg | His | Lys | Tyr | Ile | Glu |
|   |   |   | 100 |   |   |   |   | 105 |   |   |   |   | 110 |   |
| Ser | Leu | Gln | Lys | Gly | Gln | Val | Leu | Ser | Lys |
|   |   |   | 115 |   |   |   |   | 120 |

(2) INFORMATION FOR SEQ ID NO:38:

(i) SEQUENCE CHARACTERISTICS:
(A) LENGTH: 190 amino acids
(B) TYPE: Amino acid
(C) STRANDEDNESS: Single
(D) TOPOLOGY: Linear (ii) MOLECULE TYPE: Peptide (xi) SEQUENCE DESCRIPTION: SEQ ID NO:38:

| Asp | Leu | Leu | Gln | Thr | Met | Phe | Pro | Val | Asp | Phe | Ile | His | Glu | Gly | Lys |
|---|---|---|---|---|---|---|---|---|---|---|---|---|---|---|---|
|   |   |   |   | 5 |   |   |   |   | 10 |   |   |   |   | 15 |
| Arg | Tyr | Lys | Phe | Thr | Val | Ala | Lys | Ser | Gly | Asn | Asp | Arg | Tyr | Thr | Leu |
|   |   |   | 20 |   |   |   |   | 25 |   |   |   |   | 30 |
| Phe | Ile | Asn | Gly | Ser | Lys | Cys | Asp | Ile | Ile | Leu | Arg | Gln | Leu | Ser | Asp |
|   |   | 35 |   |   |   |   | 40 |   |   |   |   | 45 |
| Gly | Gly | Leu | Leu | Ile | Ala | Ile | Gly | Gly | Lys | Ser | His | Thr | Ile | Tyr | Trp |
|   | 50 |   |   |   |   | 55 |   |   |   |   | 60 |
| Lys | Glu | Glu | Val | Ala | Ala | Thr | Arg | Leu | Ser | Val | Asp | Ser | Met | Thr | Thr |
| 65 |   |   |   |   | 70 |   |   |   |   | 75 |   |   |   |   | 80 |
| Leu | Leu | Glu | Val | Glu | Asn | Asp | Pro | Thr | Gln | Leu | Arg | Thr | Pro | Ser | Pro |
|   |   |   |   | 85 |   |   |   |   | 90 |   |   |   |   | 95 |
| Gly | Lys | Leu | Val | Lys | Phe | Leu | Val | Glu | Asn | Gly | Glu | His | Ile | Ile | Lys |
|   |   |   | 100 |   |   |   |   | 105 |   |   |   |   | 110 |
| Gly | Gln | Pro | Tyr | Ala | Glu | Ile | Glu | Val | Met | Lys | Met | Gln | Met | Pro | Leu |
|   |   | 115 |   |   |   |   | 120 |   |   |   |   | 125 |
| Val | Ser | Gln | Glu | Asn | Gly | Ile | Val | Gln | Leu | Leu | Lys | Gln | Pro | Gly | Ser |
|   | 130 |   |   |   |   | 135 |   |   |   |   | 140 |
| Thr | Ile | Val | Ala | Gly | Asp | Ile | Met | Ala | Ile | Met | Thr | Leu | Asp | Asp | Pro |
| 145 |   |   |   |   | 150 |   |   |   |   | 155 |   |   |   |   | 160 |
| Ser | Lys | Val | Lys | His | Ala | Leu | Pro | Phe | Glu | Gly | Met | Leu | Pro | Asp | Phe |
|   |   |   |   | 165 |   |   |   |   | 170 |   |   |   |   | 175 |
| Gly | Ser | Pro | Val | Ile | Glu | Gly | Thr | Lys | Pro | Ala | Tyr | Lys | Phe |
|   |   |   | 180 |   |   |   |   | 185 |   |   |   |   | 190 |

(2) INFORMATION FOR SEQ ID NO:39:

(i) SEQUENCE CHARACTERISTICS:
(A) LENGTH: 37 amino acids
(B) TYPE: Amino acid
(C) STRANDEDNESS: Single
(D) TOPOLOGY: Linear (ii) MOLECULE TYPE: Peptide (xi) SEQUENCE DESCRIPTION: SEQ ID NO:39:

| Met | Arg | Phe | Asn | Lys | Ile | Leu | Ile | Ala | Asn | Arg | Gly | Glu | Ile | Ala | Leu |
|---|---|---|---|---|---|---|---|---|---|---|---|---|---|---|---|
|   |   |   |   | 5 |   |   |   |   | 10 |   |   |   |   | 15 |
| Arg | Ile | Leu | Arg | Thr | Cys | Glu | Glu | Leu | Gly | Ile | Gly | Thr | Ile | Ala | Val |
|   |   |   | 20 |   |   |   |   | 25 |   |   |   |   | 30 |
| His | Ser | Thr | Val | Asp |
|   |   | 35 |

( 2 ) INFORMATION FOR SEQ ID NO:40:

( i ) SEQUENCE CHARACTERISTICS:
  ( A ) LENGTH: 21 amino acids
  ( B ) TYPE: Amino acid
  ( C ) STRANDEDNESS: Single
  ( D ) TOPOLOGY: Linear ( i i ) MOLECULE TYPE: Peptide ( x i ) SEQUENCE DESCRIPTION: SEQ ID NO:40:

```
Arg Asn Ala Leu His Val Gln Leu Ala Asp Glu Ala Val Cys Ile Gly
                  5                  10                  15
Glu Ala Ala Ser Ser
            20
```

( 2 ) INFORMATION FOR SEQ ID NO:41:

( i ) SEQUENCE CHARACTERISTICS:
  ( A ) LENGTH: 38 amino acids
  ( B ) TYPE: Amino acid
  ( C ) STRANDEDNESS: Single
  ( D ) TOPOLOGY: Linear ( i i ) MOLECULE TYPE: Peptide ( x i ) SEQUENCE DESCRIPTION: SEQ ID NO:41:

```
Lys Ser Tyr Leu Asn Ile Pro Asn Ile Ile Ala Ala Ala Leu Thr Arg
                  5                  10                  15
Asn Ala Ser Ala Ile His Pro Gly Tyr Gly Phe Leu Ala Glu Asn Ala
            20                  25                  30
Arg Phe Ala Glu Ile Cys
        35
```

( 2 ) INFORMATION FOR SEQ ID NO:42:

( i ) SEQUENCE CHARACTERISTICS:
  ( A ) LENGTH: 41 amino acids
  ( B ) TYPE: Amino acid
  ( C ) STRANDEDNESS: Single
  ( D ) TOPOLOGY: Linear ( i i ) MOLECULE TYPE: Peptide ( x i ) SEQUENCE DESCRIPTION: SEQ ID NO:42:

```
Ala Asp His His Leu Thr Phe Ile Gly Pro Ser Pro Asp Ser Ile Arg
                  5                  10                  15
Ala Met Gly Asp Lys Ser Thr Ala Lys Glu Thr Met Gln Arg Val Gly
            20                  25                  30
Val Pro Thr Ile Pro Gly Ser Asp Gly
        35                  40
```

( 2 ) INFORMATION FOR SEQ ID NO:43:

( i ) SEQUENCE CHARACTERISTICS:
  ( A ) LENGTH: 143 amino acids
  ( B ) TYPE: Amino acid
  ( C ) STRANDEDNESS: Single
  ( D ) TOPOLOGY: Linear ( i i ) MOLECULE TYPE: Peptide ( x i ) SEQUENCE DESCRIPTION: SEQ ID NO:43:

```
Leu Leu Thr Asp Val Asp Ser Ala Ala Lys Val Ala Ala Glu Ile Gly
                  5                  10                  15
Tyr Pro Val Met Ile Lys Ala Thr Ala Gly Gly Gly Gly Arg Gly Met
            20                  25                  30
```

```
Arg  Leu  Val  Arg  Glu  Pro  Ala  Asp  Leu  Glu  Lys  Leu  Phe  Leu  Ala  Ala
          35                  40                      45

Gln  Gly  Glu  Ala  Glu  Ala  Ala  Phe  Gly  Asn  Pro  Gly  Leu  Tyr  Leu  Glu
     50                       55                      60

Lys  Phe  Ile  Asp  Arg  Pro  Arg  His  Val  Glu  Phe  Gln  Ile  Leu  Ala  Asp
65                       70                  75                            80

Ala  Tyr  Gly  Asn  Val  Val  His  Leu  Gly  Glu  Arg  Asp  Cys  Ser  Ile  Gln
                    85             90                            95

Arg  Arg  His  Gln  Lys  Leu  Leu  Glu  Glu  Ala  Pro  Ser  Pro  Ala  Leu  Ser
               100                 105                      110

Ala  Asp  Leu  Arg  Gln  Lys  Met  Gly  Asp  Ala  Ala  Val  Lys  Val  Ala  Gln
          115                 120                      125

Ala  Ile  Gly  Tyr  Ile  Gly  Ala  Gly  Thr  Val  Glu  Phe  Leu  Val  Asp
          130                 135                      140
```

(2) INFORMATION FOR SEQ ID NO:44:

(i) SEQUENCE CHARACTERISTICS:
        (A) LENGTH: 50 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:44:

```
Ala  Thr  Gly  Asn  Phe  Tyr  Phe  Met  Glu  Met  Asn  Thr  Arg  Ile  Gln  Val
                    5                   10                       15

Glu  His  Pro  Val  Thr  Glu  Met  Ile  Thr  Gly  Leu  Asp  Leu  Ile  Ala  Glu
               20                  25                       30

Gln  Ile  Arg  Ile  Ala  Gln  Gly  Glu  Ala  Leu  Arg  Phe  Arg  Gln  Ala  Asp
          35                  40                       45

Ile  Gln
     50
```

(2) INFORMATION FOR SEQ ID NO:45:

(i) SEQUENCE CHARACTERISTICS:
        (A) LENGTH: 19 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:45:

```
Leu  Arg  Gly  His  Ala  Ile  Glu  Cys  Arg  Ile  Asn  Ala  Glu  Asp  Pro  Glu
                    5                   10                       15

Tyr  Asn  Phe
```

(2) INFORMATION FOR SEQ ID NO:46:

(i) SEQUENCE CHARACTERISTICS:
        (A) LENGTH: 9 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:46:

```
Arg  Pro  Asn  Pro  Gly  Arg  Ile  Thr  Gly
                    5
```

(2) INFORMATION FOR SEQ ID NO:47:

(i) SEQUENCE CHARACTERISTICS:
        (A) LENGTH: 7 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:47:

Pro Gly Val Arg Val Asp Ser
            5

(2) INFORMATION FOR SEQ ID NO:48:

(i) SEQUENCE CHARACTERISTICS:
        (A) LENGTH: 44 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:48:

His Val Tyr Thr Asp Tyr Glu Ile Pro Pro Tyr Tyr Asp Ser Leu Ile
            5                    10                  15

Gly Lys Leu Ile Val Trp Gly Ala Thr Arg Glu Glu Ala Ile Ala Arg
         20                   25                 30

Met Gln Arg Ala Leu Arg Glu Cys Ala Ile Thr Gly
       35               40

(2) INFORMATION FOR SEQ ID NO:49:

(i) SEQUENCE CHARACTERISTICS:
        (A) LENGTH: 38 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:49:

Leu Pro Thr Thr Leu Ser Phe His Gln Leu Met Leu Gln Met Pro Glu
            5                    10                  15

Phe Leu Arg Gly Glu Leu Tyr Thr Asn Phe Val Glu Gln Val Met Leu
         20                   25                 30

Pro Arg Ile Leu Lys Ser
       35

(2) INFORMATION FOR SEQ ID NO:50:

(i) SEQUENCE CHARACTERISTICS:
        (A) LENGTH: 37 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:50:

Met Lys Phe Asp Lys Ile Leu Ile Ala Asn Arg Gly Glu Ile Ala Leu
            5                    10                  15

Arg Ile Leu Arg Ala Cys Glu Glu Met Gly Ile Ala Thr Ile Ala Val
         20                   25                 30

His Ser Thr Val Asp
         35

( 2 ) INFORMATION FOR SEQ ID NO:51:

( i ) SEQUENCE CHARACTERISTICS:
         ( A ) LENGTH: 21 amino acids
         ( B ) TYPE: Amino acid
         ( C ) STRANDEDNESS: Single
         ( D ) TOPOLOGY: Linear ( i i ) MOLECULE TYPE: Peptide ( x i ) SEQUENCE DESCRIPTION: SEQ ID NO:51:

Arg Asn Ala Leu His Val Gln Leu Ala Asp Glu Ala Val Cys Ile Gly
                  5                  10                     15
Glu Pro Ala Ser Ala
            20

( 2 ) INFORMATION FOR SEQ ID NO:52:

( i ) SEQUENCE CHARACTERISTICS:
         ( A ) LENGTH: 38 amino acids
         ( B ) TYPE: Amino acid
         ( C ) STRANDEDNESS: Single
         ( D ) TOPOLOGY: Linear ( i i ) MOLECULE TYPE: Peptide ( x i ) SEQUENCE DESCRIPTION: SEQ ID NO:52:

Lys Ser Tyr Leu Asn Ile Pro Asn Ile Ile Ala Ala Ala Leu Thr Arg
                  5                  10                     15
Asn Ala Ser Ala Ile His Pro Gly Tyr Gly Phe Leu Ser Glu Asn Ala
            20                  25                  30
Lys Phe Ala Glu Ile Cys
         35

( 2 ) INFORMATION FOR SEQ ID NO:53:

( i ) SEQUENCE CHARACTERISTICS:
         ( A ) LENGTH: 42 amino acids
         ( B ) TYPE: Amino acid
         ( C ) STRANDEDNESS: Single
         ( D ) TOPOLOGY: Linear ( i i ) MOLECULE TYPE: Peptide ( x i ) SEQUENCE DESCRIPTION: SEQ ID NO:53:

Ala Asp His His Ile Ala Phe Ile Gly Pro Thr Pro Glu Ala Ile Arg
                  5                  10                     15
Leu Met Gly Asp Lys Ser Thr Ala Lys Glu Thr Met Gln Lys Ala Gly
            20                  25                  30
Val Pro Thr Val Pro Gly Ser Glu Gly Leu
         35                  40

( 2 ) INFORMATION FOR SEQ ID NO:54:

( i ) SEQUENCE CHARACTERISTICS:
         ( A ) LENGTH: 142 amino acids
         ( B ) TYPE: Amino acid
         ( C ) STRANDEDNESS: Single
         ( D ) TOPOLOGY: Linear ( i i ) MOLECULE TYPE: Peptide ( x i ) SEQUENCE DESCRIPTION: SEQ ID NO:54:

Val Glu Thr Glu Gln Glu Gly Leu Glu Leu Ala Lys Asp Ile Gly Tyr

|  | | | | | 5 | | | | | 10 | | | | | 15 | |
|---|---|---|---|---|---|---|---|---|---|---|---|---|---|---|---|---|
| Pro | Val | Met | Ile | Lys | Ala | Thr | Ala | Gly | Gly | Gly | Arg | Gly | Met | Arg |
| | | | | 20 | | | | | 25 | | | | | 30 | |
| Leu | Val | Arg | Ser | Pro | Asp | Glu | Phe | Val | Lys | Leu | Phe | Leu | Ala | Ala | Gln |
| | | | 35 | | | | 40 | | | | | 45 | | | |
| Gly | Glu | Ala | Gly | Ala | Ala | Phe | Gly | Asn | Ala | Gly | Val | Tyr | Ile | Glu | Lys |
| | 50 | | | | | 55 | | | | | 60 | | | | |
| Phe | Ile | Glu | Arg | Pro | Arg | His | Ile | Glu | Phe | Gln | Ile | Leu | Ala | Asp | Asn |
| 65 | | | | | 70 | | | | | 75 | | | | | 80 |
| Tyr | Gly | Asn | Val | Ile | His | Leu | Gly | Glu | Arg | Asp | Cys | Ser | Ile | Gln | Arg |
| | | | | 85 | | | | | 90 | | | | | 95 | |
| Arg | Asn | Gln | Lys | Leu | Leu | Glu | Glu | Ala | Pro | Ser | Pro | Ala | Leu | Asp | Ser |
| | | | 100 | | | | | 105 | | | | | 110 | | |
| Asp | Leu | Arg | Glu | Lys | Met | Gly | Gln | Ala | Ala | Val | Lys | Ala | Ala | Gln | Phe |
| | | 115 | | | | | 120 | | | | | 125 | | | |
| Ile | Asn | Tyr | Ala | Gly | Ala | Gly | Thr | Ile | Glu | Phe | Leu | Leu | Asp | | |
| | 130 | | | | | 135 | | | | | 140 | | | | |

( 2 ) INFORMATION FOR SEQ ID NO:55:

( i ) SEQUENCE CHARACTERISTICS:
        ( A ) LENGTH: 50 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:55:

| Arg | Ser | Gly | Gln | Phe | Tyr | Phe | Met | Glu | Met | Asn | Thr | Arg | Ile | Gln | Val |
|---|---|---|---|---|---|---|---|---|---|---|---|---|---|---|---|
| | | | | 5 | | | | | 10 | | | | | 15 | |
| Glu | His | Pro | Val | Thr | Glu | Met | Val | Thr | Gly | Val | Asp | Leu | Leu | Val | Glu |
| | | | 20 | | | | | 25 | | | | | 30 | | |
| Gln | Ile | Arg | Ile | Ala | Gln | Gly | Glu | Arg | Leu | Arg | Leu | Thr | Gln | Asp | Gln |
| | | 35 | | | | | 40 | | | | | 45 | | | |
| Val | Val | | | | | | | | | | | | | | |
| | 50 | | | | | | | | | | | | | | |

( 2 ) INFORMATION FOR SEQ ID NO:56:

( i ) SEQUENCE CHARACTERISTICS:
        ( A ) LENGTH: 19 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:56:

| Leu | Arg | Gly | His | Ala | Ile | Glu | Cys | Arg | Ile | Asn | Ala | Glu | Asp | Pro | Asp |
|---|---|---|---|---|---|---|---|---|---|---|---|---|---|---|---|
| | | | | 5 | | | | | 10 | | | | | 15 | |
| His | Asp | Phe | | | | | | | | | | | | | |

( 2 ) INFORMATION FOR SEQ ID NO:57:

( i ) SEQUENCE CHARACTERISTICS:
        ( A ) LENGTH: 9 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:57:

Arg Pro Ala Pro Gly Arg Ile Ser Gly
                    5

( 2 ) INFORMATION FOR SEQ ID NO:58:

( i ) SEQUENCE CHARACTERISTICS:
        ( A ) LENGTH: 6 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:58:

Tyr Leu Pro Pro Gly Gly
                5

( 2 ) INFORMATION FOR SEQ ID NO:59:

( i ) SEQUENCE CHARACTERISTICS:
        ( A ) LENGTH: 7 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:59:

Pro Gly Val Arg Ile Asp Ser
                    5

( 2 ) INFORMATION FOR SEQ ID NO:60:

( i ) SEQUENCE CHARACTERISTICS:
        ( A ) LENGTH: 44 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:60:

His Val Tyr Thr Asp Tyr Gln Ile Pro Pro Tyr Tyr Asp Ser Leu Ile
                 5                  10                  15

Gly Lys Leu Ile Val Trp Gly Pro Asp Arg Ala Thr Ala Ile Asn Arg
                20                  25                  30

Met Lys Arg Ala Leu Arg Glu Cys Ala Ile Thr Gly
            35                  40

( 2 ) INFORMATION FOR SEQ ID NO:61:

( i ) SEQUENCE CHARACTERISTICS:
        ( A ) LENGTH: 154 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:61:

Leu Pro Thr Thr Ile Gly Phe His Gln Arg Ile Met Glu Asn Pro Gln
                 5                  10                  15

Phe Leu Gln Gly Asn Val Ser Thr Ser Phe Val Gln Glu Met Asn Lys
                20                  25                  30

Pro Leu Asp Phe Asn Glu Ile Arg Gln Leu Leu Thr Thr Ile Ala Gln
            35                  40                  45

```
Thr  Asp  Ile  Ala  Glu  Val  Thr  Leu  Lys  Ser  Asp  Asp  Phe  Glu  Leu  Thr
     50                  55                      60
Val  Arg  Lys  Ala  Val  Gly  Val  Asn  Asn  Ser  Val  Val  Pro  Val  Val  Thr
65                       50                      75                           80
Ala  Pro  Leu  Ser  Gly  Val  Val  Gly  Ser  Gly  Leu  Pro  Ser  Ala  Ile  Pro
                    85                       90                      95
Ile  Val  Ala  His  Ala  Ala  Pro  Ser  Pro  Ser  Pro  Glu  Pro  Gly  Thr  Ser
               100                      105                     110
Arg  Ala  Ala  Asp  His  Ala  Val  Thr  Ser  Ser  Gly  Ser  Gln  Pro  Gly  Ala
               115                 120                     125
Lys  Ile  Ile  Asp  Gln  Lys  Leu  Ala  Glu  Val  Ala  Ser  Pro  Met  Val  Gly
     130                      135                     140
Thr  Phe  Tyr  Arg  Ala  Pro  Ala  Pro  Gly  Glu
145                      150
```

( 2 ) INFORMATION FOR SEQ ID NO:62:

( i ) SEQUENCE CHARACTERISTICS:
        ( A ) LENGTH: 24 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:62:

```
Ala  Val  Phe  Val  Glu  Val  Gly  Asp  Arg  Ile  Arg  Gln  Gly  Gln  Thr  Val
                    5                   10                      15
Cys  Ile  Ile  Glu  Ala  Met  Lys  Met
               20
```

( 2 ) INFORMATION FOR SEQ ID NO:63:

( i ) SEQUENCE CHARACTERISTICS:
        ( A ) LENGTH: 36 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:63:

```
Met  Leu  Asp  Lys  Ile  Val  Ile  Ala  Asn  Arg  Gly  Glu  Ile  Ala  Leu  Arg
                    5                   10                      15
Ile  Leu  Arg  Ala  Cys  Lys  Glu  Leu  Gly  Ile  Lys  Thr  Val  Ala  Val  His
               20                  25                      30
Ser  Ser  Ala  Asp
          35
```

( 2 ) INFORMATION FOR SEQ ID NO:64:

( i ) SEQUENCE CHARACTERISTICS:
        ( A ) LENGTH: 21 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:64:

```
Arg  Asp  Leu  Lys  His  Val  Leu  Leu  Ala  Asp  Glu  Thr  Val  Cys  Ile  Gly
                    5                   10                      15
Pro  Ala  Pro  Ser  Val
```

(2) INFORMATION FOR SEQ ID NO:65:

(i) SEQUENCE CHARACTERISTICS:
        (A) LENGTH: 38 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:65:

```
Lys Ser Tyr Leu Asn Ile Pro Ala Ile Ile Ser Ala Ala Glu Ile Thr
                 5                  10                  15
Gly Ala Val Ala Ile His Pro Gly Tyr Gly Phe Leu Ser Glu Asn Ala
             20                  25                  30
Asn Phe Ala Glu Gln Val
             35
```

(2) INFORMATION FOR SEQ ID NO:66:

(i) SEQUENCE CHARACTERISTICS:
        (A) LENGTH: 43 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:66:

```
Glu Arg Ser Gly Phe Ile Phe Ile Gly Pro Lys Ala Glu Thr Ile Arg
                 5                  10                  15
Leu Met Gly Asp Lys Val Ser Ala Ile Ala Ala Met Lys Lys Ala Gly
             20                  25                  30
Val Pro Cys Val Pro Gly Ser Asp Gly Pro Leu
             35                  40
```

(2) INFORMATION FOR SEQ ID NO:67:

(i) SEQUENCE CHARACTERISTICS:
        (A) LENGTH: 141 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:67:

```
Gly Asp Asp Met Asp Lys Asn Arg Ala Ile Ala Lys Arg Ile Gly Tyr
                 5                  10                  15
Pro Val Ile Ile Lys Ala Ser Gly Gly Gly Gly Arg Gly Met Arg
             20                  25                  30
Val Val Arg Gly Asp Ala Glu Leu Ala Gln Ser Ile Ser Met Thr Arg
             35                  40                  45
Ala Glu Ala Lys Ala Ala Phe Ser Asn Asp Met Val Tyr Met Glu Lys
 50                  55                  60
Tyr Leu Glu Asn Pro Arg His Val Glu Ile Gln Val Leu Ala Asp Gly
 65                  70                  75                  80
Gln Gly Asn Ala Ile Tyr Leu Ala Glu Arg Asp Cys Ser Met Gln Arg
                 85                  90                  95
Arg His Gln Lys Val Val Glu Glu Ala Pro Ala Pro Gly Ile Thr Pro
             100                 105                 110
```

```
Glu  Leu  Arg  Arg  Tyr  Ile  Gly  Glu  Arg  Cys  Ala  Lys  Ala  Cys  Val  Asp
              115                      120                      125

Ile  Gly  Tyr  Arg  Ala  Gly  Thr  Phe  Glu  Phe  Leu  Phe
          130                 135                 140
```

( 2 ) INFORMATION FOR SEQ ID NO:68:

( i ) SEQUENCE CHARACTERISTICS:
      ( A ) LENGTH: 50 amino acids
      ( B ) TYPE: Amino acid
      ( C ) STRANDEDNESS: Single
      ( D ) TOPOLOGY: Linear ( i i ) MOLECULE TYPE: Peptide ( x i ) SEQUENCE DESCRIPTION: SEQ ID NO:68:

```
Glu  Asn  Gly  Glu  Phe  Tyr  Phe  Ile  Glu  Met  Asn  Thr  Arg  Ile  Gln  Val
                    5                     10                           15

Glu  His  Pro  Val  Thr  Glu  Met  Ile  Thr  Gly  Val  Asp  Leu  Ile  Lys  Glu
              20                         25                      30

Gln  Met  Arg  Ile  Ala  Ala  Gly  Gln  Pro  Leu  Ser  Ile  Lys  Gln  Glu  Glu
              35                    40                      45

Val  His
     50
```

( 2 ) INFORMATION FOR SEQ ID NO:69:

( i ) SEQUENCE CHARACTERISTICS:
      ( A ) LENGTH: 25 amino acids
      ( B ) TYPE: Amino acid
      ( C ) STRANDEDNESS: Single
      ( D ) TOPOLOGY: Linear ( i i ) MOLECULE TYPE: Peptide ( x i ) SEQUENCE DESCRIPTION: SEQ ID NO:69:

```
Val  Arg  Gly  His  Ala  Val  Glu  Cys  Arg  Ile  Asn  Ala  Glu  Asp  Pro  Asn
                    5                     10                           15

Leu  Pro  Ser  Pro  Gly  Lys  Ile  Thr  Arg
              20                      25
```

( 2 ) INFORMATION FOR SEQ ID NO:70:

( i ) SEQUENCE CHARACTERISTICS:
      ( A ) LENGTH: 6 amino acids
      ( B ) TYPE: Amino acid
      ( C ) STRANDEDNESS: Single
      ( D ) TOPOLOGY: Linear ( i i ) MOLECULE TYPE: Peptide ( x i ) SEQUENCE DESCRIPTION: SEQ ID NO:70:

```
Phe  His  Ala  Pro  Gly  Gly
                    5
```

( 2 ) INFORMATION FOR SEQ ID NO:71:

( i ) SEQUENCE CHARACTERISTICS:
      ( A ) LENGTH: 7 amino acids
      ( B ) TYPE: Amino acid
      ( C ) STRANDEDNESS: Single
      ( D ) TOPOLOGY: Linear ( i i ) MOLECULE TYPE: Peptide ( x i ) SEQUENCE DESCRIPTION: SEQ ID NO:71:

```
Phe  Gly  Val  Arg  Trp  Glu  Ser
```

( 2 ) INFORMATION FOR SEQ ID NO:72:

( i ) SEQUENCE CHARACTERISTICS:
        ( A ) LENGTH: 44 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:72:

```
His Ile Tyr Ala Gly Tyr Thr Val Pro Pro Tyr Tyr Asp Ser Met Ile
                 5                   10                  15
Gly Lys Leu Ile Cys Tyr Gly Glu Asn Arg Asp Val Ala Ile Ala Arg
             20              25                  30
Met Lys Asn Ala Leu Gln Glu Leu Ile Ile Asp Gly
         35              40
```

( 2 ) INFORMATION FOR SEQ ID NO:73:

( i ) SEQUENCE CHARACTERISTICS:
        ( A ) LENGTH: 135 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:73:

```
Ile Lys Thr Asn Val Asp Leu Gln Ile Arg Ile Met Asn Asp Glu Asn
                 5                   10                  15
Phe Gln His Gly Gly Thr Asn Ile His Tyr Leu Glu Lys Lys Leu Gly
             20              25                  30
Leu Gln Glu Lys Met Asp Ile Arg Lys Ile Lys Lys Leu Ile Glu Leu
         35              40                  45
Val Glu Glu Ser Gly Ile Ser Glu Leu Glu Ile Ser Glu Gly Glu Glu
     50              55                  60
Ser Val Arg Ile Ser Arg Ala Ala Pro Ala Ala Ser Phe Pro Val Met
65               70                  75                  80
Gln Gln Ala Tyr Ala Ala Pro Met Met Gln Gln Pro Ala Gln Ser Asn
             85              90                  95
Ala Ala Ala Pro Ala Thr Val Pro Ser Met Glu Ala Pro Ala Ala Ala
         100             105                 110
Glu Ile Ser Gly His Ile Val Arg Ser Pro Met Val Gly Thr Phe Tyr
             115             120                 125
Arg Thr Pro Ser Pro Asp Ala
     130             135
```

( 2 ) INFORMATION FOR SEQ ID NO:74:

( i ) SEQUENCE CHARACTERISTICS:
        ( A ) LENGTH: 57 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:74:

```
Lys Ala Phe Ile Glu Val Gly Gln Lys Val Asn Val Gly Asp Thr Leu
                 5                   10                  15
```

```
Cys  Ile  Val  Glu  Ala  Met  Lys  Met  Met  Asn  Gln  Ile  Glu  Ala  Asp  Lys
               20                       25                       30

Ser  Gly  Thr  Val  Lys  Ala  Ile  Leu  Val  Glu  Ser  Gly  Gln  Pro  Val  Glu
               35                       40                       45

Phe  Asp  Glu  Pro  Leu  Val  Val  Ile  Glu
          50                  55
```

( 2 ) INFORMATION FOR SEQ ID NO:75:

( i ) SEQUENCE CHARACTERISTICS:
        ( A ) LENGTH: 72 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:75:

```
Met  Leu  Ser  Ala  Ala  Leu  Arg  Thr  Leu  Lys  His  Val  Leu  Tyr  Tyr  Ser
               5                        10                       15

Arg  Gln  Cys  Leu  Met  Val  Ser  Arg  Asn  Leu  Gly  Ser  Val  Gly  Tyr  Asp
               20                       25                       30

Pro  Asn  Glu  Lys  Thr  Phe  Asp  Lys  Ile  Leu  Val  Ala  Asn  Arg  Gly  Glu
               35                       40                       45

Ile  Ala  Cys  Arg  Val  Ile  Arg  Thr  Cys  Lys  Lys  Met  Gly  Ile  Lys  Thr
          50                  55                       60

Val  Ala  Ile  His  Ser  Asp  Val  Asp
65                       70
```

( 2 ) INFORMATION FOR SEQ ID NO:76:

( i ) SEQUENCE CHARACTERISTICS:
        ( A ) LENGTH: 21 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:76:

```
Ala  Ser  Ser  Val  His  Val  Lys  Met  Ala  Asp  Glu  Ala  Val  Cys  Val  Gly
               5                        10                       15

Pro  Ala  Pro  Thr  Ser
               20
```

( 2 ) INFORMATION FOR SEQ ID NO:77:

( i ) SEQUENCE CHARACTERISTICS:
        ( A ) LENGTH: 38 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:77:

```
Lys  Ser  Tyr  Leu  Asn  Met  Asp  Ala  Ile  Met  Glu  Ala  Ile  Lys  Lys  Thr
               5                        10                       15

Arg  Ala  Gln  Ala  Val  His  Pro  Gly  Tyr  Gly  Phe  Leu  Ser  Glu  Asn  Lys
               20                       25                       30

Glu  Phe  Ala  Arg  Cys  Leu
               35
```

( 2 ) INFORMATION FOR SEQ ID NO:78:

( i ) SEQUENCE CHARACTERISTICS:
- ( A ) LENGTH: 41 amino acids
- ( B ) TYPE: Amino acid
- ( C ) STRANDEDNESS: Single
- ( D ) TOPOLOGY: Linear ( i i ) MOLECULE TYPE: Peptide ( x i ) SEQUENCE DESCRIPTION: SEQ ID NO:78:

```
Ala Ala Glu Asp Val Val Phe Ile Gly Pro Asp Thr His Ala Ile Gln
                 5                  10                     15
Ala Met Gly Asp Lys Ile Glu Ser Lys Leu Leu Ala Lys Lys Ala Glu
             20              25                  30
Val Asn Thr Ile Pro Gly Phe Asp Gly
         35              40
```

( 2 ) INFORMATION FOR SEQ ID NO:79:

( i ) SEQUENCE CHARACTERISTICS:
- ( A ) LENGTH: 144 amino acids
- ( B ) TYPE: Amino acid
- ( C ) STRANDEDNESS: Single
- ( D ) TOPOLOGY: Linear ( i i ) MOLECULE TYPE: Peptide ( x i ) SEQUENCE DESCRIPTION: SEQ ID NO:79:

```
Val Lys Asp Ala Glu Glu Ala Val Arg Ile Ala Arg Glu Ile Gly Tyr
                 5                  10                     15
Pro Val Met Ile Lys Ala Ser Ala Gly Gly Gly Gly Lys Gly Met Arg
             20              25                  30
Ile Ala Trp Asp Asp Glu Glu Thr Arg Asp Gly Phe Arg Leu Ser Ser
             35              40                  45
Gln Glu Ala Ala Ser Ser Phe Gly Asp Asp Arg Leu Leu Ile Glu Lys
     50              55                  60
Phe Ile Asp Asn Pro Arg His Ile Glu Ile Gln Val Leu Gly Asp Lys
65                  70                  75                  80
His Gly Asn Ala Leu Trp Leu Asn Glu Arg Glu Cys Ser Ile Gln Arg
                 85              90                      95
Arg Asn Gln Lys Val Val Glu Glu Ala Pro Ser Ile Phe Leu Asp Ala
             100             105                 110
Glu Thr Arg Arg Ala Met Gly Glu Gln Ala Val Ala Leu Ala Arg Ala
         115             120                 125
Val Lys Tyr Ser Ser Ala Gly Thr Val Glu Phe Leu Val Asp Ser Lys
     130             135                 140
```

( 2 ) INFORMATION FOR SEQ ID NO:80:

( i ) SEQUENCE CHARACTERISTICS:
- ( A ) LENGTH: 47 amino acids
- ( B ) TYPE: Amino acid
- ( C ) STRANDEDNESS: Single
- ( D ) TOPOLOGY: Linear ( i i ) MOLECULE TYPE: Peptide ( x i ) SEQUENCE DESCRIPTION: SEQ ID NO:80:

```
Lys Asn Phe Tyr Phe Leu Glu Met Asn Thr Arg Leu Gln Val Glu His
                 5                  10                     15
Pro Val Thr Glu Cys Ile His Trp Pro Gly Pro Ser Pro Gly Lys Thr
             20              25                  30
Val Leu Gln Glu His Leu Ser Gly Thr Asn Lys Leu Ile Phe Ala
```

( 2 ) INFORMATION FOR SEQ ID NO:81:

( i ) SEQUENCE CHARACTERISTICS:
        ( A ) LENGTH: 29 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:81:

Phe Asn Gly Trp Ala Val Glu Cys Arg Val Tyr Ala Glu Asp Pro Tyr
               5                          10                    15

Lys Ser Phe Gly Leu Pro Ser Ile Gly Arg Leu Ser Gln
              20                  25

( 2 ) INFORMATION FOR SEQ ID NO:82:

( i ) SEQUENCE CHARACTERISTICS:
        ( A ) LENGTH: 14 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:82:

Tyr Gln Glu Pro Leu His Leu Pro Gly Val Arg Val Asp Ser
               5                        10

( 2 ) INFORMATION FOR SEQ ID NO:83:

( i ) SEQUENCE CHARACTERISTICS:
        ( A ) LENGTH: 44 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:83:

Gly Ile Gln Pro Gly Ser Asp Ile Ser Ile Tyr Tyr Asp Pro Met Ile
               5                      10               15

Ser Lys Leu Ile Thr Tyr Gly Ser Asp Arg Thr Glu Ala Leu Lys Arg
            20                  25               30

Met Ala Asp Ala Leu Asp Asn Tyr Val Ile Arg Gly
          35                40

( 2 ) INFORMATION FOR SEQ ID NO:84:

( i ) SEQUENCE CHARACTERISTICS:
        ( A ) LENGTH: 251 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:84:

Val Thr His Asn Ile Ala Leu Leu Arg Glu Val Ile Ile Asn Ser Arg
               5                      10               15

Phe Val Lys Gly Asp Ile Ser Thr Lys Phe Leu Ser Asp Val Tyr Pro
            20                  25               30

Asp Gly Phe Lys Gly His Met Leu Thr Lys Ser Glu Lys Asn Gln Leu
          35                40               45

| | | | | | | | | | | | | | |
|---|---|---|---|---|---|---|---|---|---|---|---|---|---|
| Leu | Ala | Ile | Ala | Ser | Ser | Leu | Phe | Val | Ala | Phe | Gln | Leu | Arg | Ala | Gln |
| | 50 | | | | 55 | | | | | 60 | | | | |
| His | Phe | Gln | Glu | Asn | Ser | Arg | Met | Pro | Val | Ile | Lys | Pro | Asp | Ile | Ala |
| 65 | | | | | 70 | | | | 75 | | | | | | 80 |
| Asn | Trp | Glu | Leu | Ser | Val | Lys | Leu | His | Asp | Lys | Val | His | Thr | Val | Val |
| | | | | 85 | | | | | 90 | | | | | 95 | |
| Ala | Ser | Asn | Asn | Gly | Ser | Val | Phe | Ser | Val | Glu | Val | Asp | Gly | Ser | Lys |
| | | | 100 | | | | | 105 | | | | | 110 | | |
| Leu | Asn | Val | Thr | Ser | Thr | Trp | Asn | Leu | Ala | Ser | Pro | Leu | Leu | Ser | Val |
| | | | 115 | | | | 120 | | | | | 125 | | | |
| Ser | Val | Asp | Gly | Thr | Gln | Arg | Thr | Val | Gln | Cys | Leu | Ser | Arg | Glu | Ala |
| | | 130 | | | | 135 | | | | | 140 | | | | |
| Gly | Gly | Asn | Met | Ser | Ile | Gln | Phe | Leu | Gly | Thr | Val | Tyr | Lys | Val | Asn |
| 145 | | | | | 150 | | | | | 155 | | | | | 160 |
| Ile | Leu | Thr | Arg | Leu | Ala | Ala | Glu | Leu | Asn | Lys | Phe | Met | Leu | Glu | Lys |
| | | | | 165 | | | | | 170 | | | | | 175 | |
| Val | Thr | Glu | Asp | Thr | Ser | Ser | Val | Leu | Arg | Ser | Pro | Met | Pro | Gly | Val |
| | | | 180 | | | | | 185 | | | | | 190 | | |
| Val | Val | Ala | Val | Ser | Val | Lys | Pro | Gly | Asp | Ala | Val | Ala | Glu | Gly | Gln |
| | | 195 | | | | | 200 | | | | | 205 | | | |
| Glu | Ile | Cys | Val | Ile | Glu | Ala | Met | Lys | Met | Gln | Asn | Ser | Met | Thr | Ala |
| | 210 | | | | | 215 | | | | 220 | | | | | |
| Gly | Lys | Thr | Gly | Thr | Val | Lys | Ser | Val | His | Cys | Gln | Ala | Gly | Asp | Thr |
| 225 | | | | | 230 | | | | | 235 | | | | | 240 |
| Val | Gly | Glu | Gly | Asp | Leu | Leu | Val | Glu | Leu | | | | | | |
| | | | | 245 | | | | | 250 | | | | | | |

( 2 ) INFORMATION FOR SEQ ID NO:85:

( i ) SEQUENCE CHARACTERISTICS:
        ( A ) LENGTH: 90 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:85:

| | | | | | | | | | | | | | | | |
|---|---|---|---|---|---|---|---|---|---|---|---|---|---|---|---|
| Met | Pro | Tyr | Arg | Glu | Arg | Phe | Cys | Ala | Ile | Arg | Trp | Cys | Arg | Asn | Ser |
| | | | | 5 | | | | | 10 | | | | | 15 | |
| Gly | Arg | Ser | Ser | Gln | Gln | Leu | Leu | Trp | Thr | Leu | Lys | Arg | Ala | Pro | Val |
| | | | 20 | | | | | 25 | | | | | 30 | | |
| Tyr | Ser | Gln | Gln | Cys | Leu | Val | Val | Ser | Arg | Ser | Leu | Ser | Ser | Val | Glu |
| | | 35 | | | | | 40 | | | | | 45 | | | |
| Tyr | Glu | Pro | Lys | Glu | Lys | Thr | Phe | Asp | Lys | Ile | Leu | Ile | Ala | Asn | Arg |
| | 50 | | | | | 55 | | | | | 60 | | | | |
| Gly | Glu | Ile | Ala | Cys | Arg | Val | Ile | Lys | Thr | Cys | Arg | Lys | Met | Gly | Ile |
| 65 | | | | | 70 | | | | | 75 | | | | | 80 |
| Arg | Thr | Val | Ala | Ile | His | Ser | Asp | Val | Asp | | | | | | |
| | | | | 85 | | | | | 90 | | | | | | |

( 2 ) INFORMATION FOR SEQ ID NO:86:

( i ) SEQUENCE CHARACTERISTICS:
        ( A ) LENGTH: 21 amino acids
        ( B ) TYPE: Amino acid
        ( C ) STRANDEDNESS: Single
        ( D ) TOPOLOGY: Linear 5,792,627

( i i ) MOLECULE TYPE: Peptide ( x i ) SEQUENCE DESCRIPTION: SEQ ID NO:86:

Ala Ser Ser Val His Val Lys Met Ala Asp Glu Ala Val Cys Val Gly
                    5                   10                  15
Pro Ala Pro Thr Ser
            20

( 2 ) INFORMATION FOR SEQ ID NO:87:

( i ) SEQUENCE CHARACTERISTICS:
      ( A ) LENGTH: 38 amino acids
      ( B ) TYPE: Amino acid
      ( C ) STRANDEDNESS: Single
      ( D ) TOPOLOGY: Linear ( i i ) MOLECULE TYPE: Peptide ( x i ) SEQUENCE DESCRIPTION: SEQ ID NO:87:

Lys Ser Tyr Leu Asn Met Asp Ala Ile Met Glu Ala Ile Lys Lys Thr
                    5                   10                  15
Gly Ala Gln Ala Val His Pro Gly Tyr Gly Phe Leu Ser Glu Asn Lys
            20                  25                  30
Glu Phe Ala Lys Cys Leu
            35

( 2 ) INFORMATION FOR SEQ ID NO:88:

( i ) SEQUENCE CHARACTERISTICS:
      ( A ) LENGTH: 41 amino acids
      ( B ) TYPE: Amino acid
      ( C ) STRANDEDNESS: Single
      ( D ) TOPOLOGY: Linear ( i i ) MOLECULE TYPE: Peptide ( x i ) SEQUENCE DESCRIPTION: SEQ ID NO:88:

Ala Ala Glu Asp Val Thr Phe Ile Gly Pro Asp Thr His Ala Ile Gln
                    5                   10                  15
Ala Met Gly Asp Lys Ile Glu Ser Lys Leu Leu Ala Lys Arg Ala Lys
            20                  25                  30
Val Asn Thr Ile Pro Gly Phe Asp Gly
            35              40

( 2 ) INFORMATION FOR SEQ ID NO:89:

( i ) SEQUENCE CHARACTERISTICS:
      ( A ) LENGTH: 144 amino acids
      ( B ) TYPE: Amino acid
      ( C ) STRANDEDNESS: Single
      ( D ) TOPOLOGY: Linear ( i i ) MOLECULE TYPE: Peptide ( x i ) SEQUENCE DESCRIPTION: SEQ ID NO:89:

Leu Lys Asp Ala Asp Glu Ala Val Arg Ile Ala Arg Glu Ile Gly Tyr
                    5                   10                  15
Pro Val Met Ile Lys Ala Ser Ala Gly Gly Gly Lys Gly Met Arg
            20                  25                  30
Ile Pro Trp Asp Asp Glu Glu Thr Arg Asp Gly Phe Arg Phe Ser Ser
            35                  40                  45
Gln Glu Ala Ala Ser Ser Phe Gly Asp Asp Arg Leu Leu Ile Glu Lys
            50                  55                  60
Phe Ile Asp Asn Pro Arg His Ile Glu Ile Gln Val Leu Gly Asp Lys

```
                65                        70                        75                        80
His  Gly  Asn  Ala  Leu  Trp  Leu  Asn  Glu  Arg  Glu  Cys  Ser  Ile  Gln  Arg
                         85                        90                        95

Arg  Asn  Gln  Lys  Val  Val  Glu  Glu  Ala  Pro  Ser  Ile  Phe  Leu  Asp  Pro
                    100                       105                       110

Glu  Thr  Arg  Arg  Ala  Met  Gly  Glu  Gln  Ala  Val  Ala  Trp  Pro  Lys  Ala
               115                       120                       125

Val  Lys  Tyr  Ser  Ser  Ala  Gly  Thr  Val  Glu  Phe  Leu  Val  Asp  Ser  Gln
          130                       135                       140
```

( 2 ) INFORMATION FOR SEQ ID NO:90:

( i ) SEQUENCE CHARACTERISTICS:
        ( A ) LENGTH: 48 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:90:

```
Lys  Asn  Phe  Tyr  Phe  Leu  Glu  Met  Asn  Thr  Arg  Leu  Gln  Val  Glu  His
                    5                         10                        15

Pro  Val  Thr  Glu  Cys  Ile  Thr  Gly  Leu  Asp  Leu  Val  Gln  Glu  Met  Ile
               20                        25                        30

Leu  Val  Ala  Lys  Gly  Tyr  Pro  Leu  Arg  His  Lys  Gln  Glu  Asp  Ile  Pro
          35                        40                        45
```

( 2 ) INFORMATION FOR SEQ ID NO:91:

( i ) SEQUENCE CHARACTERISTICS:
        ( A ) LENGTH: 29 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:91:

```
Ile  Ser  Gly  Trp  Ala  Val  Glu  Cys  Arg  Val  Tyr  Ala  Glu  Asp  Pro  Tyr
                    5                         10                        15

Lys  Ser  Phe  Gly  Leu  Pro  Ser  Ile  Gly  Arg  Leu  Ser  Gln
               20                        25
```

( 2 ) INFORMATION FOR SEQ ID NO:92:

( i ) SEQUENCE CHARACTERISTICS:
        ( A ) LENGTH: 14 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:92:

```
Tyr  Gln  Glu  Pro  Ile  His  Leu  Pro  Gly  Val  Arg  Val  Asp  Ser
                    5                         10
```

( 2 ) INFORMATION FOR SEQ ID NO:93:

( i ) SEQUENCE CHARACTERISTICS:
        ( A ) LENGTH: 44 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:93:

| Gly | Ile | Gln | Pro | Gly | Ser | Asp | Ile | Ser | Ile | Tyr | His | Asp | Pro | Met | Ile |
|---|---|---|---|---|---|---|---|---|---|---|---|---|---|---|---|
| | | | | 5 | | | | | 10 | | | | | 15 | |
| Ser | Lys | Leu | Val | Thr | Tyr | Gly | Ser | Asp | Arg | Ala | Glu | Ala | Leu | Lys | Arg |
| | | | 20 | | | | | 25 | | | | | 30 | | |
| Met | Glu | Asp | Ala | Leu | Asp | Ser | Tyr | Val | Ile | Arg | Gly | | | | |
| | | 35 | | | | | 40 | | | | | | | | |

( 2 ) INFORMATION FOR SEQ ID NO:94:

( i ) SEQUENCE CHARACTERISTICS:
( A ) LENGTH: 251 amino acids
( B ) TYPE: Amino acid
( C ) STRANDEDNESS: Single
( D ) TOPOLOGY: Linear ( i i ) MOLECULE TYPE: Peptide ( x i ) SEQUENCE DESCRIPTION: SEQ ID NO:94:

| Val | Thr | His | Asn | Ile | Pro | Leu | Leu | Arg | Glu | Val | Ile | Ile | Asn | Thr | Arg |
|---|---|---|---|---|---|---|---|---|---|---|---|---|---|---|---|
| | | | | 5 | | | | | 10 | | | | | 15 | |
| Phe | Val | Lys | Gly | Asp | Ile | Ser | Thr | Lys | Phe | Leu | Ser | Asp | Val | Tyr | Pro |
| | | | 20 | | | | | 25 | | | | | 30 | | |
| Asp | Gly | Phe | Lys | Gly | His | Met | Leu | Thr | Pro | Ser | Glu | Arg | Asp | Gln | Leu |
| | | 35 | | | | | 40 | | | | | 45 | | | |
| Leu | Ala | Ile | Ala | Ser | Ser | Leu | Phe | Val | Ala | Ser | Gln | Leu | Arg | Ala | Gln |
| | 50 | | | | | 55 | | | | | 60 | | | | |
| Arg | Phe | Gln | Glu | His | Ser | Arg | Val | Pro | Val | Ile | Arg | Pro | Asp | Val | Ala |
| 65 | | | | | 70 | | | | | 75 | | | | | 80 |
| Lys | Trp | Glu | Leu | Ser | Val | Lys | Leu | His | Asp | Glu | Asp | His | Thr | Val | Val |
| | | | | 85 | | | | | 90 | | | | | 95 | |
| Ala | Ser | Asn | Asn | Gly | Pro | Thr | Phe | Asn | Val | Glu | Val | Asp | Gly | Ser | Lys |
| | | | 100 | | | | | 105 | | | | | 110 | | |
| Leu | Asn | Val | Thr | Ser | Thr | Trp | Asn | Leu | Ala | Ser | Pro | Leu | Leu | Ser | Val |
| | | | 115 | | | | 120 | | | | | 125 | | | |
| Asn | Val | Asp | Gly | Thr | Gln | Arg | Thr | Val | Gln | Cys | Leu | Ser | Pro | Asp | Ala |
| | 130 | | | | | 135 | | | | | 140 | | | | |
| Gly | Gly | Asn | Met | Ser | Ile | Gln | Phe | Leu | Gly | Thr | Val | Tyr | Lys | Val | His |
| 145 | | | | | 150 | | | | | 155 | | | | | 160 |
| Ile | Leu | Thr | Lys | Leu | Ala | Ala | Glu | Leu | Asn | Lys | Phe | Met | Leu | Glu | Lys |
| | | | | 165 | | | | | 170 | | | | | 175 | |
| Val | Pro | Lys | Asp | Thr | Ser | Ser | Val | Leu | Arg | Ser | Pro | Lys | Pro | Gly | Val |
| | | | 180 | | | | | 185 | | | | | 190 | | |
| Val | Val | Ala | Val | Ser | Val | Lys | Pro | Gly | Asp | Met | Val | Ala | Glu | Gly | Gln |
| | | 195 | | | | | 200 | | | | | 205 | | | |
| Glu | Ile | Cys | Val | Ile | Glu | Ala | Met | Lys | Met | Gln | Asn | Ser | Met | Thr | Ala |
| | 210 | | | | | 215 | | | | | 220 | | | | |
| Gly | Lys | Met | Gly | Lys | Val | Lys | Leu | Val | His | Cys | Lys | Ala | Gly | Asp | Thr |
| 225 | | | | | 230 | | | | | 235 | | | | | 240 |
| Val | Gly | Glu | Gly | Asp | Leu | Leu | Val | Glu | Leu | Glu | | | | | |
| | | | | 245 | | | | | 250 | | | | | | |

( 2 ) INFORMATION FOR SEQ ID NO:95:

( i ) SEQUENCE CHARACTERISTICS:
( A ) LENGTH: 17 amino acids
( B ) TYPE: Amino acid -continued (C) STRANDEDNESS: Single
(D) TOPOLOGY: Linear (ii) MOLECULE TYPE: Peptide (xi) SEQUENCE DESCRIPTION: SEQ ID NO:95:

Gln Arg Lys Phe Ala Gly Leu Arg Asp Asn Phe Asn Leu Leu Gly Glu
                 5                  10                      15
Lys (2) INFORMATION FOR SEQ ID NO:96:

(i) SEQUENCE CHARACTERISTICS:
    (A) LENGTH: 34 amino acids
    (B) TYPE: Amino acid
    (C) STRANDEDNESS: Single
    (D) TOPOLOGY: Linear (ii) MOLECULE TYPE: Peptide (xi) SEQUENCE DESCRIPTION: SEQ ID NO:96:

Asn Lys Ile Leu Val Ala Asn Arg Gly Glu Ile Pro Ile Arg Ile Phe
                 5                  10                      15
Arg Thr Ala His Glu Leu Ser Met Gln Thr Val Ala Ile Tyr Ser His
            20                  25                  30
Glu Asp (2) INFORMATION FOR SEQ ID NO:97:

(i) SEQUENCE CHARACTERISTICS:
    (A) LENGTH: 24 amino acids
    (B) TYPE: Amino acid
    (C) STRANDEDNESS: Single
    (D) TOPOLOGY: Linear (ii) MOLECULE TYPE: Peptide (xi) SEQUENCE DESCRIPTION: SEQ ID NO:97:

Arg Leu Ser Thr His Lys Gln Lys Ala Asp Glu Ala Tyr Val Ile Gly
                 5                  10                      15
Glu Val Gly Gln Tyr Thr Pro Val
            20

(2) INFORMATION FOR SEQ ID NO:98:

(i) SEQUENCE CHARACTERISTICS:
    (A) LENGTH: 38 amino acids
    (B) TYPE: Amino acid
    (C) STRANDEDNESS: Single
    (D) TOPOLOGY: Linear (ii) MOLECULE TYPE: Peptide (xi) SEQUENCE DESCRIPTION: SEQ ID NO:98:

Gly Ala Tyr Leu Ala Ile Asp Glu Ile Ile Ser Ile Ala Gln Lys His
                 5                  10                      15
Gln Val Asp Phe Ile His Pro Gly Tyr Gly Phe Leu Ser Glu Asn Ser
            20                  25                  30
Glu Phe Ala Asp Lys Val
            35

(2) INFORMATION FOR SEQ ID NO:99:

(i) SEQUENCE CHARACTERISTICS:
    (A) LENGTH: 41 amino acids
    (B) TYPE: Amino acid (C) STRANDEDNESS: Single
(D) TOPOLOGY: Linear (ii) MOLECULE TYPE: Peptide (xi) SEQUENCE DESCRIPTION: SEQ ID NO:99:

| Val | Lys | Ala | Gly | Ile | Thr | Trp | Ile | Gly | Pro | Pro | Ala | Glu | Val | Ile | Asp |
|---|---|---|---|---|---|---|---|---|---|---|---|---|---|---|---|
| | | | | 5 | | | | | 10 | | | | | 15 | |
| Ser | Val | Gly | Asp | Lys | Val | Ser | Ala | Arg | Asn | Leu | Ala | Ala | Lys | Ala | Asn |
| | | | | 20 | | | | | 25 | | | | | 30 | |
| Val | Pro | Thr | Val | Pro | Gly | Thr | Pro | Gly | | | | | | | |
| | | | 35 | | | | | 40 | | | | | | | |

(2) INFORMATION FOR SEQ ID NO:100:

(i) SEQUENCE CHARACTERISTICS:
(A) LENGTH: 144 amino acids
(B) TYPE: Amino acid
(C) STRANDEDNESS: Single
(D) TOPOLOGY: Linear (ii) MOLECULE TYPE: Peptide (xi) SEQUENCE DESCRIPTION: SEQ ID NO:100:

| Ile | Glu | Thr | Val | Glu | Glu | Ala | Leu | Asp | Phe | Val | Asn | Glu | Tyr | Gly | Tyr |
|---|---|---|---|---|---|---|---|---|---|---|---|---|---|---|---|
| | | | | 5 | | | | | 10 | | | | | 15 | |
| Pro | Val | Ile | Ile | Lys | Ala | Ala | Phe | Gly | Gly | Gly | Arg | Gly | Met | Arg | |
| | | | | 20 | | | | | 25 | | | | | 30 | |
| Val | Val | Arg | Glu | Gly | Asp | Asp | Val | Ala | Asp | Ala | Phe | Gln | Arg | Ala | Thr |
| | | | 35 | | | | | 40 | | | | | 45 | | |
| Ser | Glu | Ala | Arg | Thr | Ala | Phe | Gly | Asn | Gly | Thr | Cys | Phe | Val | Glu | Arg |
| | | 50 | | | | | 55 | | | | | 60 | | | |
| Phe | Leu | Asp | Lys | Pro | Lys | His | Ile | Glu | Val | Gln | Leu | Leu | Ala | Asp | Asn |
| 65 | | | | | 70 | | | | | 75 | | | | | 80 |
| His | Gly | Asn | Val | Val | His | Leu | Phe | Glu | Arg | Asp | Cys | Ser | Val | Gln | Arg |
| | | | | 85 | | | | | 90 | | | | | 95 | |
| Arg | His | Gln | Lys | Val | Val | Glu | Val | Ala | Pro | Ala | Lys | Thr | Leu | Pro | Arg |
| | | | 100 | | | | | 105 | | | | | 110 | | |
| Glu | Val | Arg | Asp | Ala | Ile | Leu | Thr | Asp | Ala | Val | Lys | Leu | Ala | Lys | Glu |
| | | 115 | | | | | 120 | | | | | 125 | | | |
| Cys | Gly | Tyr | Arg | Asn | Ala | Gly | Thr | Ala | Glu | Phe | Leu | Val | Asp | Asn | Gln |
| | 130 | | | | | 135 | | | | | 140 | | | | |

(2) INFORMATION FOR SEQ ID NO:101:

(i) SEQUENCE CHARACTERISTICS:
(A) LENGTH: 51 amino acids
(B) TYPE: Amino acid
(C) STRANDEDNESS: Single
(D) TOPOLOGY: Linear (ii) MOLECULE TYPE: Peptide (xi) SEQUENCE DESCRIPTION: SEQ ID NO:101:

| Asn | Arg | His | Tyr | Phe | Ile | Glu | Ile | Asn | Pro | Arg | Ile | Gln | Val | Glu | His |
|---|---|---|---|---|---|---|---|---|---|---|---|---|---|---|---|
| | | | | 5 | | | | | 10 | | | | | 15 | |
| Thr | Ile | Thr | Glu | Glu | Ile | Thr | Gly | Ile | Asp | Ile | Val | Ala | Ala | Gln | Ile |
| | | | | 20 | | | | | 25 | | | | | 30 | |
| Gln | Ile | Ala | Ala | Gly | Ala | Ser | Leu | Pro | Gln | Leu | Gly | Leu | Phe | Gln | Asp |
| | | | 35 | | | | | 40 | | | | | 45 | | |
| Lys | Ile | Thr | | | | | | | | | | | | | |
| | | 50 | | | | | | | | | | | | | |

( 2 ) INFORMATION FOR SEQ ID NO:102:

( i ) SEQUENCE CHARACTERISTICS:
    ( A ) LENGTH: 20 amino acids
    ( B ) TYPE: Amino acid
    ( C ) STRANDEDNESS: Single
    ( D ) TOPOLOGY: Linear ( i i ) MOLECULE TYPE: Peptide ( x i ) SEQUENCE DESCRIPTION: SEQ ID NO:102:

```
Thr Arg Gly Phe Ala Ile Gln Cys Arg Ile Thr Thr Glu Asp Pro Ala
                 5                  10                  15
Lys Asn Phe Gln
         20
```

( 2 ) INFORMATION FOR SEQ ID NO:103:

( i ) SEQUENCE CHARACTERISTICS:
    ( A ) LENGTH: 14 amino acids
    ( B ) TYPE: Amino acid
    ( C ) STRANDEDNESS: Single
    ( D ) TOPOLOGY: Linear ( i i ) MOLECULE TYPE: Peptide ( x i ) SEQUENCE DESCRIPTION: SEQ ID NO:103:

```
Pro Asp Thr Gly Arg Ile Glu Val Tyr Arg Ser Ala Gly Gly
                 5                  10
```

( 2 ) INFORMATION FOR SEQ ID NO:104:

( i ) SEQUENCE CHARACTERISTICS:
    ( A ) LENGTH: 52 amino acids
    ( B ) TYPE: Amino acid
    ( C ) STRANDEDNESS: Single
    ( D ) TOPOLOGY: Linear ( i i ) MOLECULE TYPE: Peptide ( x i ) SEQUENCE DESCRIPTION: SEQ ID NO:104:

```
Asn Gly Val Arg Leu Asp Gly Gly Asn Ala Tyr Ala Gly Thr Ile Ile
                 5                  10                  15
Ser Pro His Tyr Asp Ser Met Leu Val Lys Cys Ser Cys Ser Gly Ser
                 20                  25                  30
Thr Tyr Glu Ile Val Arg Arg Lys Met Ile Arg Ala Leu Ile Glu Phe
                 35                  40                  45
Arg Ile Arg Gly
         50
```

( 2 ) INFORMATION FOR SEQ ID NO:105:

( i ) SEQUENCE CHARACTERISTICS:
    ( A ) LENGTH: 257 amino acids
    ( B ) TYPE: Amino acid
    ( C ) STRANDEDNESS: Single
    ( D ) TOPOLOGY: Linear ( i i ) MOLECULE TYPE: Peptide ( x i ) SEQUENCE DESCRIPTION: SEQ ID NO:105:

```
Val Lys Thr Asn Ile Pro Phe Leu Leu Thr Leu Leu Thr Asn Pro Val
                 5                  10                  15
Phe Ile Glu Gly Thr Tyr Trp Gly Thr Phe Ile Asp Asp Thr Pro Gln
                 20                  25                  30
```

```
Leu Phe Gln Met Val Ser Ser Gln Asn Arg Ala Gln Lys Leu Leu His
         35                  40                  45
Tyr Leu Ala Asp Val Ala Asp Asn Gly Ser Ser Ile Lys Gly Gln Ile
     50                  55                  60
Gly Leu Pro Lys Leu Lys Ser Asn Pro Ser Val Pro His Ser Tyr Asn
65                      70                  75                  80
Met Tyr Pro Arg Val Tyr Glu Asp Phe Gln Lys Met Arg Glu Thr Tyr
                 85                  90                  95
Gly Asp Leu Ser Val Leu Pro Thr Arg Ser Phe Leu Ser Pro Leu Glu
             100                 105                 110
Thr Asp Glu Glu Ile Glu Val Val Ile Glu Gln Gly Lys Thr Leu Ile
         115                 120                 125
Ile Lys Leu Gln Ala Val Gly Asp Leu Asn Lys Lys Thr Gly Glu Arg
     130                 135                 140
Glu Val Tyr Phe Asp Leu Asn Gly Glu Met Arg Lys Ile Arg Val Ala
145                 150                 155                 160
Asp Arg Ser Gln Lys Val Glu Thr Val Thr Lys Ser Lys Ala Asp Met
                 165                 170                 175
His Asp Pro Leu His Ile Gly Ala Pro Met Ala Gly Val Ile Val Glu
             180                 185                 190
Val Lys Val His Lys Gly Ser Leu Ile Lys Lys Gly Gln Pro Val Ala
         195                 200                 205
Val Leu Ser Ala Met Lys Met Glu Met Ile Ile Ser Ser Pro Ser Asp
     210                 215                 220
Gly Gln Val Lys Glu Val Phe Val Ser Asp Gly Glu Asn Val Asp Ser
225                 230                 235                 240
Ser Asp Leu Leu Val Leu Leu Glu Asp Gln Val Pro Val Glu Thr Lys
             245                 250                 255
Ala
```

( 2 ) INFORMATION FOR SEQ ID NO:106:

( i ) SEQUENCE CHARACTERISTICS:
      ( A ) LENGTH: 165 amino acids
      ( B ) TYPE: Amino acid
      ( C ) STRANDEDNESS: Single
      ( D ) TOPOLOGY: Linear ( i i ) MOLECULE TYPE: Peptide ( x i ) SEQUENCE DESCRIPTION: SEQ ID NO:106:

```
Val Leu Thr Val Ala Leu Phe Pro Gln Pro Gly Leu Lys Phe Leu Glu
                 5                  10                  15
Asn Arg His Asn Pro Ala Ala Phe Glu Pro Val Pro Gln Ala Glu Ala
             20                  25                  30
Ala Gln Pro Val Ala Lys Ala Glu Lys Pro Ala Ala Ser Gly Val Tyr
         35                  40                  45
Thr Val Glu Val Glu Gly Lys Ala Phe Val Val Lys Val Ser Asp Gly
     50                  55                  60
Gly Asp Val Ser Gln Leu Thr Ala Ala Pro Ala Pro Ala Pro Ala Pro
65                      70                  75                  80
Pro Ala Pro Ala Ser Ala Pro Ala Ala Ala Ala Pro Ala Gly Ala Gly
                 85                  90                  95
Thr Pro Val Thr Ala Pro Leu Ala Gly Thr Ile Trp Lys Val Leu Ala
             100                 105                 110
Ser Glu Gly Gln Thr Val Ala Ala Gly Glu Val Leu Leu Ile Leu Glu
         115                 120                 125
```

Ala Met Lys Met Glu Thr Glu Ile Arg Ala Ala Gln Ala Gly Thr Val
    130             135                 140

Arg Gly Ile Ala Val Lys Ala Gly Asp Ala Val Ala Val Gly Asp Thr
145             150                 155                 160

Leu Met Thr Leu Ala
            165

( 2 ) INFORMATION FOR SEQ ID NO:107:

( i ) SEQUENCE CHARACTERISTICS:
        ( A ) LENGTH: 123 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:107:

Met Lys Leu Lys Val Thr Val Asn Gly Thr Ala Tyr Asp Val Asp Val
            5                   10                  15

Asp Val Asp Lys Ser His Glu Asn Pro Met Gly Thr Ile Leu Phe Gly
            20                  25                  30

Gly Gly Thr Gly Gly Ala Pro Ala Pro Arg Ala Ala Gly Gly Ala Gly
            35                  40                  45

Ala Gly Lys Ala Gly Glu Gly Glu Ile Pro Ala Pro Leu Ala Gly Thr
    50                  55                  60

Val Ser Lys Ile Leu Val Lys Glu Gly Asp Thr Val Lys Ala Gly Gln
65                  70                  75                  80

Thr Val Leu Val Leu Glu Ala Met Lys Met Glu Thr Glu Ile Asn Ala
                85                  90                  95

Pro Thr Asp Gly Lys Val Glu Lys Val Leu Val Lys Glu Arg Asp Ala
            100                 105                 110

Val Gln Gly Gly Gln Gly Leu Ile Lys Ile Gly
            115                 120

( 2 ) INFORMATION FOR SEQ ID NO:108:

( i ) SEQUENCE CHARACTERISTICS:
        ( A ) LENGTH: 1473 base pairs
        ( B ) TYPE: Nucleic acid
        ( C ) STRANDEDNESS: Single
        ( D ) TOPOLOGY: Linear ( i i ) MOLECULE TYPE: Oligonucleotide ( x i ) SEQUENCE DESCRIPTION: SEQ ID NO:108:

```
GTGATGATCA AGGCATCATG GGGTGGGGGT GGTAAAGGAA TAAGGAAGGT ACATAATGAT    60
GATGAGGTCA GAGCATTGTT TAAGCAAGTG CAAGGAGAAG TCCCCGGATC GCCTATATTT   120
ATTATGAAGG TGGCATCTCA GAGTCGACAT CTAGAGGTTC AATTGCTCTG TGACAAGCAT   180
GGCAACGTGG CAGCACTGCA CAGTCGAGAC TGTAGTGTTC AAAGAAGGCA TCAAAAGATC   240
ATTGAGGAGG GACCAATTAC AGTTGCTCCT CCAGAAACAA TTAAAGAGCT TGAGCAGGCG   300
GCAAGGCGAC TAGCTAAATG TGTGCAATAT CAGGGTGCTG CTACAGTGGA ATATCTGTAC   360
AGCATGGAAA CAGGCGAATA CTATTTCCTG GAGCTTAATC CAAGGTTGCA GGTAGAACAC   420
CCTGTGACCG AATGGATTGC TGAAATAAAC TTACCYGCAT CTCAAGTTGT AGTAGGAATG   480
GGCATACCAC TCTACAACAT TCCAGAGATC AGACGCTTTT ATGGAATAGA ACATGGAGGT   540
GGCTATCAYG CTTGGAAGGA AATATCAGCT GTTGCAACTA AATTTGATYT GGACAAAGCA   600
```

-continued

| | | | | | |
|---|---|---|---|---|---|
| CAGTCTGTAA | AGCCAAARGG | TCATTGTGTA | GCAGTTAGAG | TTACTAGCGA | GGATCCAGAT | 660 |
| GATGGGTTTA | AGCCTACMAG | TGGAAGAGTR | GAAGAGCTGA | ACTTTAAAAG | TAAACCCAAT | 720 |
| GTTTGGGCCT | ATTTCTCYGT | TARGTCCGGA | GGTGCAATTC | AYGAGTTCTC | TGATTCCCAG | 780 |
| TTTGGTCATG | TTTTTGCTTY | TGGGGAATCT | AGGTCWTTGG | CAATAGCCAA | TATGGTACTT | 840 |
| GGGTTAAAAG | AGATCCAAAT | TCGTGGAGAG | ATACGCACTA | ATGTTGACTA | CACTGTGGAT | 900 |
| CTCTTGAATG | CTGCAGAGTA | CCGAGAAAAT | AWGATTCACA | CTGGTTGGCT | AGACAGCAGA | 960 |
| ATAGCWATGC | GYGTTAGAGC | AGAGAGGCCC | CCATGGTACC | TTTCAGTTGT | TGGTGGAGCT | 1020 |
| CTATATGAAG | CATCAAGCAG | GAGCTCGAGT | GTTGTAACCG | ATTATGTTGG | TTATCTCAGT | 1080 |
| AAAGGTCAAA | TACCACCAAA | GCACATCTCT | CTTGTCAAYT | TGACTGTAAC | ACTGAATATA | 1140 |
| GATGGGAGCA | AATATACGAT | TGAGACAGTA | CGAGGTGGAC | CCCGTAGCTA | CAAATTAAGA | 1200 |
| ATTAATGAAT | CAGAGGTTGA | RGCAGAGATA | CATTTCCTGC | GAGATGGCGG | ACYCTTAATG | 1260 |
| CAGTYGGATG | GAAACAGTCA | TGTAATTTAC | GCCGAGACAG | AAGCTKCTGG | CACGCGCCTT | 1320 |
| CTAATCAATG | GGAGAACATG | CTTATTACAG | AAAGAGCAYG | ATCCTTCCAG | GTTGTTGGCT | 1380 |
| GATACACCRT | GCAARCTTCT | TCGGTTTTTG | GTCGCGGATR | GTTCTCATGT | GGTTGCTGAT | 1440 |
| ACGCCATATG | CYGAGGTGGA | GGCCATGAAA | ATG | | | 1473 |

(2) INFORMATION FOR SEQ ID NO:109:

(i) SEQUENCE CHARACTERISTICS:
     (A) LENGTH: 491 amino acids
     (B) TYPE: Amino acid
     (C) STRANDEDNESS: Single
     (D) TOPOLOGY: Linear (ii) MOLECULE TYPE: Peptide (ix) FEATURE:
     (A) NAME/KEY: Xaa
     (B) LOCATION: 248, 267, 311, 412, 418, 422, 436, and 474
     (C) IDENTIFICATION METHOD: Xaa =any amino acid (xi) SEQUENCE DESCRIPTION: SEQ ID NO:109:

```
Val Met Ile Lys Ala Ser Trp Gly Gly Gly Gly Lys Gly Ile Arg Lys
                 5                  10                  15
Val His Asn Asp Asp Glu Val Arg Ala Leu Phe Lys Gln Val Gln Gly
             20                  25                  30
Glu Val Pro Gly Ser Pro Ile Phe Ile Met Lys Val Ala Ser Gln Ser
         35                  40                  45
Arg His Leu Glu Val Gln Leu Leu Cys Asp Lys His Gly Asn Val Ala
     50                  55                  60
Ala Leu His Ser Arg Asp Cys Ser Val Gln Arg Arg His Gln Lys Ile
 65                  70                  75                  80
Ile Glu Glu Gly Pro Ile Thr Val Ala Pro Pro Glu Thr Ile Lys Glu
                 85                  90                  95
Leu Glu Gln Ala Ala Arg Arg Leu Ala Lys Cys Val Gln Tyr Gln Gly
            100                 105                 110
Ala Ala Thr Val Glu Tyr Leu Tyr Ser Met Glu Thr Gly Glu Tyr Tyr
        115                 120                 125
Phe Leu Glu Leu Asn Pro Arg Leu Gln Val Glu His Pro Val Thr Glu
    130                 135                 140
Trp Ile Ala Glu Ile Asn Leu Pro Ala Ser Gln Val Val Val Gly Met
145                 150                 155                 160
Gly Ile Pro Leu Tyr Asn Ile Pro Glu Ile Arg Arg Phe Tyr Gly Ile
                165                 170                 175
```

```
Glu His Gly Gly Gly Tyr His Ala Trp Lys Glu Ile Ser Ala Val Ala
            180                 185                 190
Thr Lys Phe Asp Leu Asp Lys Ala Gln Ser Val Lys Pro Lys Gly His
        195                 200                 205
Cys Val Ala Val Arg Val Thr Ser Glu Asp Pro Asp Gly Phe Lys
        210                 215                 220
Pro Thr Ser Gly Arg Val Glu Glu Leu Asn Phe Lys Ser Lys Pro Asn
225                     230                 235                 240
Val Trp Ala Tyr Phe Ser Val Xaa Ser Gly Ala Ile His Glu Phe
                245                 250                 255
Ser Asp Ser Gln Phe Gly His Val Phe Ala Xaa Gly Glu Ser Arg Ser
            260                 265                 270
Leu Ala Ile Ala Asn Met Val Leu Gly Leu Lys Glu Ile Gln Ile Arg
            275                 280                 285
Gly Glu Ile Arg Thr Asn Val Asp Tyr Thr Val Asp Leu Leu Asn Ala
    290                 295                 300
Ala Glu Tyr Arg Glu Asn Xaa Ile His Thr Gly Trp Leu Asp Ser Arg
305                 310                 315                 320
Ile Ala Met Arg Val Arg Ala Glu Arg Pro Pro Trp Tyr Leu Ser Val
                325                 330                 335
Val Gly Gly Ala Leu Tyr Glu Ala Ser Ser Arg Ser Ser Ser Val Val
            340                 345                 350
Thr Asp Tyr Val Gly Tyr Leu Ser Lys Gly Gln Ile Pro Pro Lys His
        355                 360                 365
Ile Ser Leu Val Asn Leu Thr Val Thr Leu Asn Ile Asp Gly Ser Lys
    370                 375                 380
Tyr Thr Ile Glu Thr Val Arg Gly Gly Pro Arg Ser Tyr Lys Leu Arg
385                 390                 395                 400
Ile Asn Glu Ser Glu Val Glu Ala Glu Ile His Xaa Leu Arg Asp Gly
                405                 410                 415
Gly Xaa Leu Met Gln Xaa Asp Gly Asn Ser His Val Ile Tyr Ala Glu
            420                 425                 430
Thr Glu Ala Xaa Gly Thr Arg Leu Leu Ile Asn Gly Arg Thr Cys Leu
        435                 440                 445
Leu Gln Lys Glu His Asp Pro Ser Arg Leu Leu Ala Asp Thr Pro Cys
    450                 455                 460
Lys Leu Leu Arg Phe Leu Val Ala Asp Xaa Ser His Val Val Ala Asp
465                 470                 475                 480
Thr Pro Tyr Ala Glu Val Glu Ala Met Lys Met
                485                 490
```

( 2 ) INFORMATION FOR SEQ ID NO:110:

( i ) SEQUENCE CHARACTERISTICS:
        ( A ) LENGTH: 436 base pairs
        ( B ) TYPE: Nucleic acid
        ( C ) STRANDEDNESS: Single
        ( D ) TOPOLOGY: Linear ( i i ) MOLECULE TYPE: Oligonucleotide ( x i ) SEQUENCE DESCRIPTION: SEQ ID NO:110:

```
TCTAGACTTT AACGAGATTC GTCAACTGCT GACAACTATT GCACAAACAG ATATCGCGGA      60
AGTAACGCTC AAAAGTGATG ATTTTGAACT AACGGTGCGT AAAGCTGTTG GTGTGAATAA     120
TAGTGTTGTG CCGGTTGTGA CAGCACCCTT GAGTGGTGTG GTAGGTTCGG GATTGCCATC     180
```

```
GGCTATACCG ATTGTAGCCC ATGCTGCCCA ATCTCCATCT CCAGAGCCGG GAACAAGCCG      240

TGCTGCTGAT CATGCTGTCA CGAGTTCTGG CTCACAGCCA GGAGCAAAAA TCATTGACCA      300

AAAATTAGCA GAAGTGGCTT CCCCAATGGT GGGAACATTT TACCGCGCTC CTGCACCAGG      360

TGAAGCGGTA TTTGTGGAAG TCGGCGATCG CATCCGTCAA GGTCAAACCG TCTGCATCAT      420

CGAAGCGATG AAAAUG                                                     436
```

( 2 ) INFORMATION FOR SEQ ID NO:111:

( i ) SEQUENCE CHARACTERISTICS:
        ( A ) LENGTH: 145 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:111:

```
Leu Asp Phe Asn Glu Ile Arg Gln Leu Leu Thr Thr Ile Ala Gln Thr
                  5                  10                  15

Asp Ile Ala Glu Val Thr Leu Lys Ser Asp Asp Phe Glu Leu Thr Val
             20                  25                  30

Arg Lys Ala Val Gly Val Asn Asn Ser Val Val Pro Val Thr Ala
         35                  40                  45

Pro Leu Ser Gly Val Val Gly Ser Gly Leu Pro Ser Ala Ile Pro Ile
     50                  55                  60

Val Ala His Ala Ala Pro Ser Pro Ser Pro Glu Pro Gly Thr Ser Arg
65                  70                  75                  80

Ala Ala Asp His Ala Val Thr Ser Ser Gly Ser Gln Pro Gly Ala Lys
             85                  90                  95

Ile Ile Asp Gln Lys Leu Ala Glu Val Ala Ser Pro Met Val Gly Thr
             100                 105                 110

Phe Tyr Arg Ala Pro Ala Pro Gly Glu Ala Val Phe Val Glu Val Gly
         115                 120                 125

Asp Arg Ile Arg Gln Gly Gln Thr Val Cys Ile Ile Glu Ala Met Lys
     130                 135                 140

Met
145
```

( 2 ) INFORMATION FOR SEQ ID NO:112:

( i ) SEQUENCE CHARACTERISTICS:
        ( A ) LENGTH: 22 base units
        ( B ) TYPE: Nucleic acid
        ( C ) STRANDEDNESS: Single
        ( D ) TOPOLOGY: Linear ( i i ) MOLECULE TYPE: Oligonucleotide ( i x ) FEATURE:
        ( A ) NAME/KEY: N
        ( B ) LOCATION: 11, 14
        ( C ) IDENTIFICATION METHOD: N =A, G, C, T ( x i ) SEQUENCE DESCRIPTION: SEQ ID NO:112:

```
TCGAATTCGT NATNATHAAR GC                                               22
```

( 2 ) INFORMATION FOR SEQ ID NO:113:

( i ) SEQUENCE CHARACTERISTICS:
        ( A ) LENGTH: 22 base pairs
        ( B ) TYPE: Nucleic acid
        ( C ) STRANDEDNESS: Single ( D ) TOPOLOGY: Linear ( i i ) MOLECULE TYPE: Oligonucleotide ( i x ) FEATURE:
            ( A ) NAME/KEY: N
            ( B ) LOCATION: 17
            ( C ) IDENTIFICATION METHOD: N =A, G, C, T ( x i ) SEQUENCE DESCRIPTION: SEQ ID NO:113:

GCTCTAGAGK RTGYTCNACY TC 22

( 2 ) INFORMATION FOR SEQ ID NO:114:

( i ) SEQUENCE CHARACTERISTICS:
            ( A ) LENGTH: 21 base pairs
            ( B ) TYPE: Nucleic acid
            ( C ) STRANDEDNESS: Single
            ( D ) TOPOLOGY: Linear ( i i ) MOLECULE TYPE: Oligonucleotide ( x i ) SEQUENCE DESCRIPTION: SEQ ID NO:114:

GCTCTAGAAT ACTATTTCCT G 21

( 2 ) INFORMATION FOR SEQ ID NO:115:

( i ) SEQUENCE CHARACTERISTICS:
            ( A ) LENGTH: 22 base pairs
            ( B ) TYPE: Nucleic acid
            ( C ) STRANDEDNESS: Single
            ( D ) TOPOLOGY: Linear ( i i ) MOLECULE TYPE: Oligonucleotide ( i x ) FEATURE:
            ( A ) NAME/KEY: N
            ( B ) LOCATION: 10, 20
            ( C ) IDENTIFICATION METHOD: N =A, G, C, T ( x i ) SEQUENCE DESCRIPTION: SEQ ID NO:115:

TCGAATTCWN CATYTTCATN RC 22

( 2 ) INFORMATION FOR SEQ ID NO:116:

( i ) SEQUENCE CHARACTERISTICS:
            ( A ) LENGTH: 23 base pairs
            ( B ) TYPE: Nucleic acid
            ( C ) STRANDEDNESS: Single
            ( D ) TOPOLOGY: Linear ( i i ) MOLECULE TYPE: Oligonucleotide ( x i ) SEQUENCE DESCRIPTION: SEQ ID NO:116:

GCTCTAGAYT TYAAYGARAT HMG 23

CYANOBACTERIAL AND PLANT ACETYL-COA CARBOXYLASE

This is a continuation of application Ser. No. 07/956,700 filed Oct. 2, 1992, U.S. Pat. No. 5,539,092.

The United States Government has a certain rights in the present invention pursuant to Grant No. 90-34190-5207 from the Unite States Department of Agriculture through the midwest biotechnology consortium.

TECHNICAL FIELD OF THE INVENTION

The present invention relates to polynucleotides and polypeptides of acetyl-CoA carboxylase in cyanobacteria and plants. Polynucleotides encoding acetyl-CoA carboxylase have use in conferring herbicide resistance and in determining the herbicide resistance of plants in a breeding program.

BACKGROUND OF THE INVENTION

Acetyl-CoA carboxylase (ACC) is the first enzyme of the biosynthetic pathway to fatty acids. It belongs to a group of carboxylases that use biotin as cofactor and bicarbonate as a source of the carboxyl group. ACC catalyzes the addition of $CO_2$ to acetyl-CoA to yield malonyl-CoA in two steps as shown below.

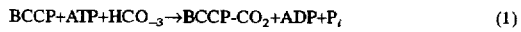

$$BCCP + ATP + HCO_{-3} \rightarrow BCCP\text{-}CO_2 + ADP + P_i \quad (1)$$

$$BCCP\text{-}CO_2 + \text{Acetyl-CoA} \rightarrow BCCP + \text{malonyl-CoA} \quad (2)$$

First, biotin becomes carboxylated at the expense of ATP. The carboxyl group is then transferred to Ac-CoA [Knowles, 1989]. This irreversible reaction is the committed step in fatty acid synthesis and is a target for multiple regulatory mechanisms. Reaction (1) is catalyzed by biotin carboxylase (BC); reaction (2) by transcarboxylase (TC); BCCP=biotin carboxyl carrier protein.

ACC purified from *E.coli* contains three distinct, separable components: biotin carboxylase (BC), a dimer of 49-kD monomers, biotin carboxyl carrier protein (BCCP) a dimer of 17-kD monomers and transcarboxylase (TC), a tetramer containing two each of 33-kd) and 35-kD subunits. The biotin prosthetic group is covalently attached to the γ-amino group of a lysine residue of BCCP. The primary structure of *E.coli* BCCP and BC is known (fabE and fabG genes,respectively, have been cloned and sequenced) [Alix, 1989; Maramatsu, et al., 1989; Li, et al., 1992]. In bacteria, fatty acids are primarily precursors of phospholipids rather than storage fuels, and so ACC activity is coordinated with cell growth and division.

Rat and chicken ACC consist of a dimer of about 265 kD (rat has also a 280 kD isoform) subunits that contains all of the bacterial enzyme activities. Both mammalian and avian ACC are cytoplasmic enzymes and their substrate is transported out of mitochondria via citrate. ACC content and/or activity varies with the rate of fatty acid synthesis or energy requirements in different nutritional, hormonal and developmental states. ACC mRNA is transcribed using different promoters and can be regulated by alternative splicing. ACC catalytic activity is regulated allosterically by a number of metabolites and by reversible phosphorylation of the enzyme. The primary structure of rat and chicken enzymes, and the primary structure of the 5'-untranslated region of mRNA have been deduced from cDNA sequences [Lopez-Casillas, et al., 1988; Takai, et al., 1988]. The primary structure of yeast ACC has also been determined [Feel, et al., 1992].

Studies on plant ACC are far less advanced [Harwood, 1988]. It was originally thought that plant ACC consisted of low molecular weight dissociable subunits similar to those of bacteria. Those results appeared to be due to degradation of the enzyme during purification. More recent results indicate that the wheat enzyme, as well as those from parsley and rape, are composed of two about 220 kD monomers, similar to the enzyme from rat and chicken [Harwood, 1988; Egin-Buhler, et al., 1983; Wurtelle, et al., 1990; Slabas, et al., 1985]. The plant ACC is located entirely in the stroma of plastids, where all plant fatty acid synthesis occurs. No plant gene encoding ACC has been reported to date. The gene must be nuclear because no corresponding sequence is seen in the complete chloroplast DNA sequences of tobacco, liverwort or rice. ACC, like the vast majority of chloroplast proteins which are encoded in nuclear DNA, must be synthisized in the cytoplasm and then transported into the chloroplast, probably requiring a chloroplast transport sequence. Although the basic features of plant ACC must be the same as those of prokaryotic and other eucaryotic ACCs, significant differences can be also expected due, for example, to differences in plant cell metabolism and ACC cellular localization.

Structural similarities deduced from the available amino acid sequences suggest strong evolutionary conservation among biotin carboxylases and biotin carboxylase domains of all biotin-dependent carboxylases. On the contrary, the BCCP domains show very little conservation outside the sequence E(A/V)MKM (lysine residue is biotinylated) which is found in all biotinylated proteins including pyruvate carboxylase and propionyl-CoA carboxylase [Knowles, 1989; Samols, et al., 1988]. It is likely that the three functional domains of ACC located in *E. coli on* separate polypeptides are present in carboxylases containing two (human propionyl-CoA carboxylase) or only one (yeast pyruvate carboxylase, mammalian, avian and probably also plant ACC) polypeptide as a result of gene fusion during evolution.

Several years ago it was shown that aryloxyphenoxypropionates and cyclohexanediones, powerful herbicides effective against monocot weeds, inhibit fatty acid biosynthesis in sensitive plants. Recently it has been determined that ACC is the target enzyme for both of these classes of herbicide. Dicotyledonous plants are resistant to these compounds, as are other eukaryotes and prokaryotes. The mechanisms of inhibition and resistance of the enzyme are not known [Lichtenthaler, 1990].

It has occurred to others that the evolutionary relatedness of cyanobacteria and plants make the former useful sources of cloned genes for the isolation of plant cDNAs. For example, Pecker et al used the cloned gene for the enzyme phytoene desaturase, which functions in the synthesis of carotenoids, from cyanobacteria as a probe to isolate the cDNA for that gene from tomato [Pecker, et al., 1992].

BRIEF SUMMARY OF THE INVENTION

In one aspect the present invention provides an isolated and purified polynucleotide of from about 1350 to about 40,000 base pairs that encodes a polypeptide having the ability to catalyze the carboxylation of a biotin carboxyl carrier protein of a cyanobacterium. Preferably, that polypeptide is a subunit of acetyl-CoA carboxylase and participates in the carboxylation of acetyl-CoA. In a preferred embodiment, a cyanobacterium is Anabaena or Synechococcus. The biotin carboxyl carrier protein preferably includes the amino acid residue sequence shown in SEQ ID NO: 111 or a functional equivalent thereof.

In another preferred embodiment, the polypeptide has the amino acid residue sequence of FIG. 1 or FIG. 2. The polynucleotide preferably includes the DNA sequence of SEQ ID NO:1, the DNA sequence of SEQ ID NO:1 from about nucleotide position 1300 to about nucleotide position 2650 or the DNA sequence of SEQ ID NO:5.

In another aspect, the present invention provides an isolated and purified polynucleotide of from about 480 to about 40,000 base pairs that encodes a biotin carboxyl carrier protein of a cyanobacterium and, preferably Anabaena. The biotin carboxyl carrier protein preferably includes the amino acid residue sequence of SEQ ID NO:111 and the polynucleotide preferably includes the DNA sequence of SEQ ID NO:110.

Another polynucleotide provided by the present invention encodes a plant polypeptide having the ability to catalyze the carboxylation of acetyl-CoA. A plant polypeptide is preferably (1) a monocotyledonous plant polypeptide such as a wheat, rice, maize, barley, rye, oats or timothy grass polypeptide or (2) a dicotyledonous plant polypeptide such as a soybean, rape, sunflower, tobacco, Arabiodopsis, petunia, Canola, pea, bean, tomato, potato, lettuce, spinach, alfalfa, cotton or carrot polypeptide. Preferably, that polypeptide is a subunit of ACC and participates in the carboxylation of acetyl-CoA.

Such a polynucleotide preferably includes the nucleotide sequence of SEQ ID NO:108 and encodes the amino acid residue sequence of SEQ ID NO:109.

In yet another aspect, the present invention provides an isolated and purified DNA molecule comprising a promoter operatively linked to a coding region that encodes (1) a polypeptide having the ability to catalyze the carboxylation of a biotin carboxyl carrier protein of a cyanobacterium, (2) a biotin carboxyl carrier protein of a cyanobacterium or (3) a plant polypeptide having the ability to catalyze the carboxylation of acetyl-CoA, which coding region is operatively linked to a transcription-terminating region, whereby said promoter drives the transcription of said coding region.

In another aspect, the present invention provides an isolated polypeptide having the ability to catalyze the carboxylation of a biotin carboxyl carrier protein of a cyanobacterium such as Anabaena or Synechococcus. Preferably a biotin carboxyl carrier protein includes the amino acid sequence of SEQ ID NO:111 and the polypeptide has the amino acid residue sequence of FIG. 1 or FIG. 2 (SEQ ID NOS:5 and 6).

The present invention also provides (1) an isolated and purified biotin carboxyl carrier protein of a cyanobacterium such as Anabaena, which protein includes the amino acid residue sequence of SEQ ID NO:111 and (2) an isolated and purified plant polypeptide having a molecular weight of about 220 kD, dimers of which have the ability to catalyze the carboxylation of acetyl-CoA.

In yet another aspect, the present invention provides a process of increasing the herbicide resistance of a monocotyledonous plant comprising transforming the plant with a DNA molecule comprising a promoter operatively linked to a coding region that encodes a herbicide resistant polypeptide having the ability to catalyze the carboxylation of acetyl-CoA, which coding region is operatively linked to a transcription-terminating region, whereby the promoter is capable of driving the transcription of the coding region in a monocotyledonous plant.

Preferably, a polypeptide is an acetyl-CoA carboxylase enzyme and, more preferably, a dicotyledonous plant acetyl-CoA carboxylase. In a preferred embodiment, a coding region includes the DNA sequence of SEQ ID NO:108 and a promoter is CaMV35.

The present invention also provides a transformed plant produced in accordance with the above process as well as a transgenic plant and a transgenic plant seed having incorporated into its genome a transgene that encodes a herbicide resistant polypeptide having the ability to catalyze the carboxylation of acetyl-CoA.

In yet another aspect, the present invention provides a process of altering the carboxylation of acetyl-CoA in a cell comprising transforming the cell with a DNA molecule comprising a promoter operatively linked to a coding region that encodes a plant polypeptide having the ability to catalyze the carboxylation of acetyl-CoA, which coding region is operatively linked to a transcription-terminating region, whereby the promoter is capable of driving the transcription of the coding region in the cell.

In a preferred embodiment, a cell is a cyanobacterium or a plant cell and a plant polypeptide is a monocotyledonous plant acetyl-CoA carboxylase enzyme such as wheat acetyl-CoA carboxylase enzyme. The present invention also provides a transformed cyanobacterium produced in accordance with such a process.

The present invention still further provides a process for determining the inheritance of plant resistance to herbicides of the aryloxyphenocypropionate or cyclohexanedione class, which process comprises the steps of:
(a) measuring resistance to herbicides of the aryloxyphenocypropionate or cyclohexanedione class in a parental plant line and in progeny of the parental plant line;
(b) purifying DNA from said parental plant line and the progeny;
(c) digesting the DNA with restriction enzymes to form DNA fragments;
(d) fractionating the fragments on a gel;
(e) transferring the fragments to a filter support;
(f) annealing the fragments with a labelled RFLP probe consisting of a DNA molecule that encodes acetyl-CoA carboxylase or a portion thereof; and
(g) detecting the presence of complexes between the fragments and the RFLP probe; and
(h) correlating the herbicide resistance of step (a) with the complexes of step (g) and thereby the inheritance of herbicide resistance.

Preferably, the acetyl-CoA carboxylase is a dicotyledonous plant acetyl-CoA carboxylase enzyme or a mutated monocotyledonous plant acetyl-CoA carboxylase that confers herbicide resistance or a hybrid acetyl-CoA carboxylase comprising a portion of a dicotyledonous plant acetyl-CoA carboxylase, a portion of a dicotyledonous plant acetyl-CoA carboxylase or one or more domains of a cyanobacterial acetyl-CoA carboxylase.

In still yet another aspect, the present invention provides a process for identifying herbicide resistant variants of a plant acetyl-CoA carboxylase comprising the steps of:
(a) transforming cyanobacteria with a DNA molecule that encodes a monocotyledonous plant acetyl-CoA carboxylase enzyme to form transformed cyanobacteria;
(b) inactivating cyanobacterial acetyl-CoA carboxylase;
(c) exposing the transformed cyanobacteria to a herbicide that inhibits acetyl-CoA carboxylase activity;
(d) identifying transformed cyanobacteria that are resistant to the herbicide; and
(e) characterizing DNA that encodes acetyl-CoA carboxylase from the cyanobacteria of step (d).

BRIEF DESCRIPTION OF THE DRAWINGS

In the drawings which form a portion of the specification:

FIGS. 1A–1B show the complete nucleotide sequence of a HindIII fragment that includes the fabG gene coding biotin carboxylase from the cyanobacterium Anabaena 7120, along with the amino acid sequence deduced from the coding sequence of the DNA.

FIGS. 2A–2C show the nucleotide sequence of the coding region of the fabG gene from the cyanobacterium Anacystis nidulans R2, along with the amino acid sequence deduced from the coding sequence of the DNA.

FIGS. 3A–3G show an alignment of the amino acid sequences of the BC proteins from both cyanobacteria and from *E. coli*, the BCCP proteins from Anabaena and from *E. coli*, along with the ACC enzymes from rat and chicken and several other biotin-containing carboxylases. Stars indicate positions that are identical in all sequences or all but one. The conventional one letter abbreviations for amino acids are used. The BC domains are indicated by a solid underline, the BCCP domains by a dashed underline. The symbol # indicates sequences not related to BC and, therefore, not considered in the alignment. The wheat ACC sequence deduced from the sequence of our cloned cDNA fragment is on the top line. Abbreviations used in the Figure are: Wh ACC, wheat ACC; Rt, rat; Ch, chicken; Yt, yeast; Sy ACC, Synechococcus BC; An ACC, Anabaena BC and BCCP proteins; EC ACC, *E. coli* BC and BCCP; Hm PCCA, human propionyl CoA carboxylase; Rt PCCA, rat propionyl CoA carboxylase; Yt PC, yeast pyruvate carboxylase.

FIGS. 6A–6B show the nucleotide sequence of a portion of the wheat cDNA corresponding to ACC. The amino acid sequence deduced from the nucleotide sequence is also shown. The underlined sequences correspond to the primer sites shown in FIG. 5. A unique sequence was found for the BC domain, suggesting that a single mRNA was the template for the final amplified products. For the sequence between the BC and BCCP domains, three different variants were found among four products sequenced, suggesting that three different gene transcripts were among the amplified products. This is not unexpected because wheat is hexaploid, i.e. it has three pairs of each chromosome.

FIG. 8 shows the nucleotide sequence of a PCR product corresponding to a portion of the fabE gene encoding about 75% of the biotin carboxyl carrier protein from the cyanobacterium Anabaena, along with the amino acid sequence deduced from the coding sequence. The underlined sequences correspond to the primer sites shown in FIG. 7.

DETAILED DESCRIPTION OF THE INVENTION

I. Definitions

Figure 4:
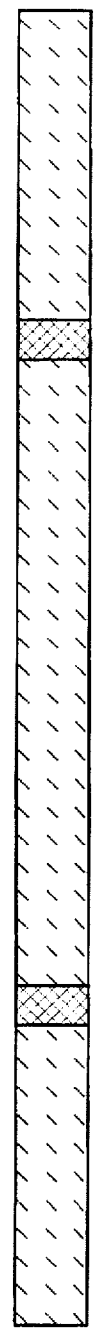
FIG. 4 shows the conserved amino acid sequences used to design primers for the PCR to amplify the BC domain of ACC from wheat. The sequences of the oligonucleotide primers are also shown. In this and other figures showing primer sequences, A means adenine, C means cytosine, G means guanine, T means thymine, N means all four nucleotides, Y means T or C, R means A or G, K means G or T, M means A or C, W means A or T, and H means A, C or T.

The following words and phrases have the meanings set forth below.

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g. plant protoplast or explant).

Structural gene: A gene that is expressed to produce a polypeptide.

Transformation: A process of introducing an exogenous DNA sequence (e.g. a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g. somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

Certain polypeptides are disclosed herein as amino acid residue sequences. Those sequences are written left to right in the direction from the amino to the carboxy terminus. In accordance with standard nomenclature, amino acid residue sequences are denominated by either a single letter or a three letter code as indicated below.

| Amino Acid Residue | 3-Letter Code | 1-Letter Code |
| --- | --- | --- |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |

| Amino Acid Residue | 3-Letter Code | 1-Letter Code |
| --- | --- | --- |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The present invention provides polynucleotides and polypeptides relating to a whole or a portion of acetyl-CoA carboxylase (ACC) of cyanobacteria and plants as well as processes using those polynucleotides and polypeptides.

II. Polynucleotides

As used herein the term "polynucleotide" means a sequence of nucleotides connected by phosphodiester linkages. A polynucleotide of the present invention can comprise from about 2 to about several hundred thousand base pairs. Preferably, a polynucleotide comprises from about 5 to about 150,000 base pairs. Preferred lengths of particular polynucleotides are set hereinafter.

A polynucleotide of the present invention can be a deoxyribonucleic acid (DNA) molecule or a ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), and uracil (U).

A. Cyanobacteria

In one embodiment, the present invention contemplates an isolated and purified polynucleotide of from about 1350 to about 40,000 base pairs that encodes a polypeptide having the ability to catalyze the carboxylation of a biotin carboxyl carrier protein of a cyanobacterium.

Preferably, a biotin carboxyl carrier protein (BCCP) is derived from a cyanobacterium such as Anabaena or Synechococcus. A preferred Anabaena is Anabaena 7120. A preferred Synechococcus is *Anacystis nidulans* R2 (Synechococcus sp. strain pcc7942). A biotin carboxyl carrier protein preferably includes the amino acid residue sequence shown in SEQ ID NO:111 or a functional equivalent thereof.

Figure 1A:
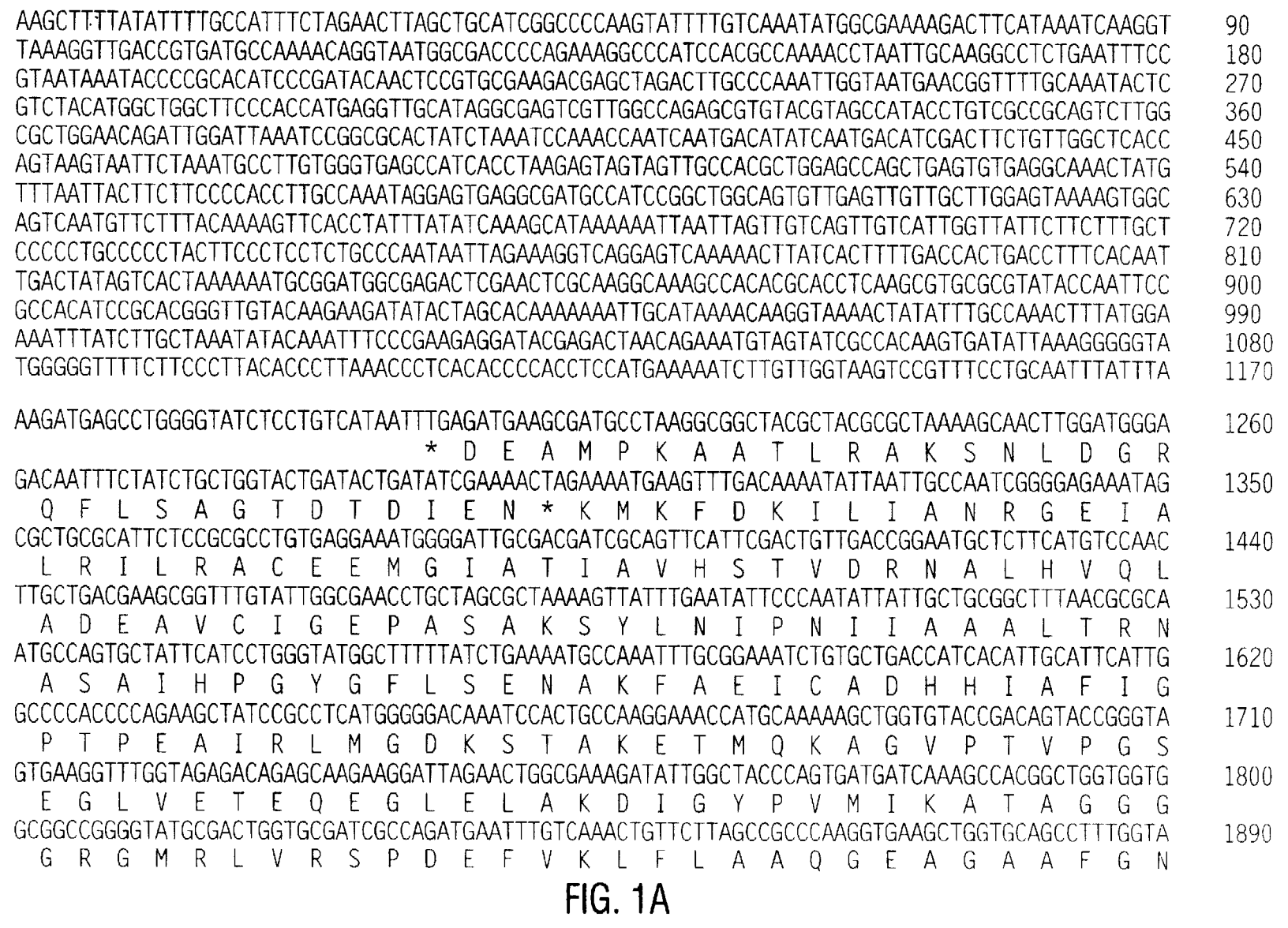

Preferably, a polypeptide is a biotin carboxylase enzyme of a cyanobacterium, which enzyme is a subunit of acetyl-CoA carboxylase and participates in the carboxylation of acetyl-CoA. In a preferred embodiment, a polypeptide encoded by such a polynucleotide has the amino acid residue sequence of FIG. 1 or FIG. 2, (SEQ NOS:5 and 6) or a functional equivalent of those sequences.

A polynucleotide preferably includes the DNA sequence of SEQ ID NO:1 (FIG. 1) or the DNA sequence of SEQ ID NO:1 (FIG. 1) from about nucleotide position 1300 to about nucleotide position 2650.

The polynucleotide of SEQ ID NO:1 contains a gene that encodes the enzyme biotin carboxylase (BC) from the cyanobacterium Anabaena. This gene was cloned in the following way: total DNA from Anabaena was digested with various restriction enzymes, fractionated by gel electrophoresis, and blotted onto GeneScreen Plus (DuPont). The blot was hybridized at low stringency (1 M NaCl, 57° C.) with a probe consisting of a SstII-PstI fragment containing about 90% of the coding region of the fabG gene from *E. coli*. This probe identified a 3.1-kb HindIII fragment in the Anabaena digest that contained similar sequences. A mixture of about 3-kb HindIII fragments of Anabaena DNA was purified, then digested with NheI, yielding a HindIII-NheI fragment of 1.6 kb that hybridized with the fabG probe. The 1.6kb region was purified by gel electrophoresis and cloned into pUC18.

Plasmid minipreps were made from about 160 colonies, of which four were found to contain the 1.6-kb HindIII-NheI fragment that hybridized with the fabG probe. The 1.6-kb Anabaena fragment was then used as probe to screen, at high stringency (1M NaCl, 65° C.), a cosmid library of Anabaena DNA inserts averaging 40 kb in size. Five were found among 1920 tested, all of which contained the same size HindIII and NheI fragments as those identified by the *E. coli* probe previously. From one of the cosmids, the 3.1-kb HindIII fragment containing the Anabaena fabG gene was subcloned into pUC18 and sequenced using the dideoxy chain termination method. The complete nucleotide sequence of this fragment is shown in FIG. 1 (SEQ ID NOS: 1 and 2).

A similar procedure was used to clone the fabG gene from Synechococcus. In this case, the initial Southern hybridization showed that the desired sequences were contained in part on an 0.8-kb BamHI-PstI fragment. This size fragment was purified in two steps and cloned into the plasmid Bluescript KS. Minipreps of plasmids from 200 colonies revealed two that contained the appropriate fragment of Synechococcus DNA. This fragment was used to probe, at high stringency, a library of Synechococcus inserts in the cosmid vector pWB79. One positive clone was found among 1728 tested. This cosmid contained a 2-kb BamHI and a 3-kb PstI fragment that had previously been identified by the *E. coli* fabG probe in digests of total Synechococcus DNA. Both fragments were subcloned from the cosmid into Bluescript KS and 2.4 kb, including the coding part of the fabG gene, were sequenced. The complete sequence of the coding region of the Synechococcus fabG gene is shown in FIG. 2 (SEQ ID NOS5 and 6).

In another aspect, the present invention provides an isolated and purified polynucleotide of from about 480 to about 40,000 base pairs that encodes a biotin carboxyl carrier protein of a cyanobacterium. That biotin carboxyl carrier protein preferably includes the amino acid residue sequence of FIG. 8 (SEQ ID NO:111) or a functional equivalent thereof. A preferred polynucleotide that encodes that polypeptide includes the DNA sequence of SEQ ID NO:110 (FIG. 8).

B. Plants

Another polynucleotide contemplated by the present invention encodes a plant polypeptide having the ability to catalyze the carboxylation of acetyl-CoA. Such a plant polypeptide is preferably a monocotyledonous or a dicotyledonous plant acetyl-CoA carboxylase enzyme.

An exemplary and preferred monocotyledonous plant is wheat, rice, maize, barley, rye, oats or timothy grass. An exemplary and preferred dicotyledonous plant is soybean, rape, sunflower, tobacco, Arabidopsis, petunia, pea, Canola, bean, tomato, potato, lettuce, spinach, alfalfa, cotton or carrot.

A monocotyledonous plant polypeptide is preferably wheat ACC, which ACC includes the amino acid residue sequence of SEQ ID NO:109 (FIG. 6) or a functional equivalent thereof. A preferred polynucleotide that encodes such a polypeptide includes the DNA sequence of SEQ ID NO:108 (FIG. 6).

Figure 3E:
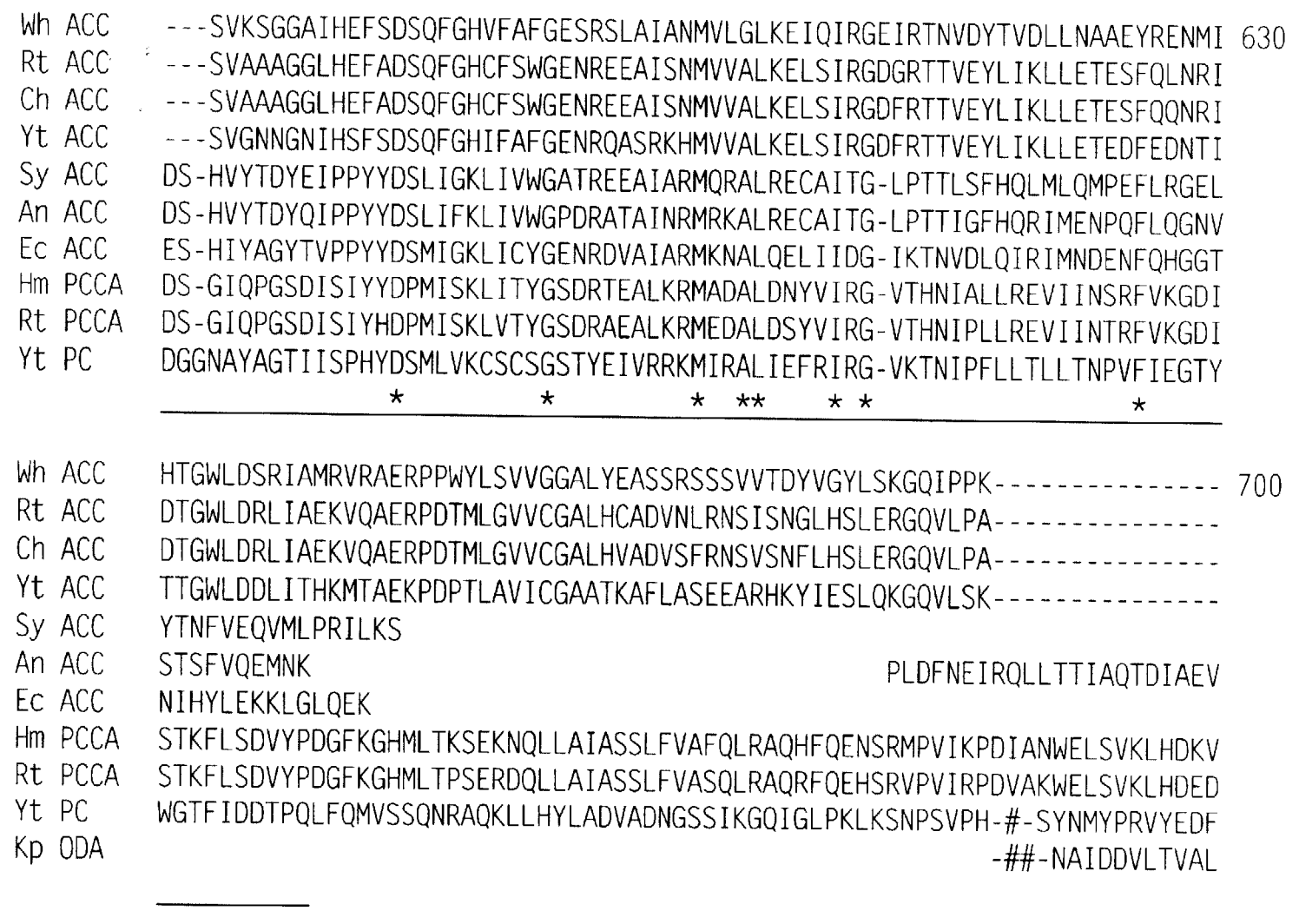

Amino acid sequences of biotin carboxylase (BC) from Anabaena and Synechococcus show great similarity with amino acid residue sequences from other ACC enzymes as well as with the amino acid residue sequences of other biotin-containing enzymes (See FIG. 3). Based on that homology, the nucleotide sequences shown in FIG. 4 (SEQ ID NOS:112 and 113) were chosen for the construction of primers for polymerase chain reaction amplification of a corresponding region of the gene for ACC from wheat. Those primers have the nucleotide sequences shown below:

Primer 1

5' TCGAATTCGTNATNATHAARGC 3' (SEQ ID NO:112);

Primer 2

5' GCTCTAGAGKRTGYTCNACYTG 3' (SEQ ID NO:113);

where N is A, C, G or T; H is A,C or T; R is A or G; Y is T or C and K is G or T. Primers 1 and 2 comprise a 14-nucleotide specific sequence based on a conserved amino acid sequence and an 8-nucleotide extension at the 5'-end of the primer to provide anchors for rounds of amplification after the first round and to provide convenient restriction sites for analysis and cloning.

cDNA amplification began with a preparation of total polyA-containing mRNA from eight day-old green plants (Triticum aestivum var. Era as described in [Lamppa, et al., 1992]). The first strand of cDNA was synthesized using random hexamers as primers for AMV reverse transcriptase following procedures described in [Haymerle, et al., 1986], with some modifications. Reverse transcriptase was inactivated by heat and low molecular weight material was removed by filtration.

The PCR was initiated by the addition of polymerase at 95° C. Amplification was for 45 cycles, each 1 min at 95°, 1 min at 42°–46° and 2 min at 72° C. Both the reactions using Anabaena DNA and the single-stranded wheat cDNA as template yielded about 440 base pair (bp) products. The wheat product was eluted from a gel and reamplified using the same primers. That product, also 440 bp, was cloned into the Invitrogeb (San Diego, Calif.) vector pCR1000 using their A/T tail method, and sequenced.

In eukaryotic ACCs, a BCCP domain is located about 300 amino acids away from the end of the BC domain, on the C-terminal side. Therefore, it is possible to amplify the cDNA covering the interval between the BC and BCCP domains using primers from the C-terminal end of the BC domain and the conserved MKM region of the BCCP. The BC primer was based on the wheat cDNA sequence obtained as described above. Those primers, each with 6- or 8-base 5'-extensions, are shown below and in FIG. 5.

Primer 3

5' GCTCTAGAATACTATTTCCTG 3' (SEQ ID NO:114)

Primer 4

5' TCGAATTCWNCATYTTCATNRC 3' (SEQ ID NO:115)

N, R and Y are as defined above. W is A or T. The BC primer (Primer 3) was based on the wheat cDNA sequence obtained as described above. The MKM primer (primer 4) was first checked by determining whether it would amplify the fabE gene coding BCCP from Anabaena DNA. This PCR was primed at the other end by using a primer based on the N-terminal amino acid residue sequence as determined on protein purified from Anabaena extracts by affinity chromatography. Those primers are shown below and in FIG. 7.

Primer 5

5' GCTCTAGAYTTYAAYGARATHMG 3' (SEQ ID NO:116)

Primer 4

5' TCGAATTCWNCATYTTCATNRC 3' (SEQ ID NO:115)

H, N, R, T, Y and W are as defined above. M is A or C. This amplification (using the conditions described above) yielded the correct fragment of the Anabaena fabE gene, which was used to identify cosmids that contained the entire fabE gene and flanking DNA. An about 4 kb XbaI fragment containing the gene was cloned into the vector Bluescript KS for sequencing.

Primers 3 and 4 were then used to amplify the intervening sequence in wheat cDNA. Again, the product of the first PCR was eluted and reamplified by another round of PCR, then cloned into the Invitrogen vector pCRII.

The complete 1.1 kb of the amplified DNA was sequenced, shown in FIG. 6. (SEQ ID NO: 108) nucleotides 376-1473. The nucleotide sequence of the BC domain is also shown in FIG. 6. (SEQ ID NO: 108) nucleotides 1-422. Three clones of the BC domain gave the sequence shown. Four clones of the 1.1-kb fragment differed at several positions, corresponding to three closely related sequences, all of which are indicated in the Figure. Most of the sequence differences are in the third codon position and are silent in terms of the amino acid sequence.

The amino acid sequence of the polypeptide predicted from the cDNA sequence for this entire fragment of wheat cDNA (1473 nucleotides) is compared with the amino acid sequences of other ACC enzymes and related enzymes from various sources in FIG. 3. The most significant identities are with the ACC of rat, chicken and yeast, as shown in the table below. Less extensive similarities are evident with the BC subunits of bacteria and the BC domains of other enzymes such as pyruvate carboxylase of yeast and propionyl CoA carboxylase of rat. The amino acid identities between wheat ACC and other biotin-dependent enzymes, within the BC domain (amino acid residues 312-630 in FIG. 3) are shown below in Table 1.

TABLE 1

|  | % identity with wheat ACC | % identity with rat ACC |
|---|---|---|
| rat ACC | 58 | (100) |
| chicken ACC | 57 |  |
| yeast ACC | 56 |  |
| Synechococcus ACC | 32 |  |
| Anabaena ACC | 30 |  |
| E. coli ACC | 33 |  |
| rat propionyl CoA carboxylase | 32 | 31 |
| yeast pyruvate carboxylase | 31 |  |

C. Probes and Primers

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected ACC gene sequence, e.g., a sequence such as that shown in FIGS. 1, 2, 6 or 8. (SEQ ID NOS:110 and 111). The ability of such nucleic acid probes to specifically hybridize to an ACC gene sequence lend them particular utility in a variety of embodiments. Most importantly, the probes can be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of an ACC gene from a cyanobacterium or a plant using PCR technology. Segments of ACC genes from other organisms can also be amplified by PCR using such primers.

To provide certain of the advantages in accordance with the present invention, a preferred nucleic acid sequence employed for hybridization studies or assays includes sequences that are complementary to at least a 10 to 30 or so long nucleotide stretch of an ACC sequence, such as that shown in FIGS. 1, 2, 6 or 8 (SEQ ID NOS:110 and 111). A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, herein incorporated by reference, or by excising selected DNA fragments from recombinant plasmids containing appropriate inserts and suitable restriction sites.

Accordingly, a nucleotide sequence of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate an ACC coding sequences for related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions depend as is well known in the art on the particular circumstances and criteria required,(e.g., on the G+C contents, type of target nucleic acid, source of nucleic acid, size of hybridization probe). Following washing of the matrix to remove nonspecifically bound probe molecules, specific hybridization is detected, or even quantified, by means of the label.

D. Expression Vector

The present invention contemplates an expression vector comprising a polynucleotide of the present invention. Thus, in one embodiment an expression vector is an isolated and purified DNA molecule comprising a promoter operatively linked to an coding region that encodes a polypeptide having the ability to catalyze the carboxylation of a biotin carboxyl carrier protein of a cyanobacterium, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

Where an expression vector of the present invention is to be used to transform a cyanobacterium, a promoter is selected that has the ability to drive and regulate expression in cyanobacteria. Promoters that function in bacteria are well known in the art. An exemplary and preferred promoter for the cyanobacterium Anabaena is the glnA gene promoter. An exemplary and preferred promoter for the cyanobacterium Synechococcus is the psbAI gene promoter. Alternatively, the cyanobacterial fabG gene promoters themselves can be used.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described by Poszkowski et al., *EMBO J.*, 3:2719 (1989) and Odell et al., *Nature*, 313:810 (1985), and temporally regulated, spatially regulated, and spatiotemporally regulated as given in Chua et al., *Science*, 244:174–181 (1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue specific or developmentally specific promoters affecting dicots or monocots.

Where the promoter is a near-constitutive promoter such as CaMV 35S, increases in polypeptide expression are found in a variety of transformed plant tissues (e.g. callus, leaf, seed and root). Alternatively, the effects of transformation can be directed to specific plant tissues by using plant integrating vectors containing a tissue-specific promoter.

An exemplary tissue-specific promoter is the Lectin promoter, which is specific for seed tissue. The Lectin protein in soybean seeds is encoded by a single gene (Le1) that is only expressed during seed maturation and accounts for about 2 to about 5 percent of total seed mRNA. The Lectin gene and seed-specific promoter have been fully characterized and used to direct seed specific expression in transgenic tobacco plants. See, e.g., Vodkin et al., *Cell*, 34:1023 (1983) and Lindstrom et al., *Developmental Genetics*, 11:160 (1990).

An expression vector containing a coding region that encodes a polypeptide of interest is engineered to be under control of the Lectin promoter and that vector is introduced into plants using, for example, a protoplast transformation method. Dhir et al., *Plant Cell Reports*, 10:97 (1991). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al. *Proc. Natl. Acad. Sci. U.S.A.*, 87:4144–48 (1990)), corn alcohol dehydrogenase 1 (Vogel et al., *J. Cell Biochem.*, (supplement 13D, 312) (1989)), corn zein 19KD gene (storage protein) (Boston et al., *Plant Physiol.*, 83:742–46), corn light harvesting complex (Simpson, *Science*, 233:34 (1986), corn heat shock protein (O'Dell et al., *Nature*, 313:810–12 (1985), pea small subunit RuBP Carboxylase (Poulsen et al., *Mol. Gen. Genet.*, 205:193–200 (1986); Cashmore et al., *Gen. Eng. of Plants*, Plenum Press, New York, 29–38 (1983), Ti plasmid mannopine synthase (Langridge et al., *Proc. Natl. Acad. Sci. USA*, 86:3219–3223 (1989), Ti plasmid nopaline synthase (Langridge et al., *Proc. Natl. Acad. Sci. USA*, 86:3219–3223 (1989), petunia chalcone isomerase (Van Tunen et al., *EMBO J.*, 7:1257 (1988), bean glycine rich protein 1 (Keller et al., *EMBO J.*, 8:1309–14 (1989), CaMV 35s transcript (O'Dell et al., *Nature*, 313:810–12 (1985) and Potato patatin (Wenzler et al., *Plant Mol. Biol.*, 12:41–50 (1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the functional properties desired, e.g. the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described by Rogers et al., *Meth. in Enzymol.*, 153:253–277 (1987). However, several other plant integrating vector systems are known to function in plants including pCaMVCN transfer control vector described by Fromm et al., *Proc. Natl. Acad. Sci. USA*, 82:5824 (1985). Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II and nopaline synthase 3' nontranslated region described by Rogers et al., in *Methods For Plant Molecular Biology*, A. Weissbach and H. Weissbach, eds., Academic Press Inc., San Diego, Calif. (1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to catalyze the carboxylation of a biotin carboxyl carrier protein of a cyanobacterium is preferably a biotin carboxylase enzyme of a cyanobacterium, which enzyme is a subunit of acetyl-CoA carboxylase and participates in the carboxylation of acetyl-CoA. In a preferred embodiment, such a polypeptide has the amino acid residue sequence of FIG. 1 or FIG. 2, or a functional equivalent of those sequences. In accordance with such an embodiment, a coding region comprises the entire DNA sequence of SEQ ID NO:1 (FIG. 1) or the DNA sequence of SEQ ID NO:1 (FIG. 1) from about nucleotide position 1300 to about nucleotide position 2650 or the DNA sequence of SEQ ID NO:5 (FIG. 2).

In another embodiment, an expression vector comprises a coding region of from about 480 to about 40,000 base pairs that encodes a biotin carboxyl carrier protein of a cyanobacterium. That biotin carboxyl carrier protein preferably includes the amino acid residue sequence of FIG. 8 (SEQ ID NO:111) or a functional equivalent thereof. A preferred such coding region includes the DNA sequence of SEQ ID NO: 110 (FIG. 8).

In still yet another embodiment, an expression vector comprises a coding region that encodes a plant polypeptide having the ability to catalyze the carboxylation of acetyl-CoA. Such a plant polypeptide is preferably a monocotyledonous or a dicotyledonous plant acetyl-CoA carboxylase enzyme.

A preferred monocotyledonous plant polypeptide encoded by such a coding region is preferably wheat ACC, which ACC includes the amino acid residue sequence of SEQ ID NO: 109 (FIG. 6) or a functional equivalent thereof. A preferred coding region includes the DNA sequence of SEQ ID NO:108 (FIG. 6).

III. Polypeptide

The present invention contemplates a polypeptide that defines a whole or a portion of an ACC of a cyanobacterium or a plant. In one embodiment, thus, the present invention provides an isolated polypeptide having the ability to catalyze the carboxylation of a biotin carboxyl carrier protein of a cyanobacterium such as Anabaena or Synechococcus. Preferably, a biotin carboxyl carrier protein includes the amino acid sequence of SEQ ID NO:111 and the polypeptide has FIG. 1 or FIG. 2 (SEQ ID NOS:5 and 6).

The present invention also contemplates an isolated and purified biotin carboxyl carrier protein of a cyanobacterium such as Anabaena, which protein includes the amino acid residue sequence of SEQ ID NO:111.

In another embodiment, the present invention contemplates an isolated and purified plant polypeptide having a molecular weight of about 220 KD, dimers of which have the ability to catalyze the carboxylation of acetyl-CoA. Such a polypeptide preferably includes the amino acid residue sequence of SEQ ID NO:109.

Modification and changes may be made in the structure of polypeptides of the present invention and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like or even counterveiling properties (e.g., antagonistic v. agonistic).

In making such changes, the hydropathic index of amino acids may be considered. The importance of the hydropathic amino acid index in conferring interactive biologic function on a protein is generally understood in the art (Kyte & Doolittle, J. Mol. Biol., 157:105–132, 1982). It is known that certain amino acids may be substituted for other amino acids having a similar hydropathic index or score and still result in a protein with similar biological activity. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, for example, enzymes, substrates, receptors, antibodies, antigens, and the like. It is known in the art that an amino acid may be substituted by another amino acid having a similar hydropathic index and still obtain a biological functionally equivalent protein. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (±3.0 +1); glutamate (±3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

The present invention thus contemplates functional equivalents of the polypeptides set forth above. A polypeptide of the present invention is prepared by standard techniques well known to those skilled in the art. Such techniques include, but are not limited to, isolation and purification from tissues known to contain that polypeptide and expression from cloned DNA using transformed cells.

IV. Transformed or transgenic cells or plants

A cyanobacterium, a plant cell or a plant transformed with an expression vector of the present invention is also contemplated. A transgenic cyanobacterium, plant cell or plant derived from such a transformed or transgenic cell is also contemplated.

Means for transforming cyanobacteria are well known in the art. Typically, means of transformation are similar to those well known means used to transform other bacteria such as E. coli. Synechococcus can be transformed simply by incubation of log-phase cells with DNA. (Golden, et al., 1987)

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Methods for DNA transformation of plant cells include Agrobacterium-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., *Biotechnology*, 3:629 (1985) and Rogers et al., *Methods in Enzymology*, 153:253–277 (1987). Further, the integration of the Ti-DNA is a relatively precise process resulting in few rearrangements. The region of DNA to be transferred is defined by the border sequences, and intervening DNA is usually inserted into the plant genome as described by Spielmann et al., *Molt Gen. Genet.*, 205:34 (1986) and Jorgensen et al., *Mol. Gen. Genet.*, 207:471 (1987).

Modern Agrobacterium transformation vectors are capable of replication in *E. coli* as well as Agrobacterium, allowing for convenient manipulations as described by Klee et al., in *Plant DNA Infectious Agents*, T. Hohn and J. Schell, eds., Springer-Verlag, New York (1985) pp. 179–203.

Moreover, recent technological advances in vectors for Agrobacterium-mediated gene transfer have improved the arrangement of genes and restriction sites in the vectors to facilitate construction of vectors capable of expressing various polypeptide coding genes. The vectors described by Rogers et al., *Methods in Enzymology*, 153:253 (1987), have convenient multi-linker regions flanked by a promoter and a polyadenylation site for direct expression of inserted polypeptide coding genes and are suitable for present purposes. In addition, Agrobacteria containing both armed and disarmed Ti genes can be used for the transformations. In those plant strains where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described by Bytebier et al., *Proc. Natl. Acad. Sci. USA*, 84:5345 (1987). Therefore, commercially important cereal grains such as rice, corn, and wheat must usually be transformed using alternative methods. However, as mentioned above, the transformation of asparagus using Agrobacterium can also be achieved. See, for example, Bytebier, et al., *Proc. Natl. Acad. Sci. USA*, 84:5345 (1987).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments. See, for example, Potrykus et al., *Mol. Gen. Genet.*, 199:183 (1985); Lorz et al., *Mol. Gen. Genet.*, 199:178 (1985); Fromm et al., *Nature*, 319:791 (1986); Uchimiya et al., *Mol. Gen. Genet.*, 204:204 (1986); Callis et al., *Genes and Development*, 1:1183 (1987); and Marcotte et al., *Nature*, 335:454 (1988).

Application of these systems to different plant strains depends upon the ability to regenerate that particular plant strain from protoplasts. Illustrative methods for the regeneration of cereals from protoplasts are described in Fujimura et al., *Plant Tissue Culture Letters*, 2:74 (1985); Toriyama et al., *Theor Appl. Genet.*, 73:16 (1986); Yamada et al., *Plant Cell Rep.*, 4:85 (1986); Abdullah et al., *Biotechnology*, 4:1087 (1986).

To transform plant strains that cannot be successfully regenerated from protoplasts, other ways to introduce DNA into intact cells or tissues can be utilized. For example, regeneration of cereals from immature embryos or explants can be effected as described by Vasil, *Biotechnology*, 6:397 (1988). In addition, "particle gun" or high-velocity microprojectile technology can be utilized. (Vasil, 1992)

Using that latter technology, DNA is carried through the cell wall and into the cytoplasm on the surface of small metal particles as described in Klein et al., *Nature*, 327:70 (1987); Klein et al., *Proc. Natl. Acad. Sci. U.S.A.*, 85:8502 (1988); and McCabe et al., *Biotechnology*, 6:923 (1988). The metal particles penetrate through several layers of cells and thus allow the transformation of cells within tissue explants.

Metal particles have been used to successfully transform corn cells and to produce fertile, stable transgenic tobacco plants as described by Gordon-Kamm, W. J. et al., *The Plant Cell*, 2:603–618 (1990); Klein, T. M. et al., *Plant Physiol.*, 91:440–444 (1989); Klein, T. M. et al., *Proc. Natl. Acad. Sci. USA*, 85:8502–8505 (1988); and Tomes, D. T. et al., *Plant Mol. Biol.*, 14:261–268 (1990). Transformation of tissue explants eliminates the need for passage through a protoplast stage and thus speeds the production of transgenic plants.

Thus, the amount of a gene coding for a polypeptide of interest (i.e., a polypeptide having carboxylation activity) can be increased in monocotyledonous plants such as corn by transforming those plants using particle bombardment methods. Maddock et al., *Third International congress of Plant Molecular Biology. Abstract* 372 (1991). By way of example, an expression vector containing an coding region for a dicotyledonous ACC and an appropriate selectable marker is transformed into a suspension of embryonic maize (corn) cells using a particle gun to deliver the DNA coated on microprojectiles. Transgenic plants are regenerated from transformed embryonic calli that express ACC. Particle bombardment has been used to successfully transform wheat (Vasil et al., 1992).

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol. Reporter*, 6:165

(1988). Expression of polypeptide coding genes can be obtained by injection of the DNA into reproductive organs of a plant as described by Pena et al., *Nature*, 325:274 (1987). DNA can also be injected directly into the cells of immature embryos and the rehydration of desiccated embryos as described by Neuhaus et al., *Theor. Appl. Genet.*, 75:30 (1987); and Benbrook et al., in *Proceedings Bio Expo 1986*, Butterworth, Stoneham, MA, pp. 27–54 (1986).

The development or regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by Agrobacterium from leaf explants can be achieved by methods well known in the art such as described by Horsch et al., *Science*, 227:1229–1231 (1985). In this procedure, transformants are cultured in the presence of a selection agent and in a medium that induces the regeneration of Shoots in the plant strain being transformed as described by Fraley et al., *Proc. Natl. Acad. Sci. U.S.A.*, 80:4803 (1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants.

A transgenic plant of the present invention containing a desired polypeptide is cultivated using methods well known to one skilled in the art. Any of the transgenic plants of the present invention can be cultivated to isolate the desired ACC or fatty acids which are the products of the series of reactions of which that catalyzed by ACC is the first.

A transgenic plant of this invention thus has an increased amount of an coding region (e.g. gene) that encodes a polypeptide of interest. A preferred transgenic plant is an independent segregant and can transmit that gene and its activity to its progeny. A more preferred transgenic plant is homozygous for that gene, and transmits that gene to all of its offspring on sexual mating.

Seed from a transgenic plant is grown in the field or greenhouse, and resulting sexually mature transgenic plants are self-pollinated to generate true breeding plants. The progeny from these plants become true breeding lines that are evaluated for, by way of example, herbicide resistance, preferably in the field, under a range of environmental conditions.

The commercial value of a transgenic plant with increased herbicide resistance or with altered fatty acid production is enhanced if many different hybrid combinations are available for sale. The user typically grows more than one kind of hybrid based on such differences as time to maturity, standability or other agronomic traits. Additionally, hybrids adapted to one part of a country are not necessarily adapted to another part because of differences in such traits as maturity, disease and herbicide resistance. Because of this, herbicide resistance is preferably bred into a large number of parental lines so that many hybrid combinations can be produced.

V. Process of increasing herbicide resistance

Herbicides such as aryloxyphenoxypropionates and cyclohexanediones inhibit the growth of monocotyledonous weeds by interfering with fatty acid biosynthesis of herbicide sensitive plants. ACC is the target enzyme for those herbicides. Dicotyledonous plants, other eukaryotic organisms and prokaryotic organisms are resistant to those compounds.

Thus, the resistance of sensitive monocotyledonous plants to herbicides can be increased by providing those plants with ACC that is not sensitive to herbicide inhibition. The present invention therefore provides a process of increasing the herbicide resistance of a monocotyledonous plant comprising transforming the plant with a DNA molecule comprising a promoter operatively linked to a coding region that encodes a herbicide resistant polypeptide having the ability to catalyze the carboxylation of acetyl-CoA, which coding region is operatively linked to a transcription-terminating region, whereby the promoter is capable of driving the transcription of the coding region in a monocotyledonous plant.

Preferably, a herbicide resistant polypeptide, a dicotyledonous plant polypeptide such as an acetyl-CoA carboxylase enzyme from soybean, rape, sunflower, tobacco, Arabidopsis, petunia, Canola, pea, bean, tomato, potato, lettuce, spinach, alfalfa, cotton or carrot, or functional equivalent thereof. A promoter and a transcription-terminating region are preferably the same as set forth above.

Transformed monocotyledonous plants can be identified using herbicide resistance. A process for identifying a transformed monocotyledonous plant cell comprises the steps of:

(a) transforming the monocotyledonous plant cell with a DNA molecule that encodes a dicotyledonous acetyl-CoA carboxylase enzyme; and (b) determining the resistance of the plant cell to a herbicide and thereby the identification of the transformed monocotyledonous plant cell.

Means for transforming a monocotyledonous plant cell are the same as set forth above.

The resistance of a transformed plant cell to a herbicide is preferably determined by exposing such a cell to an effective herbicidal dose of a preselected herbicide and maintaining that cell for a period of time and under culture conditions sufficient for the herbicide to inhibit ACC, alter fatty acid biosynthesis or retard growth. The effects of the herbicide can be studied by measuring plant cell ACC activity, fatty acid synthesis or growth.

An effective herbicidal dose of a given herbicide is that amount of the herbicide that retards growth or kills plant cells not containing herbicide-resistant ACC or that amount of a herbicide known to inhibit plant growth. Means for determining an effective herbicidal dose of a given herbicide are well known in the art. Preferably, a herbicide used in such a process is an aryloxyphenoxypropionate or cyclohexanedione herbicide.

VI. Process of altering ACC activity

Acetyl-CoA carboxyase catalyzes the carboxylation of acetyl-CoA. Thus, the carboxylation of acetyl-CoA in a cyanobacterium or a plant can be altered by, for example, increasing an ACC gene copy number or changing the composition (e.g., nucleotide sequence) of an ACC gene. Changes in ACC gene composition can alter gene expression at either the transcriptional or translational level. Alternatively, changes in gene composition can alter ACC function (e.g., activity, binding) by changing primary, secondary or tertiary structure of the enzyme. By way of example, certain changes in ACC structure are associated with changes in the resistance of that altered ACC to herbicides. The copy number of such a gene can be increased by transforming a cyanobacterium or a plant cell with an appropriate expression vector comprising a DNA molecule that encodes ACC.

In one embodiment, therefore, the present invention contemplates a process of altering the carboxylation of acetyl-CoA in a cell comprising transforming the cell with a DNA molecule comprising a promoter operatively linked to a coding region that encodes a polypeptide having the ability to catalyze the carboxylation of acetyl-CoA, which coding region is operatively linked to a transcription-terminating region, whereby the promoter is capable of driving the transcription of the coding region in the cyanobacterium.

In a preferred embodiment, a cell is a cyanobacterium or a plant cell, a polypeptide is a cyanobacterial ACC or a plant ACC. Exemplary and preferred expression vectors for use in such a process are the same as set forth above.

Where a cyanobacterium is transformed with a plant ACC DNA molecule, that cyanobacterium can be used to identify herbicide resistant mutations in the gene encoding ACC. In accordance with such a use, the present invention provides a process for identifying herbicide resistant variants of a plant acetyl-CoA carboxylase comprising the steps of:

(a) transforming cyanobacteria with a DNA molecule that encodes a monocotyledonous plant acetyl-CoA carboxylase enzyme to form transformed or transfected cyanobacteria;

(b) inactivating cyanobacterial acetyl-CoA carboxylase;

(c) exposing the transformed cyanobacteria to an effective herbicidal amount of a herbicide that inhibits acetyl-CoA carboxylase activity;

(d) identifying transformed cyanobacteria that are resistant to the herbicide; and (e) characterizing DNA that encodes acetyl-CoA carboxylase from the cyanobacteria of step (d).

Means for transforming cyanobacteria as well as expression vectors used for such transformation are preferably the same as set forth above. In a preferred embodiment, cyanobacteria are transformed or transfected with an expression vector comprising an coding region that encodes wheat ACC.

Cyanobacteria resistant to the herbicide are identified. Identifying comprises growing or culturing transformed cells in the presence of the herbicide and recovering those cells that survive herbicide exposure.

Transformed, herbicide-resistant cells are then grown in culture, collected and total DNA extracted using standard techniques. ACC DNA is isolated, amplified if needed and then characterized by comparing that DNA with DNA from ACC known to be inhibited by that herbicide.

VII. Process for Determining Herbicide Resistance Inheritibility

In yet another aspect, the present invention provides a process for determining the inheritance of plant resistance to herbicides of the aryloxyphenocypropionate or cyclohexanedione class. That process comprises the steps of:

(a) measuring resistance to herbicides of the aryloxyphenocypropionate or cyclohexanedione class in a parental plant line and in progeny of the parental plant line to;

(b) purifying DNA from the parental plant line and the progeny;

(c) digesting the DNA with restriction enzymes to form DNA fragments;

(d) fractionating the fragments on a gel;

(e) transferring the fragments to a filter support;

(f) annealing the fragments with a labelled RFLP probe consisting of a DNA molecule that encodes acetyl-CoA carboxylase or a portion thereof;

(g) detecting the presence of complexes between the fragments and the RFLP probe; and (h) correlating the herbicide resistance of step (a) with the complexes of step (g) and thereby the inheritance of herbicide resistance.

In a preferred embodiment, the herbicide resistant variant of acetyl-CoA carboxylase is a dicotyledonous plant acetyl-CoA carboxylase enzyme or a portion thereof. In another preferred embodiment, the herbicide resistant variant of acetyl-CoA carboxylase is a mutated monocotyledonous plant acetyl-CoA carboxylase that confers herbicide resistance or a hybrid acetyl-CoA carboxylase comprising a portion of a dicotyledonous plant acetyl-CoA carboxylase, a portion of a dicotyledonous plant acetyl-CoA carboxylase or one or more domains of a cyanobacterial acetyl-CoA carboxylase.

The inheritability of phenotypic traits such as herbicide resistance can be determined using RFLP analysis. Restriction fragment length polymorphisms (RFLPs) are due to sequence differences detectable by lengths of DNA fragments generated by digestion with restriction enzymes and typically revealed by agarose gel electrophoresis. There are large numbers of restriction endonucleases available, characterized by their recognition sequences and source.

Restriction fragment length polymorphism analyses are conducted, for example, by Native Plants Incorporated (NPI). This service is available to the public on a contractual basis. For this analysis, the genetic marker profile of the parental inbred lines is determined. If parental lines are essentially homozygous at all relevant loci (i.e., they should have only one allele at each locus), the diploid genetic marker profile of the hybrid offspring of the inbred parents should be the sum of those parents, e.g., if one parent had the allele A at a particular locus, and the other parent had B, the hybrid AB is by inference.

Probes capable of hybridizing to specific DNA segments under appropriate conditions are prepared using standard techniques well known to those skilled in the art. The probes are labelled with radioactive isotopes or fluorescent dyes for ease of detection. After restriction fragments are separated by size, they are identified by hybridization to the probe. Hybridization with a unique cloned sequence permits the identification of a specific chromosomal region (locus). Because all alleles at a locus are detectable, RFLP's are co-dominant alleles, thereby satisfying a criteria for a genetic marker. They differ from some other types of markers, e.g., from isozymes, in that they reflect the primary DNA sequence, they are not products of transcription or translation. Furthermore, different RFLP profiles result from different arrays of restriction endonucleases.

The foregoing examples illustrate particular embodiments of the present invention. It will be readily apparent to a

23 skilled artisan that changes, modification and alterations can be made to those embodiments without departing from the true scope or spirit of the invention.

EXAMPLE 1
Isolation of Cyanobacterial ACC Polynucleotides

The polynucleotide of SEQ ID NO: 1 contains a gene that encodes the enzyme biotin carboxylase (BC) enzyme from the cyanobacterium Anabaena 7120. This gene was cloned from a total DNA extract of Anabaena that was digested with various restriction enzymes, fractionated by gel electrophoresis, and blotted onto GeneScreen Plus (DuPont).

The blot was hybridized at low stringency (1M NaCl, 57° C.) with a probe consisting of a SstII-PstI fragment containing about 90% of the coding region of the fabG gene from E. coli. This probe identified a 3.1-kb HindIII fragment in the Anabaena digest that contained similar sequences. A mixture of about 3-kb HindIII fragments of Anabaena DNA was purified, then digested with NheI, yielding a HindIII-NheI fragment of 1.6 kb that hybridized with the fabG probe. The 1.6-kb region was purified by gel electrophoresis and cloned into pUC18. Plasmid minipreps were made from about 160 colonies, of which four were found to contain the 1.6-kb HindIII-NheI fragment that hybridized with the fabG probe. The 1.6-kb Anabaena fragment was then used as probe to screen, at high stringency (1M NaCl, 65° C.), a cosmid library of Anabaena DNA inserts averaging 40 kb in size. Five were found among 1920 tested, all of which contained the same size HindIII and NheI fragments as those identified by the E. coli probe previously. From one of the cosmids, the 3.1-kb HindIII fragment containing the Anabaena fabG gene was subcloned into pUC18 and sequenced using the dideoxy chain termination method. The complete nucleotide sequence of this fragment is shown in FIG. 1 (SEQ ID NOS:5 and 6).

A similar procedure was used to clone the fabG gene from Synechococcus. In this case, the initial Southern hybridization showed that the desired sequences were contained in part on an 0.8-kb BamHI-PstI fragment. This size fragment was purified in two steps and cloned into the plasmid Bluescript KS. Minipreps of plasmids from 200 colonies revealed two that contained the appropriate fragment of Synechococcus DNA. This fragment was used to probe, at high stringency, a library of Synechococcus inserts in the cosmid vector pWB79. One positive clone was found among 1728 tested. This cosmid contained a 2-kb BamHI and a 3-kb PstI fragment that had previously been identified by the E. coli fabG probe in digests of total Synechococcus DNA. Both fragments were subcloned from the cosmid into Bluescript KS and 2.4 kb, including the coding part of the fabG gene, were sequenced. The complete sequence of the coding region of the Anacystis fabG gene is shown in FIG. 2 (SEQ ID NOS:5 and 6).

EXAMPLE 2
Plant ACC

Figure 5:
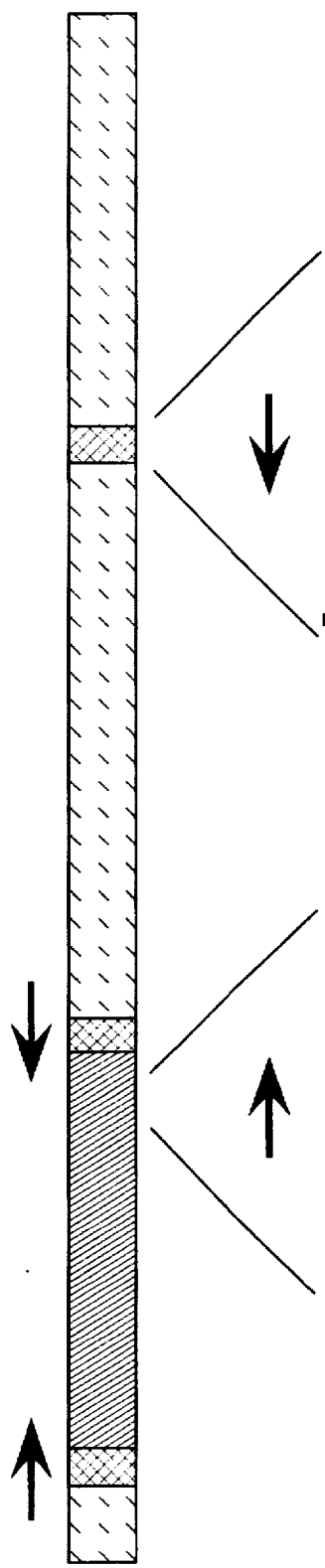
FIG. 5 shows the sequences of the oligonucleotides used as primers for the PCR used to amplify the region of wheat ACC cDNA between the BC and BCCP domains.

The amino acid sequences of the fabG genes encoding BC from Anabaena and Synechococcus are aligned with sequences of ACC and other biotin-containing enzymes from several sources in FIG. 3. This comparison allows the designation of several areas of significant conservation among all the proteins, indicated by stars in the Figure. Based on this alignment, the sequences shown in FIG. 4 were chosen for the construction of primers for the polymerase chain reaction, in order to amplify the corresponding region of the gene for ACC from wheat. The primers used for this amplification are shown in FIG. 4. Each consists of a 14-nucleotide specific sequence based on the amino acid sequence and an 8-nucleotide extension at the 5'-end of the primer to provide anchors for rounds of amplification after the first round and to provide convenient restriction sites for future analysis and cloning.

cDNA amplification began with a preparation of total polyA-containing mRNA from eight day-old green plants (Triticum aestivum var. Era as described in |Lamppa, et al., 1992|). The first strand of cDNA was synthesized using random hexamers as primers for AMV reverse transcriptase following procedures described in |Haymerle, et al., 1986|, with some modifications. Reverse transcriptase was inactivated by incubation at 90° C. and low molecular weight material was removed by filtration through centricon 100. All components of the PCR. (from the Cetus/Perkin-Elmer kit) together with the two primers shown in FIG. 4, except the Taq DNA polymerase, were incubated for 3–5 min at 95° C. The PCR was initiated by the addition of polymerase. Conditions were established and optimized using Anabaena DNA as template, in order to provide the best yield and lowest level of non-specific products for amplification of the target BC gene from Anabaena DNA. Amplification was for 45 cycles, each 1 min at 95°, 1 min at 42°–46° and 2 min at 72° C. Both the reactions using Anabaena DNA and the single-stranded wheat cDNA as template yielded about 440-bp products. The wheat product was eluted from a gel and reamplified using the same primers. That product, also 440 bp, was cloned into the Invitrogen vector pCR1000 using their A/T tail method, and sequenced. The nucleotide sequence is shown in FIG. 5.

In eukaryotic ACCs, the BCCP domain is located about 300 amino acids away from the end of the BC domain, on the C-terminal side. Therefore, it is possible to amplify the cDNA covering that interval using primers from the C-terminal end of the BC domain and the conserved MKM region of the BCCP. The BC primer was based on the wheat cDNA sequence obtained as described above. These primers, each with 6- or 8-base 5'-extensions, are shown in FIG. 6B.

Figure 7:
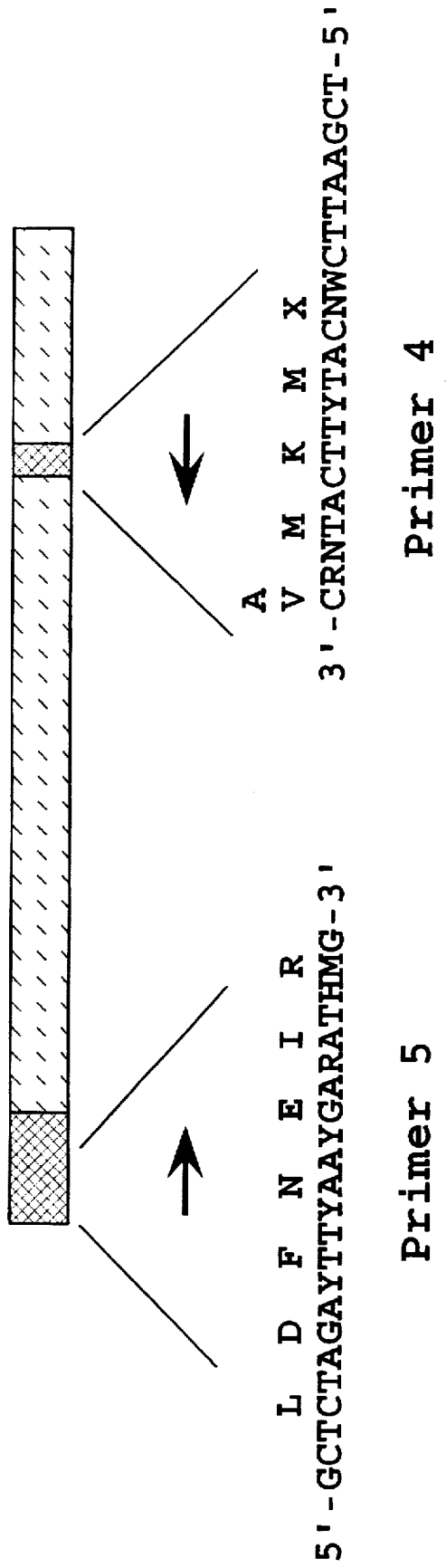
FIG. 7 shows the sequences of the oligonucleotides used as primers to amplify most of the fabE gene encoding the biotin carboxyl carrier protein from DNA of Anabaena.

The MKM primer was first checked by determining whether it would amplify the fabE gene encoding BCCP from Anabaena DNA. This PCR was primed at the other end by using a primer based on the N-terminal amino acid sequence, determined on protein purified from Anabaena extracts by affinity chromatography, shown in FIG. 6A. This amplification (using the conditions described above)worked, yielding the correct fragment of the Anabaena fabE gene, whose complete sequence is shown in FIG. 7.

The PCR-amplified fragment of the Anabaena fabE gene was used to identify cosmids (three detected in a library of 1920) that contain the entire fabE gene and flanking DNA. A 4-kb XbaI fragment containing the gene was cloned into the vector Bluescript KS for sequencing. The two primers shown in FIG. 6 were then used to amplify the intervening sequence in wheat cDNA. Again, the product of the first PCR was eluted and reamplified by another round of PCR, then cloned into the Invitrogen vector pCRII. The complete 1.1 kb of the amplified DNA was sequenced, also shown in FIG. 5.

The foregoing examples illustrate particular embodiments of the present invention. One of ordinary skill in the art will readily appreciate that changes, modifications and alterations to those embodiments can be made without departing from the true scope or spirit of the invention.

References

The references listed below and all references cited herein are incorporated herein by reference to the extent that they supplement, explain, provide a background for, or teach methodology, techniques, and/or compositions employed herein.

1. J. R. Knowles. 1989. The mechanism of biotin-dependent enzymes. Annu. Rev. Biochem. 58:195–221.
2. Alix, J.- H. 1989. A rapid procedure for cloning genes from I libraries by complementation of E. coli defective mutants: application to the fabE region of the E. coli chromosome. DNA 8:779–789.
3. Muramatsu, S., and T. Mizuno. 1989. Nucleotide sequence of the fabE gene and flanking regions containing a bent DNA sequence of Escherichia coli. Nucleic Acids Res. 17:3982.
4. Li, S., and J. E. Cronan. 1992. The gene encoding the biotin carboxylase subunit of Escherichia coli acetyl-CoA carboxylase. J. Biol. Chem. 267:855.
5. Lopez-Casillas, F., D. H. Bai, X. Luo, I. S. Kong, M. A. Hermodson, and K. H. Kim. 1988. Structure of the coding sequence and primary amino acid sequence of rat Acetyl-coenzyme A carboxylase. Proc. Natl. Acad. Sci. USA 85:5784–5788.
6. Takai, T., C. Yokoyama, K. Wada, and T. Tanabe. 1988. Primary structure of chicken liver acetyl-coenzyme A carboxylase deduced from cDNA sequence. J. Biol. Chem. : 2651–2657.
   6a. W. A. Feel, S. S. Chirala and S. J. Wakil 1992. Cloning of the yeast FAS3 gene and primary structure of yeast acetyl-CoA carboxylase. Proc Natl Acad, Sci USA 89:4534–4538.
7. J. L. Harwood. 1988. Fatty acid metabolism. Ann. Rev. Physiol. Plant Mol. Biol. 39:101–138.
8. Egin-Buhler, B., and J. Ebel. 1983. Improved purification and further characterization of ACC from culture cells of parsley. Eur. J. Biochem. 133:335–339.
9. Wurtele, E. S. and Nikolau, B. J. 1990. Arch. Biochem. Biophys. 278:179–186.
10. Slabas, A. R. and Hellyer, A. 1985. Plant Sci. 39:177–182.
11. Samols, D., C. G. Thornton, V. L. Murtif, G. K. Kumar, F. C. Haase, and H. G. Wood. 1988. Evolutionary conservation among biotin enzymes. J. Biol. Chem. 263:6461–6464.
12. H. K. Lichtenthaler. 1990. Mode of action of herbicides affecting acetyl-CoA carboxylase and fatty acid biosynthesis. Z. Naturforsch. 45c: 521–528.
13. I. Pecker, D. Chamovitz, H. Linden, G. Sandmann and J. Hirschberg. 1992. A single polypeptide catalyzing the conversion of phytoene to z-carotene is transcriptionally regulated during tomato fruit ripening. Proc Natl Acad Sci USA 89:4962–4666.
14. G. K. Lamppa, G. Morelli and N-H Chua (1985). Structure and developmental regulation of a wheat gene encoding the major chlorophyll a/b-binding polypeptide. Mol. Cell Biol. 5:1370–1378.
15. H. Haymerle, J. Herz, G. M. Bressan, R. Frank and K. K. Stanley (1986). Efficient construction of cDNA libraries in plasmid expression vectors using an adaptor strategy. Nucl. Acids Res. 14:8615–8629.
16. V. Vasil, A. M. Castillo, M. E. Fromm and I. K. Vasil (1992). Herbicide-resistant fertile transgenic wheat plants obtained by microprojectile bombardment of regenerable embryogenic callus. Biotechnology 10:667–674.
17. S. S. Golden, T. Brusslen and R. Haselkorn (1987), Genetic Enginerring of the Cyanobacterial Chromosome. Methods Enzymology 153:215–231.

---

---

What is claimed is:

1. An isolated nucleic acid segment that encodes a protein comprising the amino acid sequence of SEQ ID NO:3 or SEQ ID NO:6.

2. An isolated nucleic acid segment that comprises at least a 19 base pair contiguous nucleic acid sequence from SEQ ID NO:1 or SEQ ID NO:5, or a complement thereof, or a sequence which hybridizes to the sequence of SEQ ID NO:1 or SEQ ID NO:5 under conditions of high stringency.

3. The nucleic acid segment of claim 1, further defined as an RNA segment.

4. The nucleic acid segment of claim 1 that comprises an isolated cyanobacterial fabG gene.

5. The nucleic acid segment of claim 4, wherein said fabG gene is an Anabaena or Synechococcus fabG gene.

6. The nucleic acid segment of claim 4, comprising at least an 57 basepair contiguous nucleic acid sequence from SEQ ID NO:1 or SEQ ID NO:5, or a complement thereof, or a sequence which hybridizes to at least an 57 basepair contiguous nucleic acid sequence of SEQ ID NO:1 or SEQ ID NO:5 under conditions of high stringency.

7. A nucleic acid segment that encodes a peptide of from about 19 to about 145 amino acids in length, wherein said peptide comprises at least an about a 19 amino acid contiguous sequence from SEQ ID NO:3 or SEQ ID NO:6.

8. The nucleic acid segment of claim 7, further defined as encoding a peptide of from about 19 to about 100 amino acids in length.

9. The nucleic acid segment of claim 8, further defined as encoding a peptide of from about 19 to about 50 amino acids in length.

10. The nucleic acid segment of any of claims 4, or 7, further comprising a vector.

11. The nucleic acid segment of any of claims 4, or 7, wherein said nucleic acid is operatively linked to a promoter, said promoter expressing said nucleic acid segment.

12. A host cell comprising the nucleic acid segment of any of claims 4 or 7.

13. The host cell of claim 12, further defined as a plant cell a bacterial cell or a cyanobacterial cell.

14. The host cell of claim 13, wherein said bacterial cell is an *E. coli*, and said plant cell is a monocotyledonous or dicotyledonous plant cell.

15. The host cell of claim 14, wherein said monocotyledonous plant cell is a wheat, rice, maize, barley, rye, oats, or timothy grass cell.

16. The host cell of claim 14, wherein said dicotyledonous plant cell is a soybean, rape, sunflower, tobacco, Arabidopsis, petunia, canola, pea, bean, tomato, potato, lettuce, spinach, carrot, alfalfa, or cotton cell.

17. The host cell of claim 13, wherein said bacterial cell is an Anabaena spp., or a Synechococcus spp. cell.

18. The host cell of claim 13, wherein said cell is a monocotyledonous or a dicotyledonous plant cell.

19. An isolated nucleic acid segment comprising:
   (a) a nucleic acid segment comprising a sequence region that consists of at least about 21 contiguous nucleotides that have the same sequence as, or are complementary to, at least about 21 contiguous nucleotides of SEQ ID NO:1 or SEQ ID NO:5, or
   (b) a nucleic acid segment of from about 21 to about 4,000 nucleotides in length that hybridizes to the nucleic acid segment of SEQ ID NO:1 or SEQ ID NO:5; or the complement thereof, under conditions of high stringency.

20. The nucleic acid segment of claim 19, further defined as comprising a sequence region that consists of at least about 21 contiguous nucleotides that have the same sequence as, or are complementary to, at least about 21 contiguous nucleotides of SEQ ID NO:1 or SEQ ID NO:5.

21. The nucleic acid segment of claim 19, further defined as comprising a nucleic acid segment of from about 21 to about 4,000 nucleotides in length that hybridizes to the nucleic acid segment of SEQ ID NO:1 or SEQ ID NO:5, or a complement thereof, under conditions of high stringency.

22. A method of using a DNA segment that encodes a cyanobacterial biotin carboxylase protein or peptide, comprising the steps of:
   (a) preparing a vector in which a cyanobacterial biotin carboxylase protein or peptide-encoding DNA segment is positioned under the control of a promoter;
   (b) introducing said vector into a host cell;
   (c) culturing said host cell under conditions effective to allow expression of the encoded biotin carboxylase protein or peptide; and
   (d) collecting said expressed biotin carboxylase protein or peptide.

* * * * *

UNITED STATES PATENT AND TRADEMARK OFFICE
CERTIFICATE OF CORRECTION

PATENT NO. : 5,792,627

DATED : August 11, 1998

INVENTOR(S) : Robert Haselkorn and Piotr Gornicki

It is certified that error appears in the above-identified patent and that said Letters Patent is hereby corrected as shown below:

In claim 13, column 115, line 14, after 'plant cell', insert --,--.
In claim 14, column 115, line 17, after 'or", insert --a--.
In claim 17, column 115, line 26, delete "bacterial" and insert --cyanobacterial" therefor..

Signed and Sealed this

Twenty-ninth Day of December, 1998

Attest:

BRUCE LEHMAN

Attesting Officer          Commissioner of Patents and Trademarks